United States Patent [19]

Pierschbacher et al.

[11] Patent Number: 5,612,311
[45] Date of Patent: Mar. 18, 1997

[54] METHOD AND COMPOSITION FOR TREATING THROMBOSIS

[75] Inventors: Michael D. Pierschbacher, San Diego, Calif.; David S. Lukeman, Milan, Italy; Soan Cheng, San Diego, Calif.; William S. Craig, San Diego, Calif.; Juerg F. Tschopp, San Diego, Calif.

[73] Assignee: La Jolla Cancer Research Foundation, La Jolla, Calif.

[21] Appl. No.: 363,963

[22] Filed: Dec. 22, 1994

Related U.S. Application Data

[63] Continuation of Ser. No. 204,817, Mar. 2, 1994, abandoned, which is a continuation of Ser. No. 50,736, Apr. 14, 1993, abandoned, which is a continuation of Ser. No. 681,119, Apr. 5, 1991, abandoned, which is a continuation-in-part of Ser. No. 506,444, Apr. 6, 1990, abandoned.

[51] Int. Cl.$^6$ .............................. A61K 38/12; C07K 7/64
[52] U.S. Cl. ................................. 514/11; 514/9; 514/15; 514/16; 514/17; 530/317; 530/327; 530/328; 530/329
[58] Field of Search ............................ 514/15, 16, 17, 514/11, 9; 530/327, 328, 329, 317

[56] References Cited

U.S. PATENT DOCUMENTS

| | | | |
|---|---|---|---|
| 4,517,768 | 5/1985 | Hausermann et al. | 451/163 |
| 4,547,489 | 10/1985 | Goldstein | 514/11 |
| 4,578,079 | 3/1986 | Ruoslahti et al. | 623/11 |
| 4,589,881 | 5/1986 | Pierschbacher et al. | 623/11 |
| 4,605,512 | 8/1986 | Schaller et al. | 530/324 |
| 4,614,517 | 9/1986 | Rouslahti et al. | 530/330 |
| 4,661,111 | 4/1987 | Ruoslahti et al. | 623/11 |
| 4,661,471 | 4/1987 | Hawiger et al. | 514/13 |
| 4,666,884 | 5/1987 | Hawiger et al. | 514/13 |
| 4,683,291 | 7/1987 | Zimmerman et al. | 530/324 |
| 4,789,734 | 12/1988 | Ruoslahti et al. | 530/395 |
| 4,792,525 | 12/1988 | Rouslahti et al. | 435/240 |
| 4,857,508 | 8/1989 | Adams et al. | 514/18 |
| 4,879,313 | 11/1989 | Tjoeng et al. | 514/616 |
| 4,929,601 | 5/1990 | Brunetti et al. | 514/18 |
| 4,943,562 | 7/1990 | Jolles et al. | 514/18 |
| 5,023,233 | 6/1991 | Nutt et al. | 514/11 |
| 5,037,808 | 8/1991 | Tjoeng et al. | 514/20 |
| 5,041,380 | 8/1991 | Rouslahti et al. | 435/240.2 |
| 5,066,592 | 11/1991 | Huang et al. | 435/240.2 |

FOREIGN PATENT DOCUMENTS

| | | | |
|---|---|---|---|
| 2000048 | 4/1990 | Canada . | |
| 0275748 | 12/1987 | European Pat. Off. . | |
| 317053 | 5/1988 | European Pat. Off. . | |
| 0341915 | 5/1989 | European Pat. Off. . | |
| 314576 | 5/1989 | European Pat. Off. | C07K 5/10 |
| 332523 | 9/1989 | European Pat. Off. | C12N 15/00 |
| 338634 | 10/1989 | European Pat. Off. . | |
| 347931 | 12/1989 | European Pat. Off. | C07K 7/04 |
| 368486 | 5/1990 | European Pat. Off. . | |
| 382451 | 8/1990 | European Pat. Off. | C07K 7/10 |
| 410537 | 1/1991 | European Pat. Off. | C07K 7/64 |
| 410539 | 1/1991 | European Pat. Off. | C07K 7/06 |
| 410540 | 1/1991 | European Pat. Off. | C07K 7/06 |
| 410541 | 1/1991 | European Pat. Off. | C07K 7/06 |
| 2617170 | 12/1988 | France | C07K 7/06 |
| 3831714 | 3/1990 | Germany | C07K 13/00 |
| 3841763A1 | 6/1990 | Germany . | |
| 2207922 | 2/1989 | United Kingdom . | |
| WO88/03151 | 5/1988 | WIPO | C07K 7/00 |
| WO89/00200 | 1/1989 | WIPO . | |
| 8905150 | 6/1989 | WIPO . | |
| WO89/04837 | 6/1989 | WIPO . | |
| WO89/05155 | 6/1989 | WIPO | A61K 39/395 |
| WO89/07609 | 8/1989 | WIPO . | |
| WO90/00178 | 1/1990 | WIPO . | |
| WO90/02751 | 3/1990 | WIPO . | |
| WO90/06943 | 6/1990 | WIPO . | |
| WO90/14103 | 11/1990 | WIPO | A61K 39/395 |
| WO90/15620 | 12/1990 | WIPO . | |
| WO91/01331 | 2/1991 | WIPO . | |
| WO91/04031 | 4/1991 | WIPO | A61K 31/62 |
| WO91/15515 | 10/1991 | WIPO . | |
| WO91/15516 | 10/1991 | WIPO . | |

OTHER PUBLICATIONS

Gehlsen et al., J. Cell. Biol. 106:925–930 (1988).
Gehlsen et al., J. Cell. Biol. 105:3097–3104 (1987).
Siebers et al., Eur. J. Biochem. 178:131–140 (1988).
Ruoslahti et al., Cell 44:517–518 (1986).
Ruoslahti et al., Falk Symposium 43:239–244 (1987).
Bodanszky, Principles of Peptide Synthesis 217–222 (1984).
Marx, Science 248:1491–1493 (1990).
Creighton, Proteins 9 (1984).
Dayhoff, Atlas of Protein Sequences and Structure 5:89–99 (1972).
Joubert et al., Biochim. Biophys. Acta. 579:228–233 (1979).
Gan et al., J. Biol. Chem. 263(36):19827–19832 (1988).
Huang et al., J. Biol. Chem. 262(33):16157–16163 (1987).
Pelton et al., Proc. Natl. Acad. Sci. USA 82:236–239 (1985).
Sakakibara et al., BBA 303:198–202 (1973).
Kaiser and Kezcy, Science 223:249–255 (1984).
Ohsaku et al., Int. J. Biol. Macromol. 6:234–240 (1984).
Cheresh, Chem. Abstract 104, abstract No. 183980c (1986).
Yamada, Chem. Abstract 107, abstract No. 5066p (1987).
Poole, Chem. Abstract 105, abstract No. 169400c (1986).
Toda et al., J. Cell. Biol. 105:3097–3104 (1987).

(List continued on next page.)

*Primary Examiner*—Christina Y. Chan
*Assistant Examiner*—T. D. Wessendorf
*Attorney, Agent, or Firm*—Campbell & Flores LLP

[57] ABSTRACT

The invention provides cyclic peptides which inhibit platelet aggregation without causing prolonged bleeding time. The invention provides RGD or KGD containing peptides which are cyclized and contain hydrophobic moieties adjacent to the carboxy terminus of the RGD sequence. Peptides of this nature are also provided which contain in addition to the hydrophobic moiety an adjacent positively charged moiety. Such peptides have a high affinity for the receptor IIb/IIIa and a low affinity for the fibronectin and vitronectin receptors. Such peptides can be administered in a suitable physiologically acceptable carrier to therapeutically treat thrombosis.

3 Claims, 13 Drawing Sheets

OTHER PUBLICATIONS

Singer et al., J. Cell. Biol. 104:573–584 (1987).
Lash et al., Dev. Biol. 123:411–420 (1987).
Pierschbacher and Ruoslahti, J. Biol. Chem. 262:17294–17298 (1987).
Haverstick et al., Blood 66:946–952 (1985).
Ruggeri et al., Proc. Natl. Acad. Sci. USA 83:5708–5712 (1986).
Ginsberg et al., J. Biol. Chem. 260:3931–3936 (1985).
Pierschbacher et al., Proc. Natl. Acad. Sci. USA 81:5985–5988 (1984).
Kloczewisk et al., Biochemistry 23:1767–1774 (1984).
Gartner and Bennett, J. Biol. Chem. 260:11891–11894 (1985).
Kleffer and Phillips, Annu. Rev. Cell Biol. 36:329–357 (1990).
Plow et al., Proc. Natl. Acad. Sci. USA 82:8057–8061 (1985).
Pytela et al., Proc. Natl. Acad. Sci. USA 82:5766–5770 (1985).
Pytela et al., Cell 40:191–198 (1985).
Pytela et al., Science 231:1559–1562 (1985).
Gardner et al, Cell 42:439–448 (1985).
Pierschbacher et al., Nature 309:30–33 (1984).
D'Souza et al., J. Biol. Chem. 263:3943–3951 (1988).
Parise et al., J. Biol. Chem. 262:12597–12602 (1987).
Haskei et al., Thromb. Res. 56:687–695 (1988).
Plow et al., Blood 70:110–115 (1987).
Ruoslahti et al., J. Clin. Invest. 87:1–5 (1991).
Ali et al., Peptides Proc. 11th Amer. Peptide Symposium, La Jolla, CA, Marshall & Rivier, eds. (Jul. 9–14, 1989).
Garsky et al., Proc. Natl. Acad. Sci. USA 86:4022–4026 (1989).
Dennis et al., Proc. Natl. Acad. Sci. USA 87:2471–2475 (1989).
Chao et al., Proc. Natl. Acad. Sci. USA 86:8050–8054 (1989).
Shebuski et al., J. Biol. Chem. 264:21550–21556 (1989).
Huang et al., Biochemistry 28:661–666 (1989).
Spatola and Krzysztof, Tetrahedron 44(3):821–833 (1988).
Garo and Spatola, Biochem. Biophys. Res. Commun. 120(3):840–845 (1984).
Edwards and Spatola, Biochem. Biophys. Res. Commun. 136(2):730–736 (1986).
Spatola and Edwards, Biopolymers 25:S229–S244 (1986).
Davies et al., Biochem. Soc. Trans. 18:11326–11328 (1990).
Drickamer et al., J. Biol. Chem. 261:6878–6887 (1986).
Rauvala et al., J. Cell. Biol. 107:2293–2305 (1988).
Maes et al., Fed. Europ. Biochem. Soc. 241:41–45 (1988).
Moos et al., Nature 334:701–703 (1988).
Neurath et al., Mol. Immun. 27:539–549 (1990).
Kirchofer et al., J. Biol. Chem. 265:18525–18530 (1990).
Ratner et al., Nature 313:277–284 (1985).
Bond et al., Biochemistry 28:6110–6113 (1989).
Ohlstein et al., Thromb. Res. 46:576–585 (1987).
Harvey, J. Toxicol.—Toxin Reviews 3:91–137 (1984).
Dufton, CRC Crit. Rev. in Biochem. 14:113–171 (1983).
Olson, Nature 228:438–442 (1970).
Pelton, J. Med. Chem. 29:2370–2375 (1986).
Lebl, Collection Czechosloval Chem. Commun. 49:2680–2688 (1984).
Stanfield, J. Org. Chem. 51:5153–5156 (1986).
Barker, Protein Society 2nd Symposium (1987).
Pierschbacher et al., J. Biol. Chem. 262 17294–17298 (1987).
Lam et al. J. Biol. Chem. 262 947–950 (1987).
Cordroy et al. J. Clin. Invest. 84 939–944 (1989).

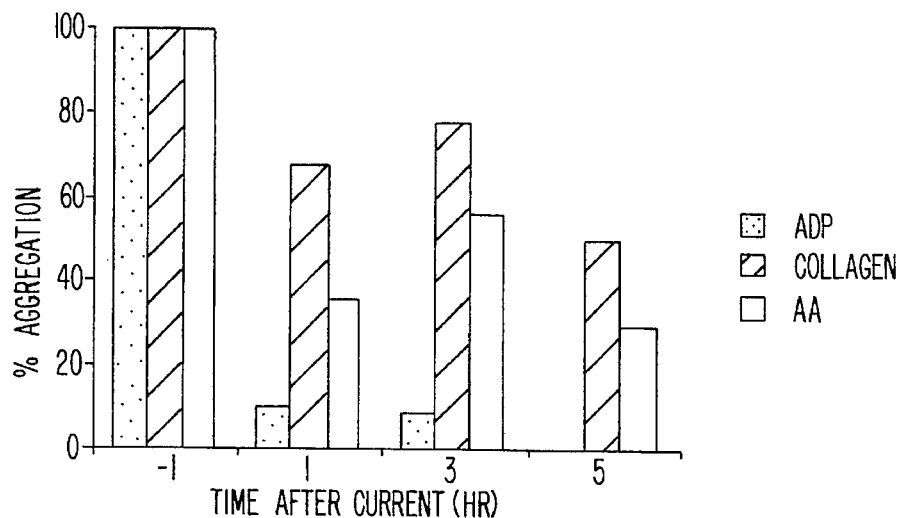
FIG. 3a
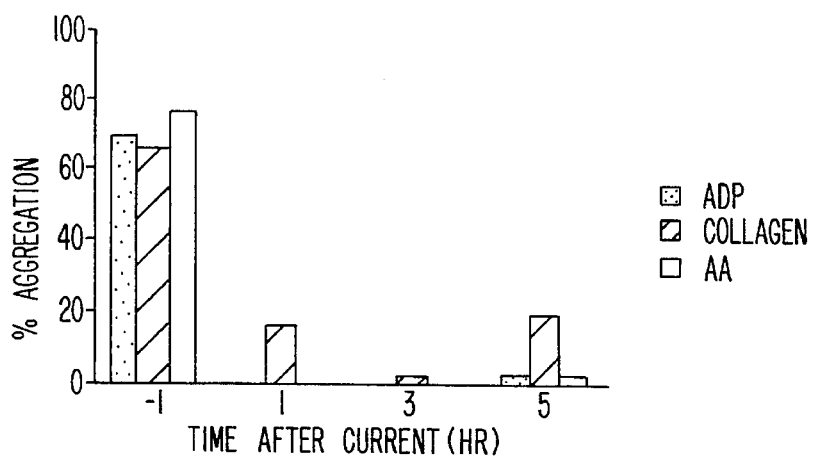
FIG. 3b1
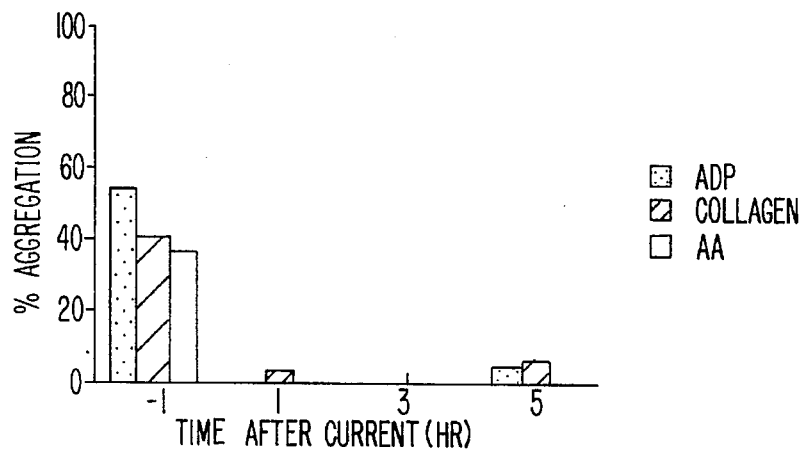
FIG. 3b2

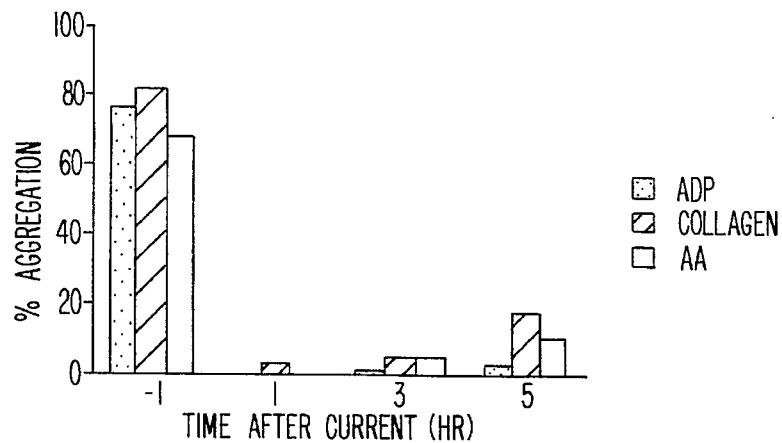
FIG. 3b3
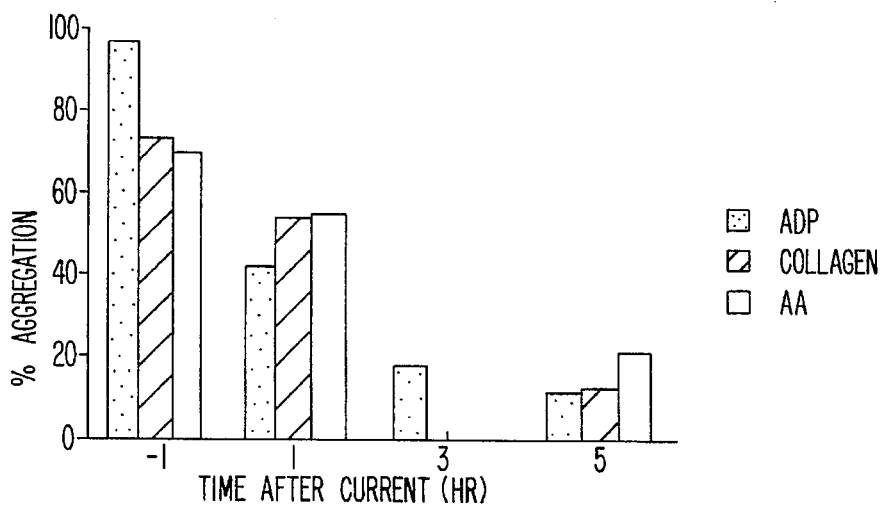
FIG. 3c1
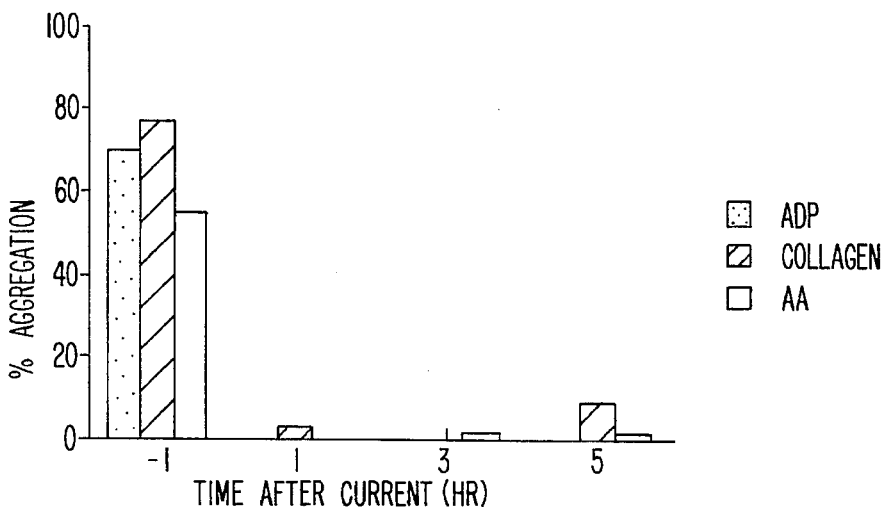
FIG. 3c2

| | |
|---|---|
| Analogue 2G | 127 ± 41  (3) |
| 10 mg/kg | |
| Analogue 4Q | |
| 5 mg/kg | 165 ± 10  (2)[b] |
| 5 mg/kg (Low platelet count) | >300  (2) |
| 10 mg/kg | >300  (1)[c] |
| Analogue 4R | |
| 3 mg/kg | 95  (1) |
| 10 mg/kg | >300  (1)[c] |

[a] values are mean ± SEM for the number of determinations that appears in parentheses.

Statistical significance vs. control denoted as follows:

Effects of RGD Peptides on Hemodynamic Parameters

| Treatment | Mean Arterial Pressure (mm Hg) | Heart Rate (Beats/Min) | Platelet Count (10³/ml) | Bleeding Time (Min) |
|---|---|---|---|---|
| ANALOGUE 2G | | | | |
| (10 mg/kg) (N-3) | | | | |
| Baseline | 104±5 | 160±10 | 480±12 | 2.9±0.6 |
| 1 hr. | 96±7 | 172±8 | 409±19 | 2.8±0.3 |
| 3 hr. | ND | ND | 395±36 | 2.6±0.1 |
| 5 hr. | ND | ND | 556±16 | 2.6±0.1 |
| ANALOGUE 4Q | | | | |
| (5 mg/kg) (N-2) | | | | |
| Baseline | 103±3 | 158±9 | 316±52 | 2.8±0.3 |
| 1 hr. | 107±6 | 160±10 | 406±185 | 2.8±0.3 |
| 3 hr. | 110±10 | 168±7 | 375±25 | 3.6±0.1 |
| 5 hr. | ND | ND | 355±47 | 3.0±0.5 |
| (10 mg/kg) (N-1) | | | | |
| Baseline | 100 | 162 | 307 | 4.0 |
| 1 hr. | 104 | 170 | 420 | 7.5 |
| 3 hr. | 105 | 160 | 379 | 5.5 |
| 5 hr. | 107 | 165 | 290 | 5.5 |
| ANALOGUE 4R | | | | |
| (3 mg/kg) (N-1) | | | | |
| Baseline | 103 | 170 | 393 | 4.0 |
| 1 hr. | 110 | 165 | 367 | 4.0 |
| 3 hr. | ND | ND | 420 | 4.0 |
| 5 hr. | ND | ND | 575 | 5.0 |
| (10 mg/kg) (N-1) | | | | |
| Baseline | 100 | 162 | 512 | 4.0 |
| 1 hr. | 95 | 168 | 513 | 5.5 |
| 3 hr. | 102 | 172 | 491 | 5.0 |
| 5 hr. | 107 | 170 | 460 | 5.0 |

PEPTIDE EFFECTS ON ANIMAL HEMATOLOGY & BLEEDING TIMES
(Experiment 1)

| HEMATOLOGY PARAMETERS | SHUNT 1 | | | SHUNT 2 | |
|---|---|---|---|---|---|
| | 0 Hr. | 2 Hr. | 0 Hr. | 1 Hr. | 2 Hr. |
| Red Blood Cells (M/UL) | 4.78 | 4.00 | 4.49 | 4.70 | 4.11 |
| White Blood Cells (K/UL) | 9.3 | 4.0 | 12.0 | 11.4 | 8.8 |
| Platelets (K/UL) | 332 | 250 | 269 | 276 | 231 |
| Hematocrit (%) | 42 | 35 | 39 | 41 | 36 |
| Hemoglobin (G/UL) | 12.5 | 10.7 | 12.0 | 12.4 | 10.6 |
| Bleeding Time* (Min) | 4:48 | 4:55 | ND | 5:02 | 3:05 |
| Clotting Time (Sec) | 120 | 130 | ND | ND | 124 |

*Represents average of two simultaneous determinations.
ND-not determined.

FIG. 8

PEPTIDE EFFECTS ON ANIMAL
HEMATOLOGY & BLEEDING TIMES
(Experiment 2)

| HEMATOLOGY PARAMETERS | SHUNT 1 | | | SHUNT 2 | |
|---|---|---|---|---|---|
| | 0 Hr. | 2 Hr. | 0 Hr. | 1 Hr. | 2 Hr. |
| Red Blood Cells (M/UL) | 4.78 | 5.12 | 5.06 | 4.65 | 4.81 |
| White Blood Cells (K/UL) | 6.6 | 12.9 | 10.7 | 10.0 | 10.7 |
| Platelets (K/UL) | 274 | 281 | 281 | 264 | 286 |
| Hematocrit (%) | 39 | 41 | 41 | 37 | 38 |
| Hemoglobin (G/UL) | 12.3 | 13.2 | 12.9 | 12.0 | 12.4 |
| Bleeding Time* (Min) | 4:15 | 4:27 | ND | 4:46 | 4:05 |
| Clotting Time (Sec) | 131 | 125 | ND | ND | 132 |

*Represents average of two simultaneous determinations.
ND-not determined.

FIG. 11

IN VIVO AND EX VIVO EVALUATIN OF PEPTIDES IN A RABBIT MODEL

| CODE | Rabbit BT CBT Ratio | Rabbit Ex Vivo Plt Aggn % Inh | Rabbit PBF | Dose Bol + Inf | N | Sequence |
|---|---|---|---|---|---|---|
| Control | 1.1 | 11 | Normal | (Saline) | 2 | |
| 8X | 0.7 | 94 | Normal | 1.5 + 0.036 | 1 | Ac-CNPRGD(Y-OMe)RC-NH2 |
| 8X | 2.1 | 98 | Normal | 4.5 + 0.108 | 1 | Ac-CNPRGD(Y-OMe)RC-NH2 |
| 11J | 0.93 (dose too low) | 17 | Normal | 1.5 + 0.036 | 1 | Ac-CNPRGD(Y-OMe)EC-NH2 |
| 11K | 0.69 (dose too low) | 29 | Normal | 1.5 + 0.036 | 1 | Ac-CNPRGD(Y-OMe)AC-NH2 |
| 11L | 1.09 (dose too low) | 12 | Normal | 1.5 + 0.036 | 1 | Ac-CNPRGD(Y-OMe)(dR)C-NH2 |
| 11P | 1.42 (dose too low) | 10 | Normal | 1.5 + 0.036 | 1 | Ac-CNPRGD(Y-OMe)QC-NH2 |
| 11Q | 0.70 (dose too low) | 63 | Normal | 1.5 + 0.036 | 1 | Ac-CNPKGD(Y-OMe)RC-NH2 |
| 11R | 1.40 (dose too low) | 19 | Normal | 1.5 + 0.036 | 1 | Ac-CNPRGD(Y-OMe)KC-NH2 |
| 11S | 1.00 (dose too low) | 10 | Normal | 1.5 + 0.036 | 1 | Ac-CNPRGD(Y-OMe)(Ct)C-NH2 |
| 11V | 1.17 (dose too low) | 0 | Normal | 1.5 + 0.036 | 1 | Ac-CNPRGD(Y-OMe)(Nle)C-NH2 |
| 4Q | 1.4 | 97 | Decreased | 3.75 + 0.090 | 2 | RPenGHRGDWRCR |
| 4Q | 1.4 | 99 | Decreased | 11.4 + 0.270 | 1 | RPenGHRGDWRCR |
| 5Q | 1.3 | 27 | ND | 0.27 + 0.007 | 1 | RPmcGHRGD(Y-OMe)RCR |
| 5Q | 0.75 | 93 | Decreased | 1.5 + 0.036 | 1 | RPmcGHRGD(Y-OMe)RCR |
| 7B | 1.2 | 32 | ND | 0.59 + 0.014 | 1 | RPmcGHRGD(p-1-F)RCR |
| 7B | 1.1 | 96 | Decreased | 3.0 + 0.072 | 2 | RPmcGHRGD(p-1-F)RCR |
| 7T | 1.1 | 94 | Decreased | 1.5 + 0.036 | 2 | RPmcGHRGD(p-NO2-F)RCR |

Dose of [mg/kg] bolus + [mg/kg/min x 60 min] infusion

METHOD AND COMPOSITION FOR TREATING THROMBOSIS

This application is a continuation of application Ser. No. 08/204,817, filed Mar. 2, 1994, now abandoned which is a continuation of Ser. No. 08/050,736, filed Apr. 14, 1993, now abandoned, which is a continuation of Ser. No. 07/681,119, filed Apr. 5, 1991, now abandoned, which is a continuation-in-part of Ser. No. 07/506,444, filed Apr. 6, 1990, now abandoned.

BACKGROUND OF THE INVENTION

The invention relates generally to methods of treating thrombosis, and, more particularly, to such methods using peptides.

The formation of a blood clot within a blood vessel, a process termed thrombosis, is a serious condition which can cause tissue damage and, if untreated, eventually death. Thrombosis formation is dependent upon platelet aggregation. The interaction of blood platelets with the endothelial surface of injured blood vessels and with other platelets is a major factor in the course of development of thrombi.

Various products for dissolving such clots are now available, such as asprin, dipyridamole and heparin. These products generally kill or remove platelets, which can eliminate the clot, but have the potential serious side effect of causing prolonged bleeding. Moreover, the effect of such products can only be reversed by new platelets being formed or provided.

Platelet aggregation is dependent upon the binding of fibrinogen and other serum proteins to the GP IIb/IIIa glycooprotein complex on the platelet plasma membrane. GP IIb/IIIa is a member of a large family of cell adhesion receptors known as integrins, many of which are known to recognize an Arg-Gly-Asp (RGD) tripeptide recognition sequence. Individual receptor specificity is determined by the conformation that the RGD sequence adopts in each individual ligand. Inhibition of GP IIb/IIIa receptor binding, and therefore of platelet aggregation, without inhibition of other cell adhesion receptors would be necessary for the prevention of coronary thrombosis.

There thus exists a need for a composition able to specifically inhibit the platelet aggregation receptor GP IIb/IIIa and to dissolve blood clots without removing or killing platelets and without causing detrimental side effects such as prolonged bleeding. The present invention satisfies this need and provides related advantages as well.

SUMMARY OF THE INVENTION

The invention provides cyclic peptides which inhibit platelet aggregation without causing prolonged bleeding time. The invention provides RGD or KGD containing peptides which are cyclized and contain hydrophobic moieties adjacent to the carboxy terminus of the RGD sequence. Peptides of this nature are also provided which contain in addition to the hydrophobic moiety an adjacent positively charged moiety. Such peptides have a high affinity for the receptor IIb/IIIa and a low affinity for the fibronectin and vitronectin receptors. Such peptides can be administered in a suitable physiologically acceptable carrier to therapeutically treat thrombosis.

BRIEF DESCRIPTION OF THE DRAWINGS

FIGS. 3a, 3b1, 3b2, 3b3 and 3c1, 3c2 show the platelet aggregation values for each peptide dose following time after induction of coronary thrombosis.

FIG. 4 shows the effects of the peptides injected in Example VII on coronary blood flow and thrombosis.

FIG. 5 shows the effects of the peptides injected in Example VII on hemodynamic responses.

FIG. 8 shows the hematology parameters in animal 1 for control treatment (shunt 1) and for treatments with the peptide of Example VIII (shunt 2).

FIG. 11 shows the hematology parameters in animal 2 for control treatment (shunt 1) and for treatments with the peptide of Example VIII (shunt 2).

FIG. 12 shows the in vivo and ex vivo efficacy of various hydrophobically enhanced peptides in a rabbit model.

DETAILED DESCRIPTION OF THE INVENTION

Figure 1A:
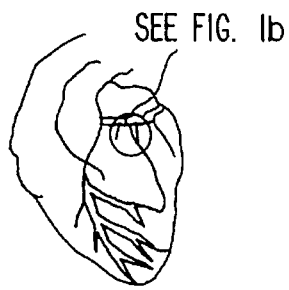
FIGS. 1a, 1b and 1c illustrate the insertion of electromagnetic flow probe, intra-coronary electrode and screw occluder into the left circumflex coronary artery FIGS. 1a and 1b and shows coronary blood flow before and after adjustment of the critical stenosis FIG. 1c.

The invention provides cyclic peptides which inhibit platelet aggregation without causing prolonged bleeding time. In one embodiment, peptides are also provided which are cyclic and contain the sequence $X_a GDX_b^*$ wherein $X_a$ is a positively charged amino acid, $X_b$ is a hydrophobic moiety and * is a positively charged moiety. These peptides are effective in inhibiting platelet aggregation and can therefore advantageously be used to dissolve blood clots as well as prevent inappropriate growth of vascular smooth muscle cells and arterial graft occlusion. Unexpectedly, such treatment does not cause the concomitant significant prolonged bleeding which has limited the usefulness of other anti-thrombotic agents. The use of such peptides is therefore a significant improvement over conventional therapy, including such therapy utilizing other RGD-containing peptides.

As used herein, references to "Arg-Gly-Asp containing peptides" or "RGD peptides" are intended to refer to peptides having one or more Arg-Gly-Asp containing sequences which may function as binding sites for a receptor of the "Arg-Gly-Asp family of receptors", i.e., those recognizing and binding to the Arg-Gly-Asp sequence. It is understood that functional equivalents of Arg-Gly-Asp such as Lys-Gly-Asp (KGD) or chemical structures other than amino acids which functionally mimic the Arg-Gly-Asp tri-peptide sequence are also included within this definition. While the Arg-Gly-Asp sequence and its functional equivalents have been found to necessarily be invariant in order to retain the binding activity, the composition of the remaining peptide as well as any other chemical moiety present in conjunction with the peptide may vary without necessarily affecting the activity of the binding site. Where specific chemical structures or sequences beyond the Arg-Gly-Asp sequence are presented, it is intended that various modifications which do not destroy the function of the binding site are to be encompassed without departing from the definition of the peptide.

As used herein, the term "bridge" refers to a chemical bond between two amino acids, amino acid derivatives or other chemical moieties in a peptide other than the amide bond by which the backbone of the peptide is formed unless the amide bond cyclizes the peptide to form a lactam.

As used herein, the term "peptide bond" or "peptide linkage" refers to an amide linkage between a carboxyl group of one amino acid and the α-amino group of another amino acid.

As used herein, the term "peptide" is intended to include molecules containing amino acids linearly coupled through peptide bonds. Such peptides may additionally contain amino acid derivatives or non-amino acid moieties. The amino acids can be in the L or D form so long as the binding function of the peptide is maintained. Such peptides can be of variable length, preferably between about 4 and 200 amino acids, more preferably between about 7 and 35 amino acids, most preferably about 19 amino acids. The term amino acid refers both to the naturally occurring amino acids and their derivatives, such as O—Me—Y and p-Cl—F, as well as other moieties characterized by the presence of both an available carboxyl group and amine group. Non-amino acid moieties which can be contained in such peptides include, for example, nitrogen containing moieties such as amines, acyl groups or amino acid mimicking structures. Mimicking structures are those structures which exhibit substantially the same spatial arrangement of functional groups as amino acids but do not have both the α-amino and α-carboxyl groups characteristic of amino acids.

As used herein, the term "cyclic peptide" refers to a peptide having an intramolecular bond between two non-adjacent amino acids within a peptide. The intramolecular bond includes, but is not limited to backbone to backbone, side-chain to backbone and side-chain to side-chain cyclizations. Various amino acid derivatives and chemical moieties can participate in such bonds, including, for example, Pen, Pmp and Pmp analogues and Pmc and Pmc analogues. Pmc is also known as amino-Pmp (am-pmp).

As used herein, the terms "not prolonging bleeding time" or "not substantially prolonging bleeding time" refer to a bleeding time which is substantially the same as that obtained from an untreated animal. Thus peptides which do not prolong bleeding time are those which when administered to an animal do not extend the bleeding time by more than a factor of two as measured by assays such as that provided in Example VII 6., infra.

The one-letter and three-letter abbreviations for amino acids and other moieties used herein are given as follows:

| A | Ala | Alanine |
|---|---|---|
|   | α-ABA | α-Amino isobutyric acid |
| R | Arg | Arginine |
| N | Asn | Asparagine |
| D | Asp | Aspartic acid |
|   | Cha | Cyclohexyl-alanine |
|   | Cit | Citrulline |
| C | Cys | Cysteine |
| Q | Gln | Glutamine |
| E | Glu | Glutamic acid |

-continued

| G | Gly | Glycine |
|---|---|---|
| H | His | Histidine |
|   | Hpa | Homophenylalanine |
| I | Ile | Isoleucine |
| L | Leu | Leucine |
| K | Lys | Lysine |
| M | Met | Methionine |
|   | napA | naphthyl-alanine analogues |
|   |  | 2 NapA (2-naphthyl) alanine |
|   |  | O—Me—Y O-methyl-Tyrosine |
|   | O-n-butyl-Y | O-n-butyl-tyrosine |
|   | O-n-hexyl-Y | O-n-hexyl-tyrosine |
|   | Orn | Ornithine |
|   | p-amino-F | para-amino-phenylalanine |
|   | Pas | 6,6-Cyclopentamethylene-2-Aminosuberic acid analogues |
|   | Pen | Penicillamine |
| F | Phe | Phenylalanine |
|   | Phg | phenylglycine |
|   | p-iodo-F | para-iodo-phenylalanine |
|   | Pmc | amino-β$_1$, β-pentamethylene-β-mercaptopropionic acid |
|   | Pmp | β$_1$, β-pentamethylene-β-mercaptopropionic acid analogues |
|   |  | p-Cl—F para-chloro-phenylalanine |
|   | p-nitro-F | para-nitro-phenylalanine |
| P | Pro | Proline |
| S | Ser | Serine |
|   | SuccAla | Succinyl-alanine |
| T | Thr | Threonine |
| W | Trp | Tryptophan |
| Y | Tyr | Tyrosine |
| V | Val | Valine |
|   | 3,5-diiodo-Y | 3,5-diiodo-tyrosine |

As used herein, the term "hydrophobic" is intended to include those amino acids, amino acid derivatives, amino acid mimics and chemical moieties which are non-polar. Hydrophobic amino acids include Phe, Val, Trp, Ile and Leu. Other hydrophobic moieties useful in the invention are O—Me—Y, p-Cl—F, ChA, O-n-hexyl-Y, 3,5-diiodo-Y, Hpa, 2-Nal, O-N-butyl-Y, p-nitro-F, Phg, p-iodo-F, P-amino-F and Cit.

As used herein, the term "positively charged moiety" refers to those amino acids, amino acid derivatives, amino acid mimics and chemical moieties which are positively charged. Positively charged amino acids include, for example, Lys, Arg and His and Orn.

Although the invention will be described with reference to RGD receptor binding peptides, it is understood that functional equivalents known to those skilled in the art can be substituted for the RGD sequence without departing from the spirit of the invention. One skilled in the art will be able to use such functional equivalents to practice the invention described herein.

It is now well-established that the amino acid sequence RGD is the cell binding site in a number of proteins, including for example, fibronectin, vitronectin and type IV collagen. The RGD binding site is recognized by a family of cell surface receptors, termed integrins. Platelets contain a large repertoire of RGD-cell surface receptors, each of which recognizes one or more RGD containing ligands to perform various physiological functions. GP IIb/IIIa is one such integrin receptor found in platelets. The ligands recognized by this receptor include fibrinogen and other serum proteins. GP IIb/IIIa is primarily responsible, through interaction with other platelets to form aggregates and through interactions with the endothelial surface of injured blood vessels, for the development of coronary artery thrombosis. When provided in soluble form, RGD peptides can inhibit cell attachment or platelet aggregation through competition with other RGD containing ligands. See for example U.S.

Pat. Nos. 4,578,079, 4,517,686, 4,792,525 and 4,683,291, which are incorporated herein by reference.

Because prolongation of bleeding time can be an undesirable side effect of thrombolytic therapy the present peptides which do not have this side effect are extremely useful. The effect of a peptide on bleeding time can be easily determined by one skilled in the art using for example, a protocol as described in Example VII 6. Hemodynamic Responses.

Unexpectedly, the presence of a positively-charged moiety in the "+4 position" of the RGD binding site, i.e., the position adjacent to the residue in the X position of the sequence RGDX, confers the characteristic of not prolonging bleeding time to platelet aggregation inhibiting peptides. Illustrative of such a peptide is Ac-CNPRGD(O—Me—Y)RC—$NH_2$ ("8×"). Such a positive charge can, for example, result from the presence of a positively charged amino acid, such as Arg or Lys homo-Arg or ornithine, in the +4 position. Alternatively, an amino acid derivative or amino acid mimic having a positive charge in the +4 position can produce the desired effect. In addition, a positively charged chemical moiety which is spatially arrayed so as to occupy substantially such a position can also confer the characteristic. Such a moiety need not be linearly arrayed in the +4 position so long as its positive charge occupies substantially the same spatial site as that occupied by the guanidino side chain 8×, supra.

The peptides of the present invention can be synthesized by any of the suitable methods well known in the art including methods of chemical synthesis. Preferably, the linear sequence is synthesized using commercially available automated peptide synthesizers such as those manufactured by Applied Biosystems, Inc., Foster City, Calif. The material so synthesized can be precipitated and further purified, for example by high performance liquid chromatography (HPLC). Although a purity of greater than 95 percent for the synthesized peptide is preferred, lower purity may be acceptable.

To obtain one of the enhanced peptides of the present invention which have a high potency for inhibiting platelet aggregation and which do not cause prolonged bleeding when administered to an animal, the synthesized peptide is cyclized using methods well known in the art. Cyclization can be achieved where the peptides contain two sulphur-containing amino acids, or other moieties through a disulfide bond. Examples of useful sulphur-containing moieties are Cys and Pen and Pmp. Alternatively, cyclization can be accomplished through the formation of a peptide bond or alkyl bridge structures using, for example, Pas. Where the residues contain sulfhydryls, a disulfide bridge can be formed by oxidizing a dilute aqueous solution of the peptides with $K_3[Fe(CN)_6]$. Other residues, such as the chemical moieties Pmp and Pas, can create a bridging structure through a disulfide bond between Pmp and Cys (or similar structures) and an alkyl bond between Pas and an amino acid methylene moiety (or similar structures). Other means of cyclizing, which are known in the art, can also be utilized.

The cyclized peptides of the present invention can also be prepared by forming a peptide bond between non-adjacent amino acid residues. A procedure for forming such peptide bond is provided in Schiller et al., Int. J. Peptide Protein Res. 25:171 (1985), which is incorporated herein by reference. Briefly, cyclic peptides can be synthesized on the Merrifield resin by assembling the peptide chain using $N^\alpha$-Fmoc-amino acids and Boc and tertiary-butyl protein.

Side-chain to side-chain cyclizations can be performed by the above procedure or using $N^\alpha$-Boc-amino acids together with OFm/Fmoc side-chain protection for Asp and Lys residues as described by Felix et al, Int. J. Peptide Protein Res. 31:231 (1988), which is incorporated herein by reference. Alternatively, side-chain to backbone cyclizations can be performed using this procedure or in combination with the procedure described in the preceeding paragraph.

Alternative methods of making cyclized peptides are disclosed, for example, in WO 91/01331 entitled "SMALL CYCLIC PEPTIDE AGGREGATION INHIBITORS," published 7 Feb. 1991. As described therein, for example, Bromoacetyl-Gly-Arg(g-2,2,5,7,8-pentamethylchroman-β-sulfonyl)-Gly-Asp(beta-t-butyl)-Cys(S-triphenylmethyl)-O-(polymer resin) can be prepared using standard solid phase peptide synthesis utilizing fluorenylmethoxycarbonyl (FMOC) protecting group chemistry on a p-alkoxybenzyl alcohol resin. Repeated treatment of the resin bound peptide with a 1% solution of trifluoroacetic acid in dichloromethane results in cleavage of the S-triphenylmethyl group as evidenced by the bright yellow of the solution. Treatment is continued until dissipation of the yellow color (ca. 1.5 L of the cleavage solution is required per gram of resin bound peptide). After complete cleavage of the S-triphenylmethyl group, the resin bound peptide is washed several times with a 5% solution of N-methylmorpholine in N,N-dimethylacetamide and then shaken in pure N,N-dimethylacetamide for 12 hours to complete the cyclization. Treatment of the cyclized resin bound peptide with trifluoroacetic acid containing (v/v) 1% phenol, 1% anisole and 1% ethanedithiol effects concomitant cleavage of the remaining protective groups and cleavage of the desired product from the resin, which can then be purified, for example by HPLC using a 4.6 mm×250 mm column containing 10 micron, 300 Angstrom pore size C-18 packing. The elution of the column was with an acetonitrile 0.1% aqueous trifluoroacetic acid gradient going from 0%–40% acetonitrile linearly over 80 minutes.

Peptides included in the present invention can contain a hydrophobic moiety adjacent the carboxy terminus of the RGD sequence. The hydrophobic moieties can have a range of structural types and hydrophobicities. Appropriate hydrophobic moieties include for example Phe, Trp, Val, Ile, Leu, p-Cl—F, O—Me—Y, and ChA O-n-hexyl-Y, 3,5-diiodo-Y, Hpa, 2-NapA, O-n-butyl-Y and the like. Such peptides can be represented as $X_1X_2X_3X_4GDX_5X_6X_7$ wherein $X_4$ is a positively charged amino acid; $X_5$ is a hydrophobic moiety; $X_2$ and $X_6$ are moieties capable of forming a bridge, such as a disulfide bridge, alkyl bridge or a peptide bond. Representative of these moieties are Cys, Pen, Pmp, Pmc and Pas. $X_1$ and $X_7$ are 0 to 20 amino acids. When the number of residues of $X_1$ is one, $X_1$ is preferably a Gly; when the number of residues is greater than one, the carboxy terminal residue is preferably a Gly. $X_3$ is 1 to 10 amino acids, preferably with His or Pro as the carboxy terminal residue, a positively charged amino acid, such as Arg or Lys. Specific peptides of this nature include RPenGRGDWPCR (SEQ ID NO:1), GPenGHRGDLRCA (SEQ ID NO:2), RPenGHRGDWRCR (SEQ ID NO:3), RPenGHRGD(ChA)RCR (SEQ ID NO:4), PmpGHRGDLRCA (SEQ ID NO:5), G(dPen)GHRGDLRCA (SEQ ID NO:6), R(Pmc)GHRGDWRCR (SEQ ID NO: 7), R(Pmc)GHRGD(O—Me—Y)RCR (SEQ ID NO: 8), R(Pmc)GHRGDLRCR (SEQ ID NO: 10), R(am-Pmp)GHRGDLRCR, R(Pmc)GHRGDFRCR (SEQ ID NO: 11), R(t-but-Pmc)GHRGDLRCR (SEQ ID NO: 12), Ac-CNPRGD(O—Me—Y)RC—$NH_2$ (SEQ ID NO: 13), Ac-CNPKGD(O—Me—Y)RC—$NH_2$ (SEQ ID NO: 14), Ac-CNPRGD(O-N-Butyl-Y)RC—$NH_2$ (SEQ ID NO: 15).

Alternatively, the peptides can be represented as a composition of matter comprising an —$X_a GDX_b*$— binding site containing cyclic peptide wherein $X_a$ is a positively charged amino acid, $X_b$ is one or more amino acid or other moiety so as to confer platelet aggregation inhibiting activity and wherein * is a positively charged moiety located in appropriate spatial proximity to said binding site so that upon administration of the composition to an animal, bleeding time is not substantially increased over that of an untreated animal.

Peptides having sequences other than those specifically identified herein are also included in the invention provided they exhibit the requisite functional criteria. Peptides which have high anti-thrombotic activity and which do not prolong bleeding time can be synthesized and tested using the teachings described herein. Such peptides once synthesized can be tested for anti-thrombotic activity using, for example, the platelet aggregation assays described in Example V. The relative affinity of the peptide for the various integrin receptors can be tested using, for example, the liposome binding assay of Example IV or the ELISA assays of Example III. Peptides exhibiting high potency for inhibiting platelet aggregation and also showing high affinity for $GPII_b III_a$ and low affinity for the fibronectin and vitronectin receptors should be selected to determine their effect on bleeding time. Animal models such as the baboon models or rabbit models described in Examples VIII and IX can be used to assess bleeding time. After the peptides are administered, the effect can be monitored by cutting the animal and allowing it to bleed onto an absorbent towel or tissue. The length of time until the bleeding stops should be compared to the animals bleeding time without peptide administration. Peptides which fall within the teachings described herein will not increase the bleeding greater than about 2-fold over that of an untreated control. Thus, one skilled in the art can use the teachings of the invention to make and test a variety of peptides having the generic structures described herein.

In another aspect of the invention, peptides are provided that possess relatively high affinity for the receptor IIb/IIIa and low affinity for the fibronectin and vitronectin receptors. Such IIb/IIIa affinity can be determined, as for example, by a liposome attachment assay, as described in Examples IV and VI or in a platelet aggregation assay as described in Example V. Peptides characterized by high affinity for IIb/IIIa will have an $IC_{50}$ as measured under the assay conditions provided in Examples IV and VI of less than about 10 μm, preferably less than about 1 μm, more preferably about 0.1 μm. Alternatively, affinity for IIb/IIIa as characterized in Example V will have an $IC_{50}$ of less than about 10 μm, preferably less than about 1 μm, more preferably about 0.1 μm. Fibronectin receptor affinity and vitronectin receptor affinity can be determined as, for example, by the methods detailed in Examples III and VI, and IV and VI respectively. Using these assays, under the conditions described, peptides having low affinity for the fibronectin receptor will have an $IC_{50}$ of greater than about 0.1 μm, preferably greater than about 1 μm, more preferably greater than about 10 μm; low affinity for the vitronectin receptor is greater than about 1 μm, preferably greater than about 10 μm, more preferably greater than about 100 μm. It is thus possible to screen various peptides in order to determine their inhibitory concentrations, and therefore binding affinities, and to select those having high affinity for the IIb/IIIa and low affinity for the fibronectin and vitronectin receptors.

The invention also provides peptides which differentially inhibit the binding of various ligands to $GPII_b/III_a$, and do not result in a prolongation of bleeding time. For example, the peptide designated herein as 8x inhibits the binding of fibrinogen to GPIIb/IIIa more than it inhibits the binding of van Willebrand factor to the same integrin.

The peptides of the present invention can be utilized to effectively eliminate thrombotic conditions by administering to a mammal exhibiting thrombosis a therapeutically effective amount of the peptide in a suitable physiologically acceptable carrier. Effective amounts will be 1 to 50 mg/kg/hr body weight, preferably about 1 to 5 mg/kg body weight. Appropriate effective amounts can be easily determined by those skilled in the art. The peptide can be administered in a variety of ways, as for example, by infusion or injection. Length of treatment can be determined by monitoring effect.

The claimed subject matter includes a composition of matter comprising a cyclic RGD containing peptide having a hydrophobic moiety adjacent the carboxy terminus of the RGD sequence. In one embodiment, a composition of matter comprising a cyclic peptide having the sequence $X_1 X_2 X_3 X_4 GDX_5 X_6 X_7$ wherein $X_2$ and $X_6$ comprise moieties capable of forming a bridge, $X_3$ is one or more amino acids and $X_1$ and $X_7$ are zero to 20 amino acids and $X_5$ comprises a hydrophobic moiety and $X_4$ is a positively charged amino acid. In another embodiment, a composition of matter comprising an RGD-binding site containing cyclic peptide having platelet aggregation inhibiting activity without substantially prolonging bleeding time. In a further embodiment, a composition of matter comprising an —$X_a GDX_b*$— binding site containing cyclic peptide wherein $X_a$ is a positively charged amino acid, $X_b$ is one or more amino acid or other moiety so as to confer platelet aggregation inhibiting activity and wherein * is a positively charged moiety located in appropriate spatial proximity to said binding site so that upon administration of the composition to an animal, bleeding time is not substantially increased over that of an untreated animal. Other peptides include a peptide selected from the group consisting of:

RPenGRGDWPCR (SEQ ID NO:1)
GPenGHRGDLRCA (SEQ ID NO:2)
RPenGHRGDWRCR (SEQ ID NO:3)
RPenGHRGD(ChA)RCR (SEQ ID NO:4)
PmDGHRGDLRCA (SEQ ID NO:5)
G(dPen)GHRGDLRCA (SEQ ID NO:6)
R(Pmc)GHRGDWRCR (SEQ ID NO: 7)
R(Pmc)GHRGD(O—Me—Y)RCR (SEQ ID NO: 8)
R(Pmc)GHRGD(p-Cl—F)RCR (SEQ ID NO: 9)
R(Pmc)GHRGDLRCR (SEQ ID NO: 10)
R(Pmc)GHGDFRCR (SEQ ID NO: 11)
R(t-but-Pmc)GHRGDLRCR (SEQ ID NO: 12)
Ac-CNPRGD(O—Me—Y)RC—$NH_2$ (SEQ ID NO: 13)
Ac-CNPKGD(O—Me—Y)RC—$NH_2$ (SEQ ID NO: 14)
Ac-CNPRGD(O—N-Butyl-Y)RC—$NH_2$ (SEQ ID NO: 15)

These compositions can be combined with a physiologically acceptable carrier and used to treat thrombosis and vascular graft occlusion.

The following Examples are intended to illustrate but not limit the invention.

EXAMPLE I

Peptide Synthesis

Peptides were synthesized on an automated peptide synthesizer (Model 430A, Applied Biosystems, Foster City, Calif. U.S.A.) using optimized n-methyl pyrrolidone chemistry on PAM resin as recommended by the manufacturer. Cleavage of the peptides from the resin was achieved with 100% hydrogen fluoride. The peptides were further purified by HPLC using a VYDAC reverse phase $C_{18}$ column with 0 to 60% acetonitrile gradients. Peptides were used only if found to be ≤98% pure.

For Pen cyclization, 611 mg of the peptide synthesized as described above were dissolved in 4 liters of water that had been previously boiled and allowed to cool. Immediately prior to addition of the peptide, nitrogen was bubbled through the water for 45 minutes. After the peptide was dissolved, a solution of 0.1 μg/ml of potassium ferrous cyanide $K_3[Fe(CN)_6]$ in water was added dropwise to the stirred peptide solution until the yellow color persisted for 5 minutes (approximately 5 ml). The pH of the solution was held at 7.0 throughout this procedure by addition of $NH_4OH$. The solution was allowed to stand for 20 hours under low vacuum and then lyophilized. Excess $K_3[Fe(CN)_6]$ was removed by passing the cyclized material over a Sephadex G-15 column (1.8×120 cm). The peptide was purified by reverse phase HPLC using a WATERS BONDAPAK $C_{18}$ column (3×30 cm; 10 μm packing) (Waters Assoc., Milford, Mass.). The peptide was loaded on the column in buffer A (20 mM ammonium acetate at pH 7.5) and eluted with a gradient of buffer B consisting of 60% acetonitrile and 40% buffer A. Eluted fractions were tested for their ability to inhibit receptor binding.

The major peak obtained from the $C_{18}$ column constituted 90% of recovered peptide and was deduced to be a monomeric cyclic peptide because it was retained on the column for the length of time predicted for that sequence and because the uncyclized material and multimeric forms were well separated from the main peak.

EXAMPLE II

Receptor and Ligand Purifications

Receptors were purified according to the procedures of Pytela et al. (Methods Enzymol. 144:475 (1987)), incorporated herein by reference. Briefly, vitronectin receptor (Vn-R) was purified by RGD peptide-affinity chromatography from (100 mM) octyl glucoside (OG) extracted human placenta. After extraction, the suspension was filtered over a Sepharose 6B column and then applied to a GRGDSPK column. Except where stated, all procedures were carried out at 4° C. The peptide column was washed with three volumes of Tris-buffered saline (TBS) containing 1 mM $Ca^{2+}$ and 25 mM OG and then with TBS containing 1 mM $Ca^{2+}$ and 25 mM octyl thioglucoside (OTG) at room temperature. Elution of bound receptor was achieved at room temperature with TBS containing 20 mM EDTA and 25 mM OTG. Finally, $Ca^{2+}$ and $Mg^{+2}$ were added to eluted fractions to achieve final concentrations of 1 mM for both ions.

Fibronectin receptor (Fn-R) was similarly purified from (100 mM) octyl glucoside-extracted human placenta using a procedure identical to that for the Vn-R up to and including the initial Sepharose chromatography step. The SEPHAROSE 6B column flow-through was brought to 2 nM $Mn^{+2}$ and the resulting solution was run over a 110 kd fibronectin fragment-affinity column. Washing and elution steps were identical to those used in purifying vitronectin receptor.

Platelet glycoprotein IIb/IIIa was purified from outdated human platelets. Briefly, the platelets were washed 3 times with 10mM tris-HCl, 150 mM NaCl (TBS), 1 mM EDTA, pH 7.5, and centrifuged at 2000×g to pellet cells. Cells were lysed in 5 pellet volumes of TBS, 1% Triton X-100, 1 mM $Ca2Cl_2$, and followed by centrifugation at 30,000×g. The supernatant fraction was collected and the supernatant was loaded onto a concanavalin-A column, previously equilibrated in TBS, 1 mM $Ca2Cl_2$, 0.1% TRITON, 0.05% $NaN_3$ and eluted with 0.2M α-methylmannoside. Fractions were pooled and loaded onto a heparin-agarose column. The flowthrough was collected and concentrated on an Amicon YM 30 filter to a volume of approximately 5–10 ml. The concentrate was then applied to an S-300 column (500 ml) and 6 ml fractions were collected. The $GPII_bIII_a$ containing fractions were collected, pooled and stored at −80° C.

The purification of fibrinogen was conducted essentially as described by Lipinska et al., (J. Lab. Clin. Med. 507 (1974)). Briefly, a 0.3% w/v/ solution of human fibrinogen (Kabi #5302) was dissolved in 150 mM NaCl. Saturated $(NH_4)_2SO_4$ was added dropwise with stirring to the fibrinogen solution to obtain about 16% saturation. The precipitate was spun down in appropriate size bottles at 2000×g. The supernatant was decanted and the precipitate resuspended in 150 mM NaCl (approximately 50% of the original volume). $NH_4SO_4$ was again added dropwise to obtain 16% saturation. The suspension was spun down and the precipitate was resuspended in Tris-saline in a minimal volume (approximately 5% of the original volume). Any remaining insoluble material was spun down at 2000 rpm in a Sorval type centrifuge and the fibrinogen supernatant was decanted and dialyzed overnight at 4° C. against Tris-saline. Characterization of the fibrinogen was by the Bradford protein assay, SDS-PAGE, and/or Western blotting using well known standard procedures.

EXAMPLE III

Enzyme-Linked Immunosorbent Assays (ELISA)

1. Human Vitronectin-Vitronectin Receptor ($α_vβ_3$) ELISA Assay

Human vitronectin (Vn) was isolated from human plasma and purified by affinity chromatography by the method of Yatohgo et al., (Cell Structure and Function 13:281–292 (1988)).

The purity of each receptor was assessed with SDS-PAGE under reducing and non-reducing conditions. Each receptor was flash-frozen in liquid nitrogen and stored frozen until use.

2. Fibronectin Receptor (Fn-R) ELISA Assay

Peptide binding to purified Fn-R was determined by using a competitive enzyme-linked immunosorbent assay (ELISA) in which fibronectin is immobilized and the binding of solubilized Fn-R and the binding of solubilized FN-R, in the presence of various concentrations of peptide analogue, is detected with a polyclonal anti-Fn-R antibody followed by a labelled anti-rabbit IgG conjugate.

Microtiter plates were coated with 110 μl of human fibronectin (at 2 μg/ml) in TBS. The plates were washed three times with TBS that contained 0.05% Tween 20. 50 microliters of receptor in TBS containing 20 mM octylglucoside and 2 mM $NmCl_2$ were added to each well. 50 microliters of peptide in the same buffer were then added in 10-fold serial dilutions. The plates were incubated for three hours at room temperature, washed with 200 μl of the above TBS-Tween buffer. 100 μl of affinity-purified rabbit anti-human fibronectin receptor antibody were added to the wells and the plates were incubated for an additional two hours, washed twice with TBS-Tween and then distilled water. Affinity-purified goat anti-rabbit IgG conjugated to horseradish peroxidase (100 µl) was then added to each well. Bonding reactions were incubated for 16 hours at room temperature. The following day, the plates were washed twice with TBS-TWEEN and then distilled water. 100 µl of substrate mixture (10 mg O-phenylenediamine in 25 ml 0.1M citrate-phosphate buffer, pH 5.0, plus six microliters of 30% $H_2O_2$) were added to the plates and allowed to develop. The development process was stopped by adding 50 µl of 4N $H_2SO_4$ to each well.

3. Fibrinogen—GPIIbIIIa Receptor ELISA (Fg/IIbIIIa)

Microtiter plates, 96 wells were coated (Type Nunc 1 Maxispor™) with 10 µg/ml purified fibrinogen (100 µl/well), and allowed to stand overnight at 4° C. The plates were washed three times with PBS TWEEN, 0.137M NaCl, 0.003M KCl, 0.008M $Na_2HPO_4$, pH 7.4 at room temperature, 0.05% Tween-20 and blocked for 1 to 2 hours at room temperature with 200 µl/well TNCNT (which is 0.5% BSA, 20 mM Tris, pH 7.5 at room temperature, 120 mM NaCl, 0.2% $NaN_3$, 2 mM $CaCl_2$, 0.05% Tween 20, [Calbiochem RIA grade or better]) on a plate shaker. The plates were again washed three times with PBS/TWEEN and 50 µl of sample in TNCNT were added. The mixture was incubated for 15 minutes at room temperature on a plate shaker. The stock solution of purified $GPII_bIII_a$ receptor from human platelets, (0.4–1.0 mg/ml $GPII_bIII_a$ in 0.1% Triton X-100, 1 mM $CaCl_2$, 20 mM Tris, 150 mM NaCl, 0.05% $NaN_3$ in 0.3M N-acetyl glucosamine pH 7.5, stored at −70° C.), was reconstituted in TNCNT. Fifty µl of this diluted $GPII_bIII_a$ were then added to each well and incubated on a plate shaker at room temperature. After one hour, the plates were washed four times with PBS/TWEEN and 100 µl of a polyclonal or monoclonal antibody specific for $GPIII_a$ such as AP3 (1 µg/ml) (See e.g. Newman et al., Blood, 65:227–232 (1985)) and ELISA buffer (PBS, 0.5 BSA, 0.05% TWEEN 20, 0.01% Thimerasol) were added. After one hour incubation at room temperature on a plate shaker, the samples were washed 4 times with PBS/TWEEN. 100 µl of GAMHRP (horse radish peroxidase conjugate of goat anti-mouse IgG (Pel-Freeze Cat. 715305-1) dissolved in ELISA buffer) previously diluted to 1:10,000 were then added and incubated 1 hour at room temperature on a plate shaker. Samples were then washed 4 times with PBS/TWEEN and 100 ml $OPD/H_2O_2$ substrate was added ($OPD/H_2O_2$ substrate: dissolve 10 mg o-phenylenediamine in 15 ml phosphate/citrate buffer, kept at room temperature, in a 50 ml FALCON™ tube covered with foil; just before use, 6.25 µl of 30% $H_2O_2$ is added to give a final solution of 0.67 mg OPD/ml in 0.0125% $H_2O_2$). (The phosphate/citrate buffer consists of 16 mM Citric Acid, 50 mM $Na_2HPO_4$, pH 5.0). The color developed within 3 to 20 minutes and the reaction was stopped with 100 µl 1M $H_2SO_4$. The optical density at 492 nm vs 405 nm was recorded and $IC_{50}$ values were determined.

4. Vitronectin-Vitronectin Receptor ELISA (Vn/VnR)

Anti-$GPII_bIII_a$ monoclonal antibodies specific for human $GPIII_a$ were prepared by the method of Newman et al. (Blood, 65:227–232 (1985)), or a similar procedure. This mouse Mab is specific for the $\beta_3$ subunit of the vitronectin receptor. Rabbit Fab 2 anti-mouse Fc fragment horse radish peroxidase conjugate (anti-MuFc HRP) was obtained from PelFreeze (Cat. No. 715305-1).

Maxisorp microtiter plates were coated with 2 µg/ml human vitronectin dissolved in PBS (50 ml/well) and stored overnight at 4° C. The plates were washed two times with PBS-0.05% TWEEN-20 (wash buffer) and blocked by incubating with about 150 µl/well of assay buffer (1%, BSA (RIA grade or better) in 50 mM Tris-HCl, 100 mM NaCl, 1 mM $MgCl_2$, $CaCl_2$, $MnCl_2$ pH 7.4) for 60 minutes. Dilutions of standards were prepared and putative inhibitors (Table 2) were dissolved in assay buffer. The blocked plates were emptied and 20 µl/well of inhibitor or standard solution were added to each well. Twenty-five µl of a 30 µg/ml solution of purified $\alpha_v\beta_3$ in assay buffer was pipetted into the coated plate. The final concentration of receptor in the assay well was about 15 µg/ml. The plate was incubated on a shaker for 60 minutes. Meanwhile, for each microtiter plate, 6 ml buffer solution containing 1.5 µg/ml of mouse monoclonal antibody specific for $\beta_3$ was prepared. To this solution was added the secondary antibody, which is anti-mouse-Fc-HRP antibody conjugate. For example, for one plate, 6 ml of a 1.5 µg/ml mouse Mab solution was prepared to which was added 1 µl of anti-mouse-Fc-HRP antibody stock, (this represents a 1:6000 dilution of the antibody—HRP conjugate). This mixture was allowed to incubate during the receptor-inhibitor incubation. The assay plates were washed 4 times with PBS-TWEEN and 50 µl/well of the antibody mixture was then pipetted into the plate for a 60 minute incubation. The plate was washed 4 times and the color reaction was developed with 50 µl/well of 0.67 mg/ml o-phenyldiamine in PBS containing 0.012% $H_2O_2$. Alternatively, 16 mM citric acid, 50 mM $Na_2PO_4$ at pH 5.0 can be used as a substrate buffer. The reaction is stopped with 50 µl/well 1M $H_2SO_4$. The plates were read at 492–405 nm and the data analyzed by four-parameters fit.

5. von Willebrand Factor—$GPII_bIII_a$ Receptor ELISA (vWf/$II_bIII_a$)

Microtiter plates were coated with 1.0 µg/ml $GPII_bIII_a$, prepared by the method of Fitzgerald et al., (Anal. Biochem. 151:169–177 (1985)) and allowed to incubate overnight in coat buffer. The plates were then washed three times in wash buffer (0.05% TWEEN 20 in PBS) and 150 µl of assay buffer were added and allowed to incubate for 1–2 hours at room temperature on plate shaker. The plates were washed three times and 50 µl of 2× inhibitor in assay buffer (Assay buffer: 0.5% BSA/50 mM Trix, 100 mM NaCl, 1.0 mM $CaCl_2$, 1.0 mM $MgCl_2$, 1.0 mM $MnCl_2$; coat buffer was the same but without BSA) were added. Fifty µl of 4.0 µg/ml vWF (prepared as described by Ledford et al., Thrombosis and Hemostasis, 64(4):569–575 (1990)) in assay buffer were then added and allowed to incubate for one hour at room temperature on plate-shaker. The plates were washed three times and the antibody mixture was added (1:5000 of mouse anti-vWF and 1:5000 of rabbit-anti-mouse-Fc-HRP, both commercially available) in assay buffer and incubated for 1 hour at room temperature on plate-shaker. Plates were again washed three times and 100 µl of substrate solution (10 mg OPD, 6.5 µl $H_2O_2$, 15 ml phosphate citrate buffer) was added and incubated at room temperature. The color change of $OPD/H_2O_2$ reagent was read at 492 nm with a 405 nm reference wavelength on the filter photometer.

EXAMPLE IV

Liposome Attachment Assay for Vitronectin Receptor (VnR)

This assay was performed with minor modifications, according to the method of Pytela et al., Methods Enzymol. 144:475 (1987), incorporated herein by reference. Briefly, 1:4 mixture of labelled and unlabelled phosphatidylcholine (PC) liposomes was dissolved under nitrogen and diluted with an equal volume of purified receptor (purified as described in Example II) to achieve a fixed predetermined receptor-liposome concentration ratio. This mixture was then dialyzed overnight at 4° C. in phosphate buffered saline (PBS) containing 1 mM Ca$^{2+}$. An aliquot of the dialyzed sample was counted to assess radioactive content; the receptor-liposome mixture was then diluted to obtain a set radioactivity per unit volume.

Microtiter plates were coated with 10 μg of vitronectin. Non-specific sites were blocked for 2 hours at 37° C. in PBS containing 5 mg/ml BSA and 1 mM each of CaCl$_2$ and MgCl$_2$. The plates were then rinsed twice with PBS containing 1 mM Ca$^{+2}$ and Mg$^{+2}$, and 100 μl of the liposome-receptor mixture was added to each well. If necessary, peptides were added before this step in a 1–10% dilution. The plates were then incubated at 4° C. for 24 hours. The following day, the liquid in each well was aspirated and the plates were washed twice with PBS containing 1 mM Ca$^{+2}$ and Mg$^{+2}$. Finally, 100 μl of 2% SDS was added, the plates were shaken for 10–15 minutes, and the supernatants were collected, vortexed, and subjected to liquid scintillation counting. This procedure typically yielded ca. 1000 total and 100 non-specific counts per well.

EXAMPLE V

Platelet Aggregation and Potencies of Hydrophobically Enhanced RGD Peptides

Platelet aggregation was assessed using the method of Born, Nature 194:927–929 (1962), incorporated herein by reference. Briefly, the change in light transmission was measured through a stirred suspension of platelets in an aggregometer (Model 400 VS, Chrono-Log, Havertown, Pa., U.S.A.). Studies employing ADP were performed with platelet-rich plasma (PRP), which was obtained by low-speed centrifugation (200×g for 10 min.) of whole blood freshly drawn into trisodium citrate (at a final concentration of 11 mM). In studies using thrombin, the PRP was gel-filtered on Sepharose 2B in divalent ion-free Tyrode's solution containing 2% BSA. For all studies, the reference standard was platelet-poor plasma, which was obtained by centrifuging PRP at 1000×g for 5 min.

All aggregation studies were performed at 37° C. with a constantly stirred suspension of 3×10$^8$ platelets/ml. (Platelet count was determined with the aid of a hemacytometer.) Peptides and stimulants were added to these suspensions in 1% dilutions. The PRP and gel-filtered platelets were used within three hours from the time of blood collection.

Peptide anti-aggregation potencies were determined from dose-responsive curves for the inhibition of the maximum aggregation responses stimulated by physiologic doses of ADP (10 μm) and thrombin (2 U/ml). The 50% inhibitory concentration of each peptide (IC$_{50}$) was determined by regression analysis of these curves.

In an independent study, a slightly modified aggregation assay was used. The modified method was as follows and the results are shown in Table II. Platelet aggregation assays were performed in human platelet rich plasma (PRP). Fifty milliliters of whole human blood (9 parts) was drawn on 3.6% sodium citrate (1 part) from a donor who had not taken aspirin or related medications for at least two weeks. The blood was centrifuged at 160×g for 10 minutes at 22° C. and allowed to stand for 5 minutes after which the PRP was decanted. Platelet poor plasma (PPP) was isolated from the remaining blood after centrifugation at 2000×g for 25 minutes. The platelet count of the PRP was diluted to about 300,000 platelets per microliter with PPP.

A 225 μl aliquot of PRP plus 25 μl of either a dilution of the test inhibitor sample or a control (PBS) was incubated for 5 minutes in a Chrono-log Whole Blood Aggregometer at 37° C. An aggregating agent (collagen, 1 μg/ml; U46619, 100 ng/ml; or ADP, 17 μM) was added and the transmission was recorded.

The hydrophobically enhanced RGD peptides have been grouped into four distinguishable classes for systematic comparison. They are (1) cyclic RGD peptides which vary the size and hydrophobicity of the moiety at the position immediately following the Asp residue in the tripeptide RGD (the first and last position as depicted in Table I may vary by substitution with Arg); (2) cyclic RGD peptides which vary the size and hydrophobicity of the bridging structure for cyclization; (3) cyclic RGD peptides which vary the size and hydrophobicity of both the bridging structure and the residue immediately following the Asp residue in the tripeptide RGD and (4) cyclic RGD peptides which fall into one of the above three classes and also vary the charge at the residue adjacent to the hydrophobic moiety. Other RGD peptides, both linear and cyclized, are included in Table I for comparison. Underlining indicates a bridge between the first and last residue included in the underlined portion.

As shown in Table I, each class of cyclized, hydrophobically enhanced RGD peptide analogue demonstrated inhibitory effects on platelets stimulated with thrombin or ADP. Eight analogues had inhibitory potencies (IC$_{50}$) less than or approximately equal to 10 μm against thrombin-stimulated platelet aggregation while as many as twenty-two demonstrated inhibitory potencies in this range for the ADP-stimulated response. For example, the inclusion of hydrophobic residues phenylalanine (F) and tryptophan (W) in the "X" position of template structures GPenGRGD-X-PCA (SEQ ID NO:16) and GPenGHRGD-X-RCA (SEQ ID NO:17) imparted greater anti-aggregation inhibitory potency relative to GPenGRGDSPCA (SEQ ID NO:18) and GPenGHRGDLRCA (SEQ ID NO:2). This effect was further enhanced by other non-natural hydrophobic structures, such as para-chloro-phenylalanine p-Cl—F, and O-methyl-tyrosine (O—Me—Y) O-n-hexyl-tyrosine, 3,5-diiodo-tryosine, O-n-butyl-tyrosine, p-nitro-phenylalanine p-nitro-F and the like in the same position. The inclusion of positively charged moieties such as arginine (R) or lysine (L) in the "X" positions of XPen-GRGDSPCA (SEQ ID NO: 19) or X-PenGHRGDLRCA (SEQ ID NO:20) also increased anti-aggregation potency. Moreover, the inclusion of a positively charged moiety outside the cyclic structure also yielded peptides with high potency.

Organic mimic bridging structures were substituted for penicillamine and Pmp in the "X" position of the template structure G-X-GHRGDLRCA (SEQ ID NO:21). When substituted alone, tert-butyl-Pmp and amino-Pmp lessened peptide anti-aggregation potency. On the other hand, peptide derivatives containing these moieties and an N-terminal R significantly out-performed the previously disclosed cyclic RGD structures GPenGHRGDLRCA (SEQ ID NO:2) and PmpDGHRGDLRCA (SEQ ID NO:5), in platelet aggregation assays. Finally, replacement of 1-Pen in G(1-Pen)GH-RGDLRCA (SEQ ID NO:22) by the d-form of penicillamine lowered anti-aggregation potency by 2-fold.

The modifications described above have resulted in inhibitory potencies 10 to 250-fold more potent than the prototype GRGDSP linear peptide and 2 to 5-fold more potent than the initial conformationally restrained cyclic peptide GPenGRGDSPCA. The results from the independent study, shown in Table II, further corroborate these conclusions.

TABLE I

Potencies of Hydrophobically Enhanced RGD Peptide Analogs Against Platelet Aggregation and Receptor Binding

| Peptide | Thrombin Stimulated Aggregation | ADP-Stimulated Aggregation | FnR Binding | VnR Binding | IIb/IIIa Binding |
|---|---|---|---|---|---|
| GRGDSP[23] | | 135 ± 15 | 0.032 ± 0.006(4)* | 0.70 | 50 |
| GPenGRGDSPCA[18] | | 27.5 | 0.015 | 0.15 | 0.29 |
| GPenGRGDTPCA[24] | 28 | 22.3 | .063 | 0.033 | |
| GPenGRGDLPCA[25] | | 19.3 | 0.96 | 0.073 | |
| GPenGRGDFPCA[26] | | 3.5 | .084 | 2.7 | 4.1 |
| GPenGRGDWPCA[27] | | 1.6 | 0.13 | 12.7 | |
| RPenGRGDWPCR[28] | 0.53 | 0.65 | 0.014 | 4.2 | 0.098 |
| GPenGHRGDLRCA[2] | 18 | 15 | 10 | 1.2 | 10 |
| RPenGHRGDLRCR[29] | 3.2 | 10.3 | 5.9 | 37.1 | 6.2 |
| RPenGHRGDWRCR[3] | 1.2 | 1.3 | 7.3 | 6.9 | 0.80 |
| RPenGHRGD(ChA)RCR[4] | | 4.1 | 3.9 | 10 | |
| RPenGHRGD(1-napA)RCR[30] | | 29 | 10 | | |
| PmpGHRGDLRCA[5] | 6.3 | 7.2 | 0.34 | 10 | |
| G(Pmc)GHRGDLRCA[31] | | 83 ± 23(2) | 3.4 | | |
| (t-but-Pmp)GHRGDLRCA[32] | | 120 | 1.1 | | |
| (t-but-Pmc)GHRGDLRPenA[33] | | 89 | | | |
| G(dPen)GHRGDLRCA[6] | | 6.28 ± 0.7(2) | 1.5 | 5.3 | 1.4 |

[2] = SEQ ID NO: 2; [3] = SEQ ID NO: 3; [4] = SEQ ID NO: 4; [5] = SEQ ID NO: 5; [6] = SEQ ID NO: 6; [18] = SEQ ID NO: 18; [23] = SEQ ID NO: 23; [24] = SEQ ID NO: 24; [25] = SEQ ID NO: 25; [26] = SEQ ID NO: 26; [27] = SEQ ID NO: 27; [28] = SEQ ID NO: 28; [29] = SEQ ID NO: 29; [30] = SEQ ID NO: 30; [31] = SEQ ID NO: 31; [32] = SEQ ID NO: 32; [33] = SEQ ID NO: 33

| Peptide | Thrombin Stimulated Aggregation | ADP-Stimulated Aggregation | FnR Binding | VnR Binding | IIb/IIIa Binding |
|---|---|---|---|---|---|
| R(Pmc)GHRGDWRCR-1[7] | | 1.4 | 1.7 | 5.9 | 0.06 |
| R(Pmc)GHRGDWRCR-2a,[7] | | 1.4 | 1.7 | | |
| R(Pmc)GHRGD(O—Me—Y)RCR[8] | | 0.45 | 2.1 | 1.0 | 0.018 |
| R(Pmc)GHRGD(p-Cl—F)RCR) | | 0.65 | 1.2 | 10 | 0.02 |
| R(Pmc)RGD(ChA)CR)[34] | | <200* | 0.35 | | |
| R(Pmc)GHRGDLRCR-1[10] | 1.3 | 1.5 | 1.1 | 6.7 | 0.4 |
| R(Pmc)GHRGDLRCR-2a,[10] | 1.3 | 1.5 | 2.9 | | |
| R(t-but-Pmc)GHRGDLRCR-1[12] | | 1.9 | 2.2 | | |
| R(t-but-Pmc)GHRGDLRCR-2a,[12] | | 1.9 | 2.2 | 3.7 | 0.06 |
| R(Pmc)GRGDWPCR[35] | | 1.2 | 0.05 | 0.84 | 0.025 |
| R(Pmc)GHRGD(O-n-hexyl-Y)RCR[36] | | 0.96 | 2.0 | | |
| R(Pmc)GHRGD(3,5-diiodo-Y)RCR[37] | | 1.10 | 6.1 | 0.9 | 0.013 |
| R(Pmc)GHRGD(Hpa)RCR[38] | | 1.15 | 1.81 | 4.2 | 0.02 |
| R(Pmc)GHRGD(2-NapA)RCR[39] | | 1.60 | 4.2 | 10 | 0.06 |
| R(Pmc)GHRGD(O-n-butyl-Y)RCR[40] | | 0.35 | 6.60 | 2.20 | 0.028 |
| R(Pmc)GHRGD(p-nitro-F)RCR[41] | | 0.38 | 5.74 | 6.05 | 0.023 |
| R(Pmc)GHRGDVRCR[42] | | 0.69 | 2.30 | 2.00 | 0.15 |
| R(Pmc)GHRGDFRCR[43] | | 0.62 | 8.70 | 10.00 | 0.043 |
| R(Pmc)GHRGDYRCR[44] | | 1.00 | 10.00 | 7.85 | 0.153 |
| R(Pmc)RHRGD(O—Me—Y)RCR[45] | | 0.44 | 7.72 | 6.20 | 0.068 |
| R(Pmc)GHRGD(Phg)RCR[46] | | 0.68 | 1.23 | 0.79 | 0.023 |
| R(Pmc)GHRGD(O—Me—Y)RCR[8] | | 0.83 | 6.40 | 9.90 | 0.06 |
| F(Pmc)GHRGD(O—Me—Y)RCR[47] | | 0.73 | 8.70 | 6.04 | 0.07 |
| R(dPen)GHRGD(p-iodo-F)RCR[48] | | 0.78 | 4.37 | 10.00 | 0.023 |
| K(Pmc)GHRGD(O—Me—Y)RCK[49] | | 0.83 | 8.60 | 3.90 | 0.029 |
| R(Pmc)GHRGD(O—Me—Y)OCR[50] | | 0.91 | 8.40 | 9.30 | 0.007 |
| H(Pmc)GHRGD(O—Me—Y)RCR[51] | | 0.94 | 8.30 | 8.40 | 0.079 |
| R(Pmc)GHRGD(p-amino-F)RCR[52] | | 0.99 | 9.01 | 10.00 | 0.34 |
| R(Pmc)NHRGD(O—Me—Y)RCR[53] | | 0.99 | 4.70 | 6.90 | 0.098 |
| G(Pmc)GHRGD(O—Me—Y)RCR[54] | | 1.10 | 10.00 | 10.00 | 0.104 |

[7] = SEQ ID NO: 7; [8] = SEQ ID NO: 8; [9] = SEQ ID NO: 9; [10] = SEQ ID NO: 10; [12] = SEQ ID NO: 12; [35] = SEQ ID NO: 35; [36] = SEQ ID NO: 36; [37] = SEQ ID NO: 37; [38] = SEQ ID NO: 38; [39] = SEQ ID NO: 39; [40] = SEQ ID NO: 40; [41] = SEQ ID NO: 41; [42] = SEQ ID NO: 42; [43] = SEQ ID NO: 43; [44] = SEQ ID NO: 44; [45] = SEQ ID NO: 45; [46] = SEQ ID NO: 46; [47] = SEQ ID NO: 47; [48] = SEQ ID NO: 48; [49] = SEQ ID NO: 49; [50] = SEQ ID NO: 50; [51] = SEQ ID NO: 51; [52] = SEQ ID NO: 52; [53] = SEQ ID NO: 53; [54] = SEQ ID NO: 54

| Peptide | Thrombin Stimulated Aggregation | ADP-Stimulated Aggregation | FnR Binding | VnR Binding | IIb/IIIa Binding |
|---|---|---|---|---|---|
| R(Pmc)GHRGD(O—Me—Y)KCR[55] | | 1.10 | 10.00 | 10.00 | 0.047 |
| GPenIARGDWNCA[56] | | 1.20 | 0.71 | 0.041 | 0.01 |
| T(Pmc)GHRGD(O—Me—Y)RCR[57] | | 1.25 | 10.00 | 10.00 | 0.052 |
| R(Pmc)GHRGD(p-nitro-F)KCR[58] | | 1.40 | 3.10 | 10.00 | 0.10 |
| R(Pmc)GHRGD(p-iodo-F)KCR[59] | | 1.50 | 5.50 | 8.00 | 0.063 |
| Ac—(Pmc)GHRGD(O—Me—Y)RC—NH$_2$[60] | | 1.61 | 9.70 | 10.00 | 0.40 |
| D(Pmc)GHRGD(O—Me—Y)RCR[61] | | 1.75 | 10.00 | 8.85 | 0.22 |
| Ac—CIPRGD(O—Me—Y)RC—NH$_2$[62] | | 0.17 | 4.28 | 5.75 | 0.003 |
| Ac—CNPRGD(O—Me—Y)RC—NH$_2$[13] | | 0.22 | 8.20 | 4.70 | 0.029 |
| Ac—(dPen)IPRGD(O—Me—Y)RC—NH$_2$[63] | | 0.28 | 4.31 | 4.32 | 0.0023 |
| Ac—(dPen)NPRGD(O—Me—Y)RC—NH$_2$[64] | | 0.17 | 6.75 | 6.71 | 0.0010 |
| Ac—CNPRGD(O-n-butyl-Y)RC—NH$_2$[15] | | 0.10 | 1.53 | 10.00 | 0.006 |
| R(dPen)NPRGD(O—Me—Y)RCR[65] | | 0.12 | 10.00 | | 0.0012 |
| GRGDSPDG[66] | | 32 | 0.05 | 0.10 | 0.25 |
| FRGDSPDG[67] | | 110 | 2.4 | 0.04 | |
| YRGDSPDG[68] | | 83 | 1.1 | 0.08 | |
| LRGDSPDG[69] | | 150 | 1.2 | 0.2 | |
| dSRGDSPDG[70] | | 54 | .075 | 0.07 | |

TABLE I-continued

Potencies of Hydrophobically Enhanced RGD Peptide Analogs Against Platelet Aggregation and Receptor Binding

| Peptide | Thrombin Stimulated Aggregation | ADP-Stimulated Aggregation | FnR Binding | VnR Binding | IIb/IIIa Binding |
|---|---|---|---|---|---|
| VRGDSPDG[71] | | 92 | 0.04 | 0.24 | 0.27 |
| GPenGRGDRPCA[72] | | 22.3 | 1.3 | 0.47 | |
| GPenLRGDTPCA[73] | | 86 | 1.9 | 0.25 | |
| GPenVRGDSPCA[74] | | 45 | | | |
| GPenYRGDSPCA[75] | | 47 | | | |
| GPenLRGDSPCA[76] | 308 | 415 | 0.54 | 0.26 | 0.48 |
| GPenLRGDSRCA[77] | 49 | 41 | 1.1 | 1.35 | |
| GPenGRGDSFCA[78] | | 115 | | 0.02 | |
| GPenFRGDSFCA[79] | | >200 | 0.33 | 0.05 | 3.4 |
| GPenGRGDTPCR[80] | | 22.0 | 0.26 | 0.01 | |
| RPenGRGDTPCA[81] | 3.1 | 7.0 | 0.08 | 0.03 | |

[13] = SEQ ID NO: 13; [15] = SEQ ID NO: 15; [55] = SEQ ID NO: 55; [56] = SEQ ID NO: 56; [57] = SEQ ID NO: 57; [58] = SEQ ID NO: 58; [59] = SEQ ID NO: 59; [60] = SEQ ID NO: 60; [61] = SEQ ID NO: 61; [62] = SEQ ID NO: 62; [63] = SEQ ID NO: 63; [64] = SEQ ID NO: 64; [65] = SEQ ID NO: 65; [66] = SEQ ID NO: 66; [67] = SEQ ID NO: 67; [68] = SEQ ID NO: 68; [69] = SEQ ID NO: 69; [70] = SEQ ID NO: 70; [71] = SEQ ID NO: 71; [72] = SEQ ID NO: 72; [73] = SEQ ID NO: 73; [74] = SEQ ID NO: 74; [75] = SEQ ID NO: 75; [76] = SEQ ID NO: 76; [77] = SEQ ID NO: 77; [78] = SEQ ID NO: 78; [79] = SEQ ID NO: 79; [80] = SEQ ID NO: 80; [81] = SEQ ID NO: 81

| Peptide | Thrombin Stimulated Aggregation | ADP-Stimulated Aggregation | FnR Binding | VnR Binding | IIb/IIIa Binding |
|---|---|---|---|---|---|
| KPenGRGDTPCA[82] | | 10.3 | 0.03 | 0.015 | |
| RPenGRGDTPCR[83] | 2.0 | 6.3 | .027 | 0.01 | |
| RPenGRGDTPCK[84] | | 7.6 | 0.49 | | |
| RPenGRGDSRCA[85] | 12 | 12 | | | |
| RPenGRGDLRCA[86] | 13 | 16 | | | |
| GPenGHRGDTRCA[87] | 17 | 11.3 | 2.9 | | |
| R₂PenGRGDTPCA[88] | 2.7 | 8.2 | | | |
| RPenGHRGDTRCR[89] | | 8.8 | | | |
| LPenGHRGDLRCA[90] | | 10.5 | 4.9 | | |
| PmpGRGDSPCA[91] | | 45 | .023 | 0.10 | 0.58 |
| PmpGRGDTPCA[92] | | 85 | .086 | 0.05 | |
| PmpGHRGDLRPenA[93] | | 5.8 | .078 | 5.2 | 0.55 |
| (t-butyl-Pmc)GHRGDLRCA[94] | | 130 | 1.5 | | |
| R(Pmc)GRGDTPCA[95] | | | 0.03 | | |
| GHRGDLRDASG[96] | | 7.5 | 4.9 | | |
| RKGHRGDLRDR[97] | | 75 | 1.3 | | |
| R(orn)GHRGDLRDRASG[98] | | 24 | 22 | | |
| R(orn)GHRGDLRDR[99] | | >200 | | | |
| R(orn)GHRGDLRER[100] | | 44 | 1.7 | | |
| GHRGDLRPasA—NH₂[101] | | 4.8 | 3.2 | | |
| R₅GDS[102] | | 28 | 0.64 | | |

*concentrations unconfirmed by amino acid composition analysis
ᵃRepresents second peak after HPLC purification of synthesized peptides using a racemic am-Pmp mixture.

[82] = SEQ ID NO: 82; [83] = SEQ ID NO: 83; [84] = SEQ ID NO: 84; [85] = SEQ ID NO: 85; [86] = SEQ ID NO: 86; [87] = SEQ ID NO: 87; [88] = SEQ ID NO: 88; [89] = SEQ ID NO: 89; [90] = SEQ ID NO: 90; [91] = SEQ ID NO: 91; [92] = SEQ ID NO: 92; [93] = SEQ ID NO: 93; [94] = SEQ ID NO: 94; [95] = SEQ ID NO: 95; [96] = SEQ ID NO: 96; [97] = SEQ ID NO: 97; [98] = SEQ ID NO: 98; [99] = SEQ ID NO: 99; [100] = SEQ ID NO: 100; [101] = SEQ ID NO: 101; [102] = SEQ ID NO: 102

TABLE II

In Vitro Integrin ELISA Results

| Code | IC50 (μM) Human Platelet Aggregation | IC50 (nM) Fg/II$_b$III$_a$ | Vn/VnR | vWF/II$_b$III$_a$ | Fn/FnR | Sequence |
|---|---|---|---|---|---|---|
| 8X | 0.22 | 8.7 | 4700 | 14.8 | 8200 | Ac—CNPRGD(O—Me—Y)RC—NH₂[13] |
| 11J | 3.4 | 17.3 | 48 | 6.4 | 6200 | Ac—CNPRGD(O—Me—Y)EC—NH₂[103] |
| 11K | 4.5 | 36 | 30 | 9.3 | 840 | Ac—CNPRGD(O—Me—Y)AC—NH₂[104] |
| 11L | 7.3 | 932 | 1818 | 640 | >10000 | Ac—CNPRGD(O—Me—Y)(dR)C—NH₂[105] |
| 11P | 4.9 | 44.5 | 63.5 | 9.9 | 440 | Ac—CNPRGD(O—Me—Y)OC—NH₂[106] |
| 11Q | 0.79 | 55 | 20000 | 60.2 | 5600 | Ac—CNPKGD(O—Me—Y)RC—NH₂[14] |
| 11R | 1.0 | 96 | 705 | 89.9 | 1560 | Ac—CNPRGD(O—Me—Y)KC—NH₂[107] |
| 11S | 7.3 | 102 | 891 | 27.1 | 440 | Ac—CNPRGD(O—Me—Y)(Cit)C—NH₂[108] |
| 11V | 7.6 | 15.2 | 108 | 18.6 | (not tested) | Ac—CNPRGD(O—Me—Y)(Nle)C—NH₂[109] |
| 2G | 14 | | | | | GPenGHRGDLRCA[2] |
| 2H | 20 | | | | | GRGDSPDG[65] |
| 4Q | 3.3 | | 86.6 | | | RPenGHRGDWRCR[3] |
| 5Q | 0.56 | | 15.7 | | | R(Pmc)GHRGD(O—Me—Y)RCR[8] |
| 6Z | 58 | | | | | GPenRARGDNPCA[110] |
| 7B | 0.70 | | 11.8 | | | RPmcGHRGD(p-iodo-F)RCR[111] |

TABLE II-continued

In Vitro Integrin ELISA Results

| | IC50 (μM) Human Platelet | IC50 (nM) | | | | |
|---|---|---|---|---|---|---|
| Code | Aggregation | Fg/II$_b$III$_a$ | Vn/VnR | vWF/II$_b$III$_a$ | Fn/FnR | Sequence |
| 7T | 0.38 | | | 29 | | RPmcGHRGD(p-nitro-F)RCR[112] |
| 10R | 0.17 | | | | | Ac—CIPRGD(O—Me—Y)RC—NH$_2$[113] |
| 10X | 0.17 | | | | | Ac—(dPen)NPRGD(O—Me—Y)RC—NH$_2$[114] |

[2] = SEQ ID NO: 2; [3] = SEQ ID NO: 3; [8] = SEQ ID NO: 8; [13] = SEQ ID NO: 13; [14] = SEQ ID NO: 14; [65] = SEQ ID NO: 65; [103] = SEQ ID NO: 103; [104] = SEQ ID NO: 104; [105] = SEQ ID NO: 105; [106] = SEQ ID NO: 106; [107] = SEQ ID NO: 107; [108] = SEQ ID NO: 108; [109] = SEQ ID NO: 109; [110] = SEQ ID NO: 110; [111] = SEQ ID NO: 111; [112] = SEQ ID NO: 112; [113] = SEQ ID NO: 113; [114] = SEQ ID NO: 114

EXAMPLE VI

Peptide Receptor Selectivity

In parallel studies with the platelet aggregation experiments (described in Example V), the apparent affinities of peptides for GP IIb/IIIa, fibronectin and vitronectin receptors were determined. Receptor-binding assays (as described in Examples III and IV) with purified receptors, were used to assess the abilities of the peptides to displace the binding of receptors to their receptor-specific ligands.

Shown in Table I, as a comparison with platelet inhibitory potencies, are the relative affinities of each peptide for the receptors shown.

The binding data are again represented as the 50% inhibitory concentration of each peptide (IC$_{50}$s) and were determined as described in Example V for the dose-response curves for the inhibition of platelet aggregation. IC$_{50}$s for FnR were determined by ELISA (Example III). Those for VnR and GP IIb/IIIa were determined either by ELISA or liposome attachment assay (Example IV). The GRGDSP prototype peptide is used as a reference for comparison between assays for an individual peptide.

Table II provides the receptor binding data as a comparison with the platelet inhibitory potencies shown therein. This data is also represented as the 50% inhibitory concentration of each peptide. The values for all receptor assays were determined by ELISA as described in Example III. The results shown in Table II further corroborate the conclusions drawn from Table I, namely, that the anti-aggregation potencies are parallel by their relative affinity for the IIb/IIIa receptor.

EXAMPLE VII

Efficacy Against Electrically Induced Canine Coronary Thrombosis

1. Surgical Preparation and Instrumentation

Male mongrel dogs weighing 14 to 20 kg were selected based on proper aggregation of their platelets in response to arachidonic acid, collagen, and adenosine disphosphate (ADP) and based on similar weights and hemodynamic properties.

Before surgery, the animals were anesthetized with sodium pentobarbital (30 mg/kg, i.v.) and then intubated and ventilated on room air with positive pressure using a respirator (Harvard Apparatus, S. Natick, Mass.) at a volume of 30 ml/kg and a frequency of 12 breaths/min. Surgery, performed under aseptic conditions, was begun with the placement of cannulae into the left carotid artery and jugular vein for monitoring arterial blood pressure (Statham P23 pressure transducer, Gould, Inc., Cardiovascular Products, Oxnard, Calif.) and administering intravenous fluids.

Figure 1B:
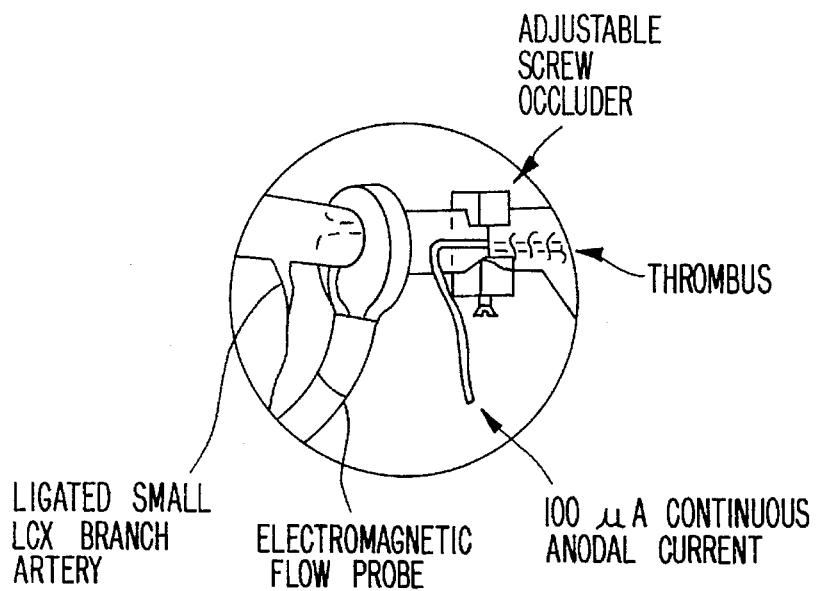
Figure 1C:
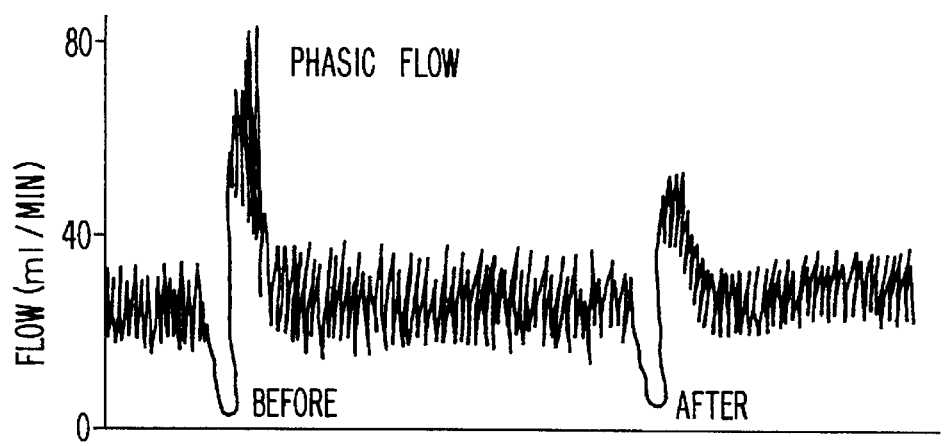

The heart was exposed via a left thoracotomy through the 5th intercostal space. A 2-cm segment of the left circumflex coronary artery (LCCA) was isolated from surrounding tissue by blunt dissection. This artery was instrumented from proximal to distal with an electromagnetic flow probe (Model 501, Carolina Medical Electronics, Inc., King, N.C.), intra-coronary electrode, and screw occluder (see FIGS. 1a and 1b). The intra-coronary electrode was constructed by attaching a 25-gauge hypodermic needle tip to a 30-gauge TEFLON-insulated silver-coated copper wire. The mechanical occluder was constructed of stainless steel in a C shape with a Teflon screw (2 mm diameter) on top. It was adjusted to control vessel circumference and decrease the reactive hyperemic flow due to a 10-sec (full) occlusion by 50–70% without affecting basal coronary blood flow (FIG. 1c). A monopolar epicardial electrode was sutured to the surface of the ventricle in the region of LCCA distribution to monitor ischemic changes in the electrocardiogram (ECG). The left atrium was cannulated with polyethylene tubing for administration of the peptide. Continuous recordings of blood pressure, limb lead II ECG, epicardial electrogram, and mean and phasic LCCA blood flow were obtained on a Model 7 polygraph (Grass Instrument Co., Quincy, Mass.).

2. Induction of coronary thrombosis

One hour after the completion of surgery, a 100 microamp continuous anodal direct current delivered from a 9 volt nickel-cadmium battery was applied to the intimal surface of the LCCA. The anode of the battery was in series with a 250,000 ohm potentiometer and the intraluminal coronary artery electrode. The electric circuit was completed by placing the cathode in a subcutaneous site. Electrical stimulation was applied for three hours. At the conclusion of each experiment, the heart was fibrillated electrically and quickly removed, and the LCCA was dissected free as far as possible to verify the position of the implanted anodal electrode.

For all ex vivo studies (see FIG. 3), control aggregation values were standardized to the percentages of light transmission observed in PRP and PPP samples (0% and 100%, respectively).

3. Peptide Administration

Animals were randomly assigned to two treatment groups: vehicle control (i.e., normal saline) or RGD peptides at various concentrations. Peptides were administered intra-atrially in both bolus and continuous injections. Each bolus injection consisted of 0.5 to 10 mg/kg and was administered 15 minutes before application of the current. A continuous infusion of the same peptide was then started immediately after completion of this initial injection. Animals received a 25 μg/kg/min to 200 μg/kg/min infusion. The anti-thrombotic effects of the peptides were monitored until 30 minutes after the occurrence of a persistent, occlusive thrombus or five hours after the initiation of electrical stimulation (whichever resulted first). If an occlusive thrombus had not developed within four hours after the initiation of current, the peptide infusion was stopped.

4. Platelet Studies

Platelet counts and ex vivo aggregation studies were performed one hour before and 1, 3, and 5 hours after application of anodal direct current. Samples of arterial blood were drawn into plastic syringes containing 3.8% trisodium citrate (giving a 1:10 final dilution) and platelet aggregation determined as described in Example V.

Figure 2A:
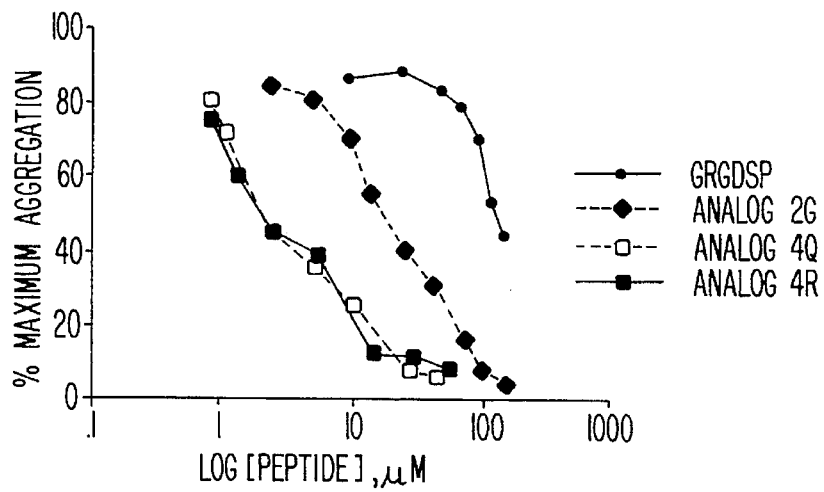
FIGS. 2a, 2b and 2c are dose-response analysis of the relative anti-aggregation potencies of the peptides injected in Example VII.
Figure 2B:
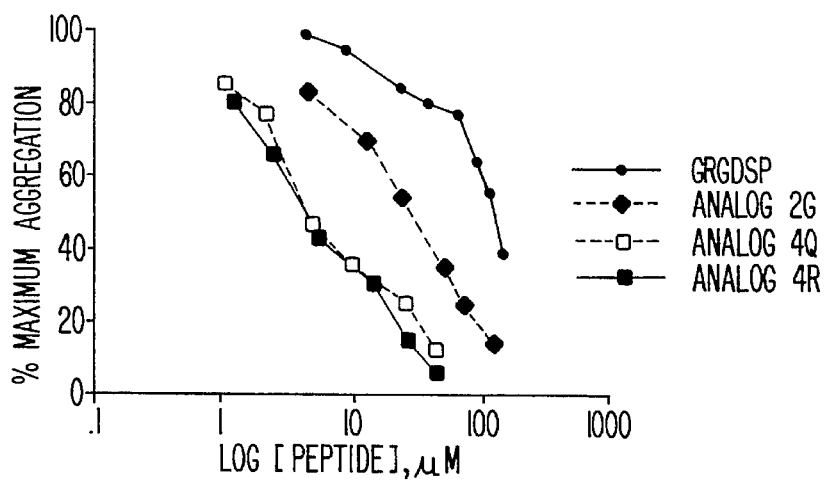
Figure 2C:
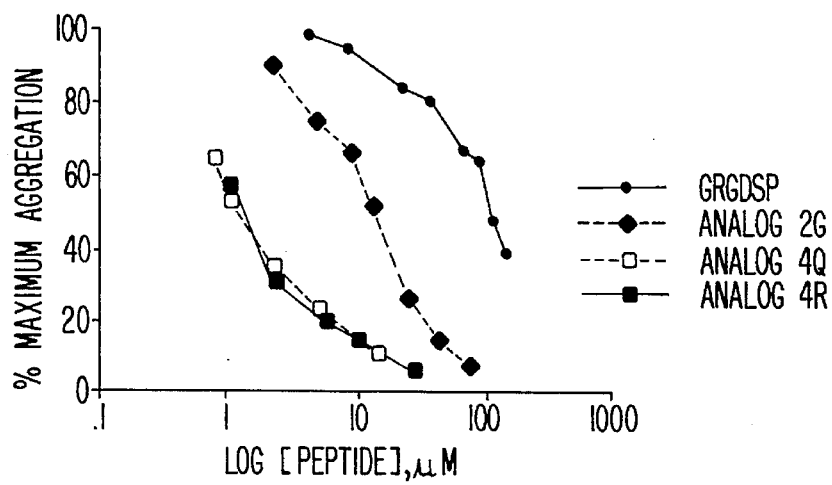

The inhibitory potencies of peptide analogues 2 G (GPenGHRGDLRCA), 4Q (RPenGHRGDWRCR), and 4R (RPenGRGDWPCR), as well as the generic analogue GRGDSP, were determined against canine platelet aggregation stimulated maximally by 10 μm ADP, 0.65 mM arachidonic acid (AA), or 9.6 micrograms/ml collagen. Epinephrine (550 nM) was used to prime platelets before stimulation with arachidonic acid. Peptides were added in 1% dilutions to the PRP solutions. The relative anti-aggregation potencies of all injected peptides and the generic analog GRGDSP were determined at the 1 hour before current time point, with dose-response analysis (see FIGS. 2a, 2b and 2c). The peptide concentrations causing 50% inhibition of maximal activation ($IC_{50}$s) were derived by linear regression of these dose-response curves. For computation of these inhibitory potencies, control values (i.e., in the absence of peptide) were considered as 100% of maximum.

As shown, analogues 4Q and 4R exhibited superior potencies, inhibiting aggregation by 50% at 1.5–5 μm. Analogue 2G was slightly less potent, with $IC_{50}$s of 15–30 μm, whereas GRGDSP inhibited all three responses by 50% at ca. 130 micromolar. Notably, the potency order (4Q=4R>2G>GRGDSP) and $IC_{50}$s of these peptides against these responses were the same as those observed for their inhibition of ADP-, collagen-, and arachidonic acid-stimulated aggregation of human platelets.

Platelet aggregation was also determined ex vivo at one, three, and five hours after current application. For these studies, arachidonic acid, or collagen was again used to stimulate the platelets.

The average aggregation values determined in these studies for all of the peptide treatments are depicted in FIGS. 3a, 3b1, 3b2, 3b3, 3c1 and 3c2. (In these histograms, 0% and 100% aggregation represent the extent of light transmission through PRP and PPP, respectively, before the addition of stimulant.) Analogue 2G, when injected at 10 mg/kg, substantially inhibited ADP-stimulated aggregation but only partially inhibited the AA- and collagen-stimulated responses (43–70% and 12–50%, respectively, relative to control levels) at all three time points (FIG. 3a). As shown in FIGS. 3b1 3b2 and 3b3, 3c1 and 3c2 the ex vivo anti-aggregation effects of analogues 4Q and 4R were far superior. A 5 mg/kg injection of analogue 4Q made the platelets completely unresponsive to stimulation with ADP and AA at all three time points and caused near-maximal inhibition of their activation by collagen. (Here, the absence of a coded bar indicates the absence of the corresponding response.) As shown in FIG. 3b, the effects of this same peptide at the same injection were more pronounced when platelet count was low, i.e., ca. one-third of normal (104,000/ml vs. 361,000/ml). At a higher injected concentration (10 mg/kg), analogue 4Q prevented platelet aggregation by all three stimuli at one- and three-hour time points. At the five-hour point, platelet responsiveness was slightly improved. The control responses in these studies were 70–80% of maximum. As shown in FIGS. 3c1 and 3c2 analogue 4R, at 3 mg/kg, exerted an apparent time-dependent effect on platelet responsiveness in that aggregation was reduced only 20–58% at one hour but 75–100% at three and five hours relative to control levels. Finally, a 10 mg/kg injection of this analogue caused the platelets to be unresponsive to all modes of stimulation at all time points. Here the control responses were 55–80% of maximum.

5. Peptide Effects on Coronary Blood Flow and Thrombosis

Coronary thrombosis was quantified as the time to full occlusion. The effects of the various peptide treatments on coronary thrombosis is illustrated in FIG. 4. In the control situation (saline injections), a full occlusion was observed in slightly more than two hours. Analogue 2G, even at 10 mg/kg, did not significantly influence this frequency. Analogue 4Q at 5 mg/kg significantly prolonged the time to occlusion and at 10 mg/kg completely prevented occlusion for the full five-hour experimental period. Moreover, at the low dose (5 mg/kg), analogue 4Q was able to prevent thrombus formation in animals whose circulating platelet levels were one-third of normal. Analogue 4R at 10 mg/kg prevented occlusion throughout the duration of the study but at 3 mg/kg was ineffective.

In these studies, the degree of anti-thrombotic efficacy appeared to coincide with the anti-aggregation potency described above. For example, analogues 4Q and 4R, which were superior inhibitors of in vitro aggregation, also exerted a considerably greater in vivo protective effect than analogue 2G at the same injected concentration. Moreover, these peptides were able to prevent full occlusion only when they completely prevented platelet stimulation by all of the agonists (at 10 mg/kg). However, analogue 4Q (at 5 mg/kg) completely or near-maximally blocked all aggregation responses but could merely prolong coronary occlusion. In addition, analogue 4R at 3 mg/kg blocked aggregation responses by 72–100% at the three- and five-hour points, yet at these times an occlusive thrombus had fully developed. Finally, these peptides could completely prevent occlusion in this model only at injected concentrations equivalent to 20- to 50-fold greater than their $IC_{50}$s against in vitro aggregation.

6. Hemodynamic Responses

Bleeding time was quantified at 1 hour before and one, three, and five hours after administration of the peptide. This was done by making a small (5 mm long and 1.5 mm deep) incision in the tongue and subsequently absorbing the exuded blood at this site every 15 seconds with a piece of Whatman filter paper until bleeding stopped. Platelet counts were determined with a Haema Count MK-4/HC platelet counting system.

It is important to note that these apparently excessive peptide concentrations did not exert any significant effects on template bleeding time, platelet counts, or on the main hemodynamic parameters (heart rate and blood pressure), which remained essentially unchanged and similar to baseline values throughout the experimental periods (FIG. 5). In cases where peptide treatment did not prevent occlusion, at certain times these parameters were not determined (ND in Table II), as experiments were terminated 30 min. after circumflex coronary artery blood flow had ceased due to occlusive thrombus formation.

EXAMPLE VIII

Anti-Thrombotic Properties of Hydrophobically Enhanced RGd Peptides in Prosthetic Arterial Grafts Adult male baboons (weighing 16 to 25 kg) were used in these studies. These were sedated with ketamine hydrochloride (200 to 250 mg intramuscular injection) and maintained under anesthesia with sodium pentobarbital (50 to 75 mg administered intravenously as necessary).

Twenty-four hours before the ex vivo shunt was established, platelets were isolated from 500 ml of blood from the test animal and labelled with ca. 500 microcuries of indium-111 oxine (Medi+Physics, Emeryville, Calif.), which irreversibly and specifically binds to platelets with an efficiency of 50%. Immediately after labelling, these platelets were then injected back into the animal and allowed to circulate for 24 hours. Immediately before the start of the study, fibrinogen that had been isolated from the animal and labelled with iodine-131 (DuPont Nuclear, Boston, Mass.) was also injected back into the animal. Also at this time, baseline determinations of the clotting and template bleeding times were made, and blood samples were drawn for hematology studies.

To establish the ex vivo shunt, the femoral artery and vein were percutaneously cannulated with introducer catheters (KMA Inc., Mansfield, Mass.). The catheters were then connected to medical-grade, heparin-coated silastic tubing (2.59 mm internal diameter, (Extracorporeal Medical Specialties, Inc., King of Prussia, Pa.). An electromagnetic flow probe was then inserted into the tubing by varying the resistance imparted by a partially occluding screw clamp that was distal to the probe. Finally, a 5 cm-long test segment of a 4 mm (internal diameter) vascular graft was inserted at the apex of the circuit. The graft used in these studies was GORE-TEX (expanded polytetrafluoroethylene, (W. L. Gore and Associates, Inc., Flagstaff, Ariz.). An electromagnetic flow probe was then inserted into the tubing circuit to measure blood flow, which was maintained at 100 ml/min. by varying the resistance imported by a partially occluding screw clamp that was distal to the probe. Finally, a 5 cm-long test segment of a 4 mm (internal diameter) vascular graft was inserted at the apex of the circuit. The graft used in these studies was GORE-TEX (expanded polytetrafluoroethylene, W. L. Gore and Associates, Inc., Flagstaff, Ariz.).

Platelet deposition onto the grafts was monitored by dynamic scanning with a gamma camera (Sigma 400, Ohio Nuclear, Inc., Sohon, Ohio), which detects the gamma radiation emitted by the $^{111}$indium-labelled platelets. Once the circuit was in place, the animal was placed under this camera, and blood flow-was initiated. Scans were then taken at the rate of one frame per two minutes for two hours. The data from these scans were collected on a dedicated Digital MDA computer (Maynard, Mass.). The scans were corrected for graft size, isotope dose and decay, circulating platelet activity and background, and the surface areas of the grafts.

At one- and two-hour time points, template bleeding times were measured, and blood samples were drawn to assess the hematology aggregation studies. Platelet aggregation studies were performed as described in Example V using ADP as the stimulus.

After a second, identical shunt was attached to the animal, the anti-platelet peptide GPenGHRGDLRCA was administered as an intravenous (IV) injection. A second series of scans was then obtained to ascertain the effect of the peptide on the platelet uptake pattern of the graft.

Upon the completion of each study, each shunt was flushed with lactated Ringer's solution, and each graft was then removed. Sections of these grafts were subjected to liquid scintillation counting to determine their content of residual $^{131}$iodine-fibrinogen and $^{111}$indium-platelets. The catheters in the femoral artery and vein were then removed, and hemostasis was achieved by compression. Finally, post-procedural blood samples were drawn, and determinations of template bleeding and clotting times were also made.

Three different animals were used in order to account for animal variability. Two of the three test animals displayed normal platelet uptake patterns, as determined from gamma camera images of $^{111}$IN-labeled platelets on the graft material. Treatments for these two animals are described below.

Figure 6:
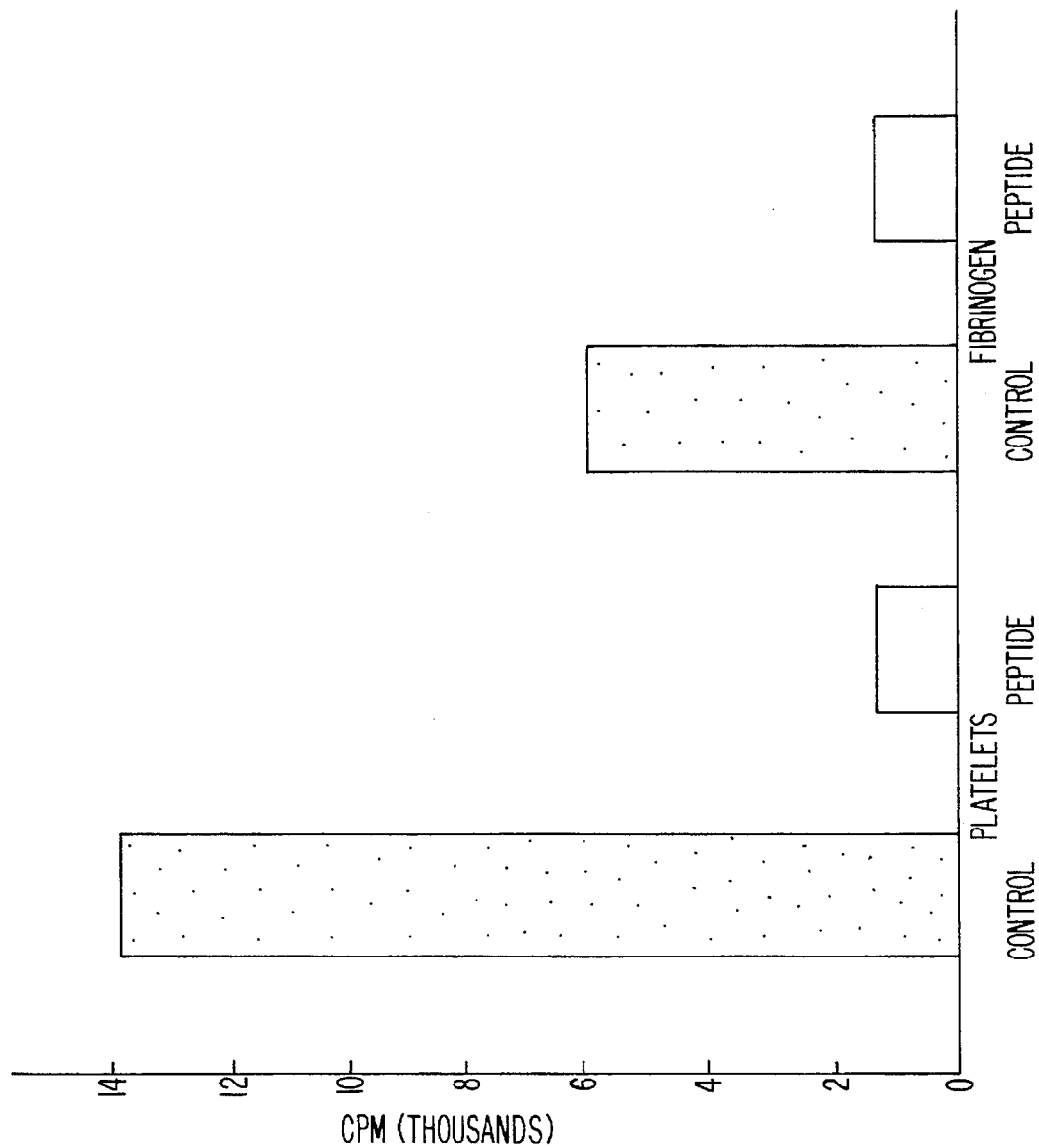
FIG. 6 shows the platelet and fibrinogen uptake by Gore-Tex grafts in animal 1 injected with the peptide of Example VIII.
Figure 7:
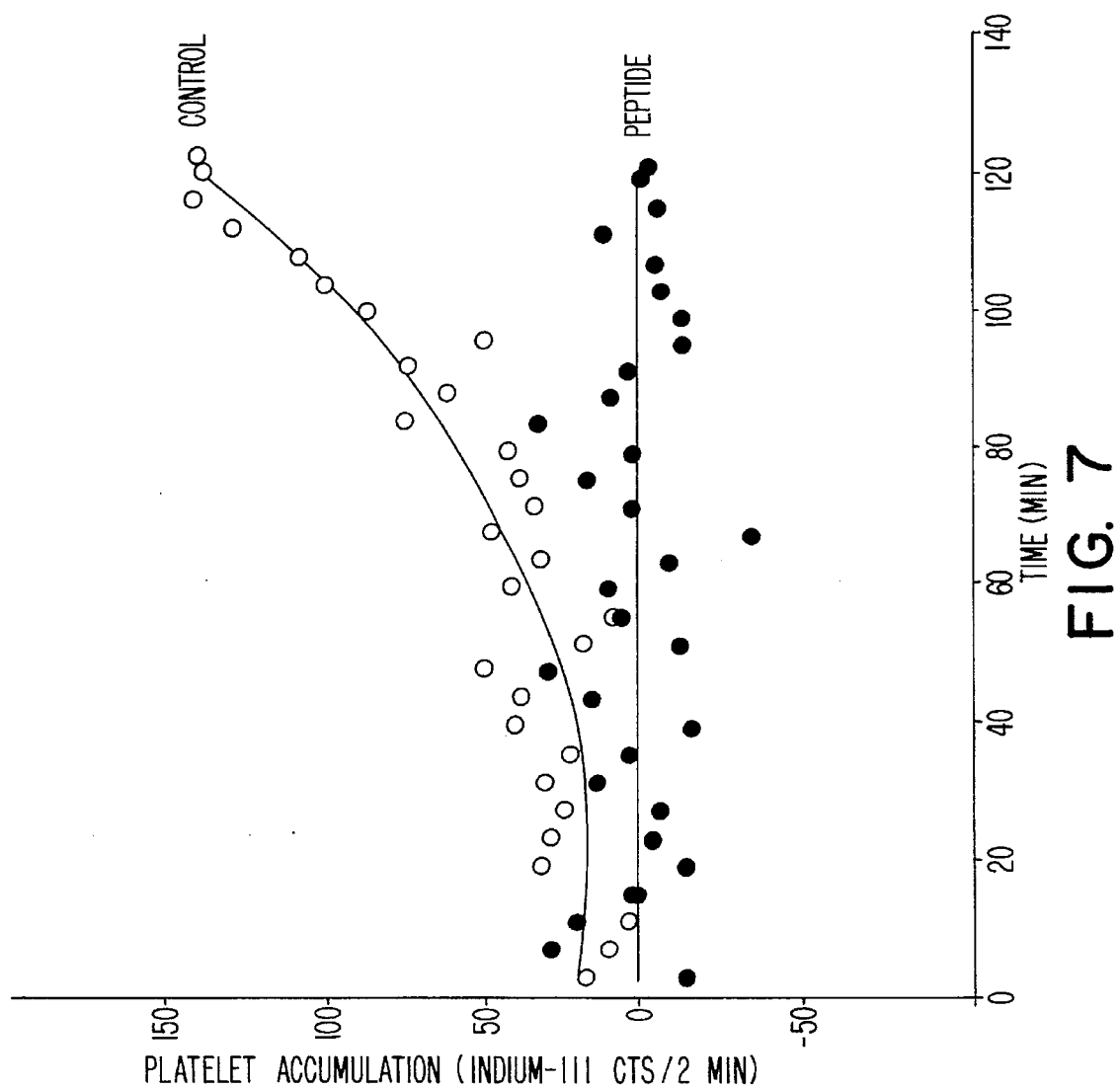
FIG. 7 shows the platelet uptake rates by GORE-TEX grafts in animal 1 injected with the peptide of Example VIII.

In the first of these animals, the peptide was administered as two bolus IV injections of 10 mg/kg (160 mg per injection). The first injection was given fifteen minutes before the establishment of the second shunt and the second injection was administered one hour afterward. As shown in FIG. 6, these injections caused a significant reduction in both $^{111}$In-platelet and $^{131}$I-fibrinogen uptakes (90% and 79%, respectively). This inhibitory effect is also apparent from a plot of platelet uptake rates in peptide-treated and untreated grafts over the entire time course of the studies (FIG. 7). Here, the rate of $^{111}$In-labelled platelet accumulation represents the counts observed in a graft piece minus those found in a background section of tubing at each time point when a scan was performed.

As shown in FIG. 8, peptide treatment did not lower template bleeding and clotting times. In blood samples taken immediately after completion of the second shunt, white blood cell and platelet counts, however, were reduced by 37% and 14%, respectively. Other parameters were unaffected.

Figure 9:
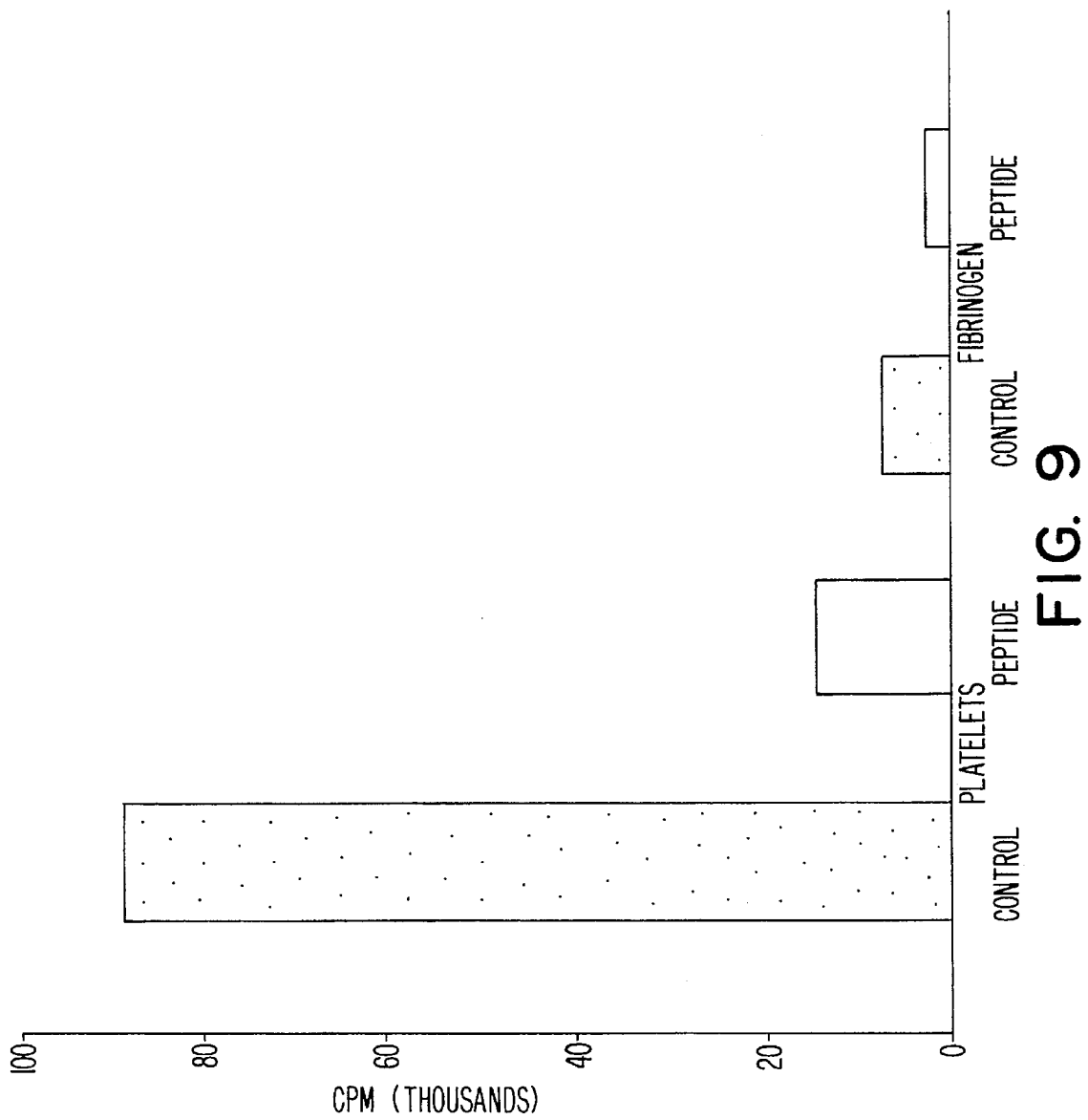
FIG. 9 shows the platelet and fibrinogen uptake by GORE-TEX grafts in animal 2 injected with the peptide of Example VIII.
Figure 10:
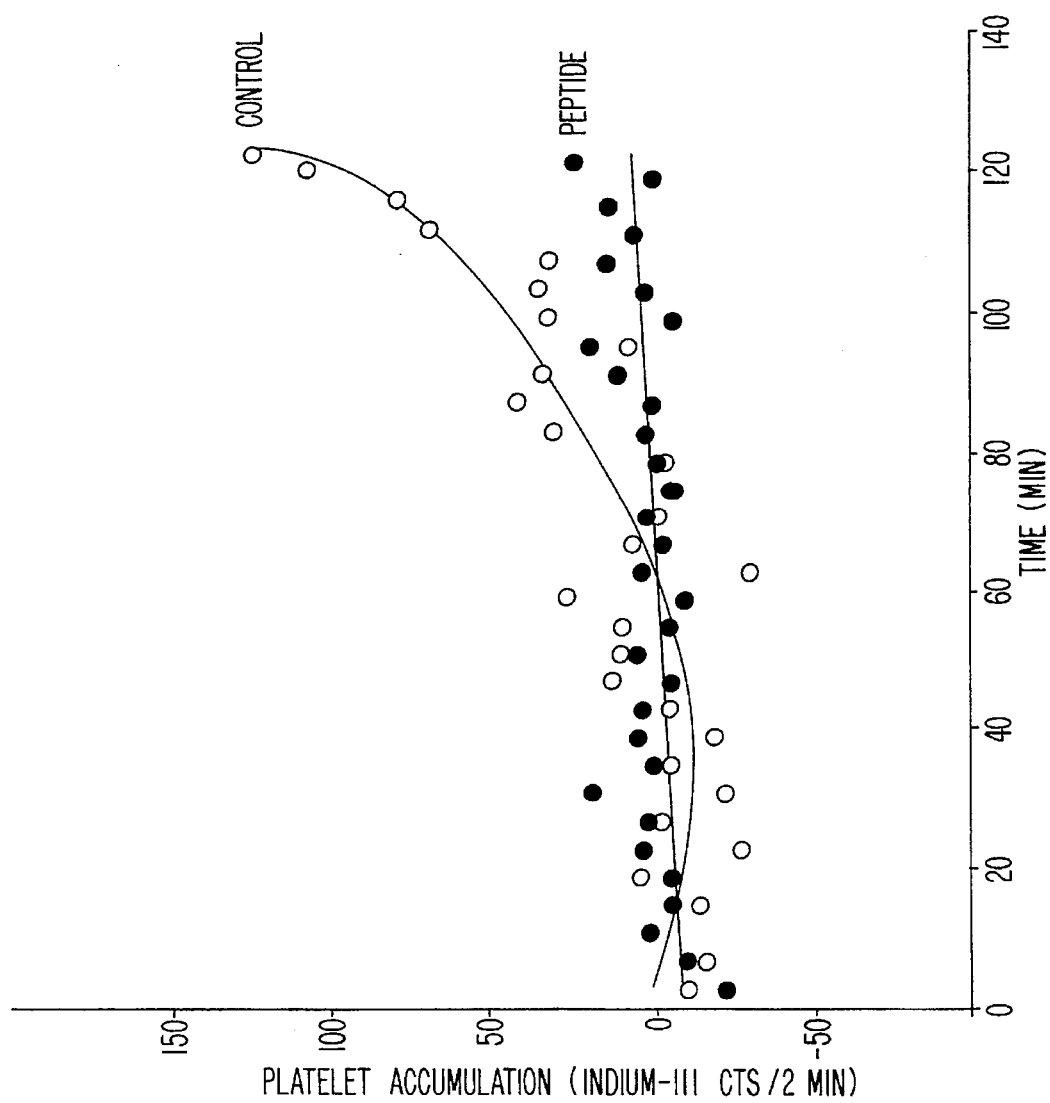
FIG. 10 shows the platelet uptake rates by GORE-TEX grafts in animal 2 injected with the peptide of Example VIII.

For the second animal, a 10 mg/kg bolus (250 mg) of the peptide was again given IV fifteen minutes before the initiation of the second shunt. This was immediately followed by a continuous infusion of 10 mg/kg/hr that lasted for the entire two hours of the shunt (500 mg total). As shown in FIG. 9, this treatment also caused significant reductions in labelled platelet and labelled fibrinogen uptakes (84% and 78%, respectively). Platelet uptake rates were again plotted in the presence and absence of the peptide (FIG. 10).

In addition, platelet aggregation studies were conducted on PRP derived from the second animal. Whole blood was drawn at three time points (0, 1 and 2 hours) of both control and experimental shunts. Platelets were completely unresponsive to the peptide treatment at a maximally effective concentration of ADP (10 μm). The peptide treatment also had no effect on template bleeding time, clotting time, or on all blood cell counts (FIG. 11).

EXAMPLE IX

Bleeding Time and Ex Vivo Platelet Aggregation Rabbit Model

1. Animal Preparation and Blood Sampling

Unanesthetized male New Zealand White rabbits (2.5–3.5 kg) were placed in a standard rabbit restrainer. Ears were shaved and a 20G teflon catheter with flowswitch (Viggo) was placed in the medial artery, flushed with saline and locked with 1 ml of heparinized saline (10 m/ml). A 22G catheter (Abbott) fitted with an injection cap (Medex) was placed in the marginal vein of the same ear. Saline or a GP $II_bIII_a$ receptor antagonist, at a concentration of 1 to 3 mg/ml, was infused via the venous catheter. At time 0, 41% of the dose was given as a bolus over 2 minutes. The remainder was continuously infused over the following 60 minutes. Blood samples (3.2 ml) were collected into syringes without needles via the arterial catheter at −10, −5, 10, 45 and 60 minutes. The first 0.5 ml was discarded and the following 2.7 ml was collected directly into a syringe containing 0.3 ml of 3.8% sodium citrate. The sample was divided into 1.5 ml aliquots and centrifuged at room temperature for 5 seconds at 12,000 G. The resulting platelet rich plasma (PRP) is used to measure ex-vivo platelet aggregation (XPA). At −10 and 60 minutes an additional 1.5 ml sample is drawn for an automated blood count (Baker Instruments). Catheters are flushed and locked after every sample.

2. Ex-Vivo Platelet Aggregation 300 ml of PRP was placed in a disposable glass cuvette with a stir bar. The cuvette was placed in the temperature regulated light path of a light transmittance aggregometer (Chrono-log) and equilibrated to a 37° C. Baseline transmittance was recorded for 30 seconds, after which 10 ml of ADP (1 mM) was added and the change in transmittance recorded. The maximum change from baseline (dT) was noted for each sample. The extent of inhibition of XPA that was produced by an inhibitor was calculated for each animal as follows: Mean dTs were calculated for the pre and post infusion values, and then, percent inhibition was calculated as (1-dt(post)/ddt(pre))×100.

3. Cutaneous Bleeding Times (CBT)

CBT was measured at −10, −5, 10, and 45 minutes on the opposite ear, using an automated incision-making instrument (Surgicutt®, ITD). An incision (5 mm×1 mm deep) was made on the dorsal surface of the ear at sites not supplied by major blood vessels. Blood was blotted away with absorbent paper placed near the incision site, every 2 to 15 seconds, to a maximum of 15 minutes. Cessation of bleeding was defined as no blood forming at the incision site for 15 seconds. The range of duplicate CBT in 40 normal rabbits was 0.88 to 3.38 minutes.

4. Peripheral Blood Flow (PBF)

For the experiments summarized in Table I, PBF was monitored by observation of the condition of the blood vessels in the rabbits' ears, prior to and during the infusion. Normal flow was defined as ears that appeared pink to red, with no visible constriction of the major blood vessels. Decreased flow applied to ears that have constricted vessels resulting in cold, pallid ears for up to 40 minutes following the start of the inhibitor infusion.

In an alternative series of experiments, (Table 2) PBF was measured quantitatively with a laser dopler flow probe (Perimed). The probe was positioned securely over the vascular bed of one ear and flow monitored continuously. Each inhibitor was infused and CBT measured in the opposing ear. No arterial catheter was placed for blood sampling, consequently XPA was measured in these animals. However, the doses used were shown in previous experiments to effectively inhibit XPA.

5. Results

CBT, XPA, and observed PBF were summarized in FIG. 12. The ratio of the post to pre treatment CBT was calculated for each animal by dividing the mean of the 2 post-treatment (and during infusion) samples by the mean of the pre samples. In two saline control rabbits the mean± sd ration of post treatment CBT (n=10) to a mean pre-treatment CBT was 1.12±0.19.

The experiments measuring PBF by laser dopler probe are summarized in Table III. As positive control, epinephrine was infused intravenously (1 mg over 2 minutes) at 60 minutes. The resulting vasoconstriction reduced flow to near 0 flow units within 5 minutes.

The doses listed in FIG. 12 and in Table III refer to the bolus portion only. There were no significant changes in any of the blood indices measured.

TABLE III

| Drug | Time (min.) | CBT (min.) | PBF (units) |
| --- | --- | --- | --- |
| RPenGHRGDWRCR[3] | 0 | 2.8 | 282 |
| 3.75 mg/kg | 10 | 1.5 | 9 |
|  | 45 | ND | ND |
| R(Pmc)GHRGD(O—Me—Y)RCR[8] | 0 | 2.9 | 392 |
| 1.5 mg/kg | 10 | 0.8 | 5 |
|  | 45 | 1.5 | 360 |
| R(Pmc)GHRGD(O—Me—Y)RCR[8] | 0 | 2.1 | 318 |
| 1.5 mg/kg | 10 | 3.8 | 0 |
|  | 45 | 1.2 | 283 |
| Ac—CNPRGD(O—Me—Y)RC—NH$_2$[13] | 0 | 1.8 | 263 |
| 4.5 mg/kg | 10 | 2.2 | 317 |
|  | 45 | 3.0 | 293 |

[3] = SEQ ID NO: 3; [8] = SEQ ID NO: 8; [13] = SEQ ID NO: 13

EXAMPLE X

Additional Results

Using the method described in Example V to measure ex vivo inhibition of platelet aggregation and the method described in Example VII to measure bleeding, four additional peptides were tested. These peptides included 11J, 11Q, 11K and 11V. Results are shown in Table IV. While all four peptides inhibited ex vivo platelet aggregation at the doses indicated, peptides 11J, 11K and 11V cause extensive prolongation of bleeding time, 11Q, in contrast, did not affect bleeding time. These results corroborated that it is the presence of a positive charge in the +4 position, as possessed by 11Q, which on platelet aggregation inhibiting peptides confers the characteristic of not prolonging bleeding time.

TABLE IV

| Code | Dose | ex vivo inhibition of platelet aggregation (%) | Pre dose bleeding time (min.) | Post dose bleeding time (min.) |
| --- | --- | --- | --- | --- |
| 11J | 5 Mg/Kg bolus; 120 µg/Kg/min. infusion | >98 | 2.1 | >30 |
| 11K | 6.8 Mg/Kg bolus; 163 µg/Kg/min. infusion | >98 | 2.1 | >30 |
| 11V | 8.5 Mg/Kg bolus | >98 | 2.0 | 21 |
| 11Q | 1.1 Mg/Kg bolus; 28.5 µg/Kg/min. infusion | >95 | 2.1 | 3.5 |

TABLE V

Inhibition of Platelet Aggregation

| Code | Formula | IC$_{50}$ (µM) |
| --- | --- | --- |
| 11Z | Ac—CSPRGD(O—Me—Y)RC—NH$_2$[115] | 0.45 |
| 12A | Ac—CAPRGD(O—Me—Y)RC—NH$_2$[116] | 0.41 |
| 12B | Ac—CLPRGD(O—Me—Y)RC—NH$_2$[117] | 0.28 |
| 12C | Ac—CDPRGD(O—Me—Y)RC—NH$_2$[118] | 3.0 |
| 12D | Ac—CYPRGD(O—Me—Y)RC—NH$_2$[119] | 0.22 |
| 12E | Ac—CRPRGD(O—Me—Y)RC—NH$_2$[120] | 0.34 |

[115] = SEQ ID NO: 115; [116] = SEQ ID NO: 116; [117] = SEQ ID NO: 117; [118] = SEQ ID NO: 118; [119] = SEQ ID NO: 119; [120] = SEQ ID NO: 120

As can be seen from the data in Table V, the residue lying two positions to the amino side of the RGD binding site is preferably non-acidic residue.

INDUSTRIAL APPLICATION

The compositions of matter disclosed and claimed herein are industrially useful for the prevention and treatment of pathologies characterized by undesirable platelet aggregation, including thrombosis, stroke and vascular graft occlusion.

Although the invention has been described with reference to the presently-preferred embodiment, it should be understood that various modifications can be made without departing from the spirit of the invention. Accordingly, the invention is limited only by the following claims.

We claim:

1. A peptide selected from the group consisting of:
GpenGHRGDLRCA (SEQ ID NO: 2);
RPenGHRGDWRCR (SEQ ID NO: 3);
RPenGHRGD(ChA)RCR (SEQ ID NO: 4);
PmpGHGDLRCA (SEQ ID NO: 5);
G(dPen)GHRGDLRCA (SEQ ID NO: 6);
R(Pmc)GHRGDWRCR (SEQ ID NO: 7);
R(Pmc)GHRGD(O—Me—Y)RCR (SEQ ID NO: 8);
R(Pmc)GHRGD(p-Cl—F)RCR (SEQ ID NO: 9);
R(Pmc)GHRGDFRCR (SEQ ID NO: 10);
R(Pmc)GHRGDFRCR (SEQ ID NO: 11);
R(t-but-Pmc)GHRGDLRCR (SEQ ID NO: 12);
Ac-CNPRGD(O—Me—Y)RC—NH$_2$ (SEQ ID NO: 13);
Ac-CNPKGD(O—Me—Y)RC—NH$_2$ (SEQ ID NO: 14); and
Ac-CNPRGD(O—N-Butyl-Y)RC—NH$_2$ (SEQ ID NO: 15);

the underlining of the amino acid residues indicates the cyclic portion of the peptide and, wherein the peptide inhibits platelet aggregation without prolonging bleeding time.

2. A composition comprising the peptide of claim 1 in a physiologically acceptable carrier.

3. A method of treating thrombosis, comprising administering a therapeutically effective amount of the peptide of claim 1 in a physiologically acceptable carrier.

* * * * *

UNITED STATES PATENT AND TRADEMARK OFFICE
CERTIFICATE OF CORRECTION

PATENT NO. : 5,612,311
DATED : Mar. 18, 1997
INVENTOR(S) : Pierschbacher et al.

It is certified that error appears in the above-identified patent and that said Letters Patent is hereby corrected as shown below:

In column 1, line 33, please delete "glycooprotein" and replace therefor with --glycoprotein--.

In column 5, line 51, please delete "$K_3[Fe(CN)_6]$." and replace therefor with --$K_3[F_e(CN)_6]$.--.

In column 10, line 53, please delete "FN-R" and replace therefor with --Fn-R--.

In claim 1, column 94, line 53, please delete "15);" and replace therefor with --15); wherein:--.

Signed and Sealed this

Tenth Day of April, 2001

Attest:

NICHOLAS P. GODICI

Attesting Officer

Acting Director of the United States Patent and Trademark Office

SEQUENCE LISTING ( 1 ) GENERAL INFORMATION:

( i i i ) NUMBER OF SEQUENCES: 120

( 2 ) INFORMATION FOR SEQ ID NO:1:

( i ) SEQUENCE CHARACTERISTICS:
        ( A ) LENGTH: 10 amino acids
        ( B ) TYPE: amino acid
        ( C ) STRANDEDNESS: single
        ( D ) TOPOLOGY: circular ( i x ) FEATURE:
        ( A ) NAME/KEY: Modified-site
        ( B ) LOCATION: 2
        ( D ) OTHER INFORMATION: /note="X=Pen"

( x i ) SEQUENCE DESCRIPTION: SEQ ID NO:1:

```
Arg  Xaa  Gly  Arg  Gly  Asp  Trp  Pro  Cys  Arg
1                   5                        10
```

( 2 ) INFORMATION FOR SEQ ID NO:2:

( i ) SEQUENCE CHARACTERISTICS:
        ( A ) LENGTH: 11 amino acids
        ( B ) TYPE: amino acid
        ( C ) STRANDEDNESS: single
        ( D ) TOPOLOGY: circular ( i x ) FEATURE:
        ( A ) NAME/KEY: Modified-site
        ( B ) LOCATION: 2
        ( D ) OTHER INFORMATION: /note="X=Pen"

( x i ) SEQUENCE DESCRIPTION: SEQ ID NO:2:

```
Gly  Xaa  Gly  His  Arg  Gly  Asp  Leu  Arg  Cys  Ala
1                   5                        10
```

( 2 ) INFORMATION FOR SEQ ID NO:3:

( i ) SEQUENCE CHARACTERISTICS:
        ( A ) LENGTH: 11 amino acids
        ( B ) TYPE: amino acid
        ( C ) STRANDEDNESS: single
        ( D ) TOPOLOGY: circular ( i x ) FEATURE:
        ( A ) NAME/KEY: Modified-site
        ( B ) LOCATION: 2
        ( D ) OTHER INFORMATION: /note="X=Pen"

( x i ) SEQUENCE DESCRIPTION: SEQ ID NO:3:

```
Arg  Xaa  Gly  His  Arg  Gly  Asp  Trp  Arg  Cys  Arg
1                   5                        10
```

( 2 ) INFORMATION FOR SEQ ID NO:4:

( i ) SEQUENCE CHARACTERISTICS:
        ( A ) LENGTH: 11 amino acids ( B ) TYPE: amino acid
                ( C ) STRANDEDNESS: single
                ( D ) TOPOLOGY: circular ( i x ) FEATURE:
                ( A ) NAME/KEY: Modified-site
                ( B ) LOCATION: 2
                ( D ) OTHER INFORMATION: /note="X=Pen"

( i x ) FEATURE:
                ( A ) NAME/KEY: Modified-site
                ( B ) LOCATION: 8
                ( D ) OTHER INFORMATION: /note="X=(ChA)"

( x i ) SEQUENCE DESCRIPTION: SEQ ID NO:4:

Arg  Xaa  Gly  His  Arg  Gly  Asp  Xaa  Arg  Cys  Arg
        1                   5                        10

( 2 ) INFORMATION FOR SEQ ID NO:5:

( i ) SEQUENCE CHARACTERISTICS:
                ( A ) LENGTH: 10 amino acids
                ( B ) TYPE: amino acid
                ( C ) STRANDEDNESS: single
                ( D ) TOPOLOGY: circular ( i x ) FEATURE:
                ( A ) NAME/KEY: Modified-site
                ( B ) LOCATION: 1
                ( D ) OTHER INFORMATION: /note="X=Pmp"

( x i ) SEQUENCE DESCRIPTION: SEQ ID NO:5:

Xaa  Gly  His  Arg  Gly  Asp  Leu  Arg  Cys  Ala
        1                   5                        10

( 2 ) INFORMATION FOR SEQ ID NO:6:

( i ) SEQUENCE CHARACTERISTICS:
                ( A ) LENGTH: 11 amino acids
                ( B ) TYPE: amino acid
                ( C ) STRANDEDNESS: single
                ( D ) TOPOLOGY: circular ( i x ) FEATURE:
                ( A ) NAME/KEY: Modified-site
                ( B ) LOCATION: 2
                ( D ) OTHER INFORMATION: /note="X=(dPen)"

( x i ) SEQUENCE DESCRIPTION: SEQ ID NO:6:

Gly  Xaa  Gly  His  Arg  Gly  Asp  Leu  Arg  Cys  Ala
        1                   5                        10

( 2 ) INFORMATION FOR SEQ ID NO:7:

( i ) SEQUENCE CHARACTERISTICS:
                ( A ) LENGTH: 11 amino acids
                ( B ) TYPE: amino acid
                ( C ) STRANDEDNESS: single
                ( D ) TOPOLOGY: circular ( i x ) FEATURE:
                ( A ) NAME/KEY: Modified-site
                ( B ) LOCATION: 2
                ( D ) OTHER INFORMATION: /note="X=(Pmc)"

( x i ) SEQUENCE DESCRIPTION: SEQ ID NO:7:

Arg  Xaa  Gly  His  Arg  Gly  Asp  Trp  Arg  Cys  Arg
        1                   5                        10

( 2 ) INFORMATION FOR SEQ ID NO:8:

( i ) SEQUENCE CHARACTERISTICS:

(A) LENGTH: 11 amino acids
(B) TYPE: amino acid
(C) STRANDEDNESS: single
(D) TOPOLOGY: circular (ix) FEATURE:
  (A) NAME/KEY: Modified-site
  (B) LOCATION: 2
  (D) OTHER INFORMATION: /note="X=(Pmc)"

(ix) FEATURE:
  (A) NAME/KEY: Modified-site
  (B) LOCATION: 8
  (D) OTHER INFORMATION: /note="X=(O-Me-Y)"

(xi) SEQUENCE DESCRIPTION: SEQ ID NO:8:

Arg Xaa Gly His Arg Gly Asp Xaa Arg Cys Arg
1               5                   10

(2) INFORMATION FOR SEQ ID NO:9:

(i) SEQUENCE CHARACTERISTICS:
  (A) LENGTH: 11 amino acids
  (B) TYPE: amino acid
  (C) STRANDEDNESS: single
  (D) TOPOLOGY: circular (ix) FEATURE:
  (A) NAME/KEY: Modified-site
  (B) LOCATION: 2
  (D) OTHER INFORMATION: /note="X=(Pmc)"

(ix) FEATURE:
  (A) NAME/KEY: Modified-site
  (B) LOCATION: 8
  (D) OTHER INFORMATION: /note="X=(P-Cl-F)"

(xi) SEQUENCE DESCRIPTION: SEQ ID NO:9:

Arg Xaa Gly His Arg Gly Asp Xaa Arg Cys Arg
1               5                   10

(2) INFORMATION FOR SEQ ID NO:10:

(i) SEQUENCE CHARACTERISTICS:
  (A) LENGTH: 11 amino acids
  (B) TYPE: amino acid
  (C) STRANDEDNESS: single
  (D) TOPOLOGY: circular (ix) FEATURE:
  (A) NAME/KEY: Modified-site
  (B) LOCATION: 2
  (D) OTHER INFORMATION: /note="X=(Pmc)"

(xi) SEQUENCE DESCRIPTION: SEQ ID NO:10:

Arg Xaa Gly His Arg Gly Asp Leu Arg Cys Arg
1               5                   10

(2) INFORMATION FOR SEQ ID NO:11:

(i) SEQUENCE CHARACTERISTICS:
  (A) LENGTH: 11 amino acids
  (B) TYPE: amino acid
  (C) STRANDEDNESS: single
  (D) TOPOLOGY: circular (ix) FEATURE:
  (A) NAME/KEY: Modified-site
  (B) LOCATION: 2
  (D) OTHER INFORMATION: /note="X=(Pmc)"

(xi) SEQUENCE DESCRIPTION: SEQ ID NO:11:

```
Arg  Xaa  Gly  His  Arg  Gly  Asp  Phe  Arg  Cys  Arg
 1              5                        10
```

( 2 ) INFORMATION FOR SEQ ID NO:12:

( i ) SEQUENCE CHARACTERISTICS:
        ( A ) LENGTH: 11 amino acids
        ( B ) TYPE: amino acid
        ( C ) STRANDEDNESS: single
        ( D ) TOPOLOGY: circular ( i x ) FEATURE:
        ( A ) NAME/KEY: Modified-site
        ( B ) LOCATION: 2
        ( D ) OTHER INFORMATION: /note="X=(t-but-Pmc)"

( x i ) SEQUENCE DESCRIPTION: SEQ ID NO:12:

```
Arg  Xaa  Gly  His  Arg  Gly  Asp  Leu  Arg  Cys  Arg
 1              5                        10
```

( 2 ) INFORMATION FOR SEQ ID NO:13:

( i ) SEQUENCE CHARACTERISTICS:
        ( A ) LENGTH: 11 amino acids
        ( B ) TYPE: amino acid
        ( C ) STRANDEDNESS: single
        ( D ) TOPOLOGY: circular ( i x ) FEATURE:
        ( A ) NAME/KEY: Region
        ( B ) LOCATION: 1
        ( D ) OTHER INFORMATION: /note="X=Ac-"

( i x ) FEATURE:
        ( A ) NAME/KEY: Modified-site
        ( B ) LOCATION: 8
        ( D ) OTHER INFORMATION: /note="X=(O-Me-Y)"

( i x ) FEATURE:
        ( A ) NAME/KEY: Region
        ( B ) LOCATION: 11
        ( D ) OTHER INFORMATION: /note="X=-N(H)2"

( x i ) SEQUENCE DESCRIPTION: SEQ ID NO:13:

```
Xaa  Cys  Asn  Pro  Arg  Gly  Asp  Xaa  Arg  Cys  Xaa
 1              5                        10
```

( 2 ) INFORMATION FOR SEQ ID NO:14:

( i ) SEQUENCE CHARACTERISTICS:
        ( A ) LENGTH: 11 amino acids
        ( B ) TYPE: amino acid
        ( C ) STRANDEDNESS: single
        ( D ) TOPOLOGY: circular ( i x ) FEATURE:
        ( A ) NAME/KEY: Region
        ( B ) LOCATION: 1
        ( D ) OTHER INFORMATION: /note="X=Ac-"

( i x ) FEATURE:
        ( A ) NAME/KEY: Modified-site
        ( B ) LOCATION: 8
        ( D ) OTHER INFORMATION: /note="X=(O-Me-Y)"

( i x ) FEATURE:
        ( A ) NAME/KEY: Region
        ( B ) LOCATION: 11
        ( D ) OTHER INFORMATION: /note="X=-N(H)2"

( x i ) SEQUENCE DESCRIPTION: SEQ ID NO:14:

```
Xaa  Cys  Asn  Pro  Lys  Gly  Asp  Xaa  Arg  Cys  Xaa
 1              5                        10
```

( 2 ) INFORMATION FOR SEQ ID NO:15:

( i ) SEQUENCE CHARACTERISTICS:
            ( A ) LENGTH: 11 amino acids
            ( B ) TYPE: amino acid
            ( C ) STRANDEDNESS: single
            ( D ) TOPOLOGY: circular ( i x ) FEATURE:
            ( A ) NAME/KEY: Region
            ( B ) LOCATION: 1
            ( D ) OTHER INFORMATION: /note="X=Ac-"

( i x ) FEATURE:
            ( A ) NAME/KEY: Modified-site
            ( B ) LOCATION: 8
            ( D ) OTHER INFORMATION: /note="X=(O-N-Butyl-Y)"

( i x ) FEATURE:
            ( A ) NAME/KEY: Region
            ( B ) LOCATION: 11
            ( D ) OTHER INFORMATION: /note="X=-N(H)2"

( x i ) SEQUENCE DESCRIPTION: SEQ ID NO:15:

Xaa  Cys  Asn  Pro  Arg  Gly  Asp  Xaa  Arg  Cys  Xaa
       1                          5                                    10

( 2 ) INFORMATION FOR SEQ ID NO:16:

( i ) SEQUENCE CHARACTERISTICS:
            ( A ) LENGTH: 10 amino acids
            ( B ) TYPE: amino acid
            ( C ) STRANDEDNESS: single
            ( D ) TOPOLOGY: circular ( i x ) FEATURE:
            ( A ) NAME/KEY: Modified-site
            ( B ) LOCATION: 2
            ( D ) OTHER INFORMATION: /note="X=Pen"

( i x ) FEATURE:
            ( A ) NAME/KEY: Modified-site
            ( B ) LOCATION: 7
            ( D ) OTHER INFORMATION: /note="X="F"and "W""

( x i ) SEQUENCE DESCRIPTION: SEQ ID NO:16:

Gly  Xaa  Gly  Arg  Gly  Asp  Xaa  Pro  Cys  Ala
       1                          5                                 10

( 2 ) INFORMATION FOR SEQ ID NO:17:

( i ) SEQUENCE CHARACTERISTICS:
            ( A ) LENGTH: 11 amino acids
            ( B ) TYPE: amino acid
            ( C ) STRANDEDNESS: single
            ( D ) TOPOLOGY: circular ( i x ) FEATURE:
            ( A ) NAME/KEY: Modified-site
            ( B ) LOCATION: 2
            ( D ) OTHER INFORMATION: /note="X=Pen"

( i x ) FEATURE:
            ( A ) NAME/KEY: Modified-site
            ( B ) LOCATION: 8
            ( D ) OTHER INFORMATION: /note="X="F"and "W""

( x i ) SEQUENCE DESCRIPTION: SEQ ID NO:17:

Gly  Xaa  Gly  His  Arg  Gly  Asp  Xaa  Arg  Cys  Ala
       1                          5                                 10

( 2 ) INFORMATION FOR SEQ ID NO:18:

(i) SEQUENCE CHARACTERISTICS:
    (A) LENGTH: 10 amino acids
    (B) TYPE: amino acid
    (C) STRANDEDNESS: single
    (D) TOPOLOGY: circular (ix) FEATURE:
    (A) NAME/KEY: Modified-site
    (B) LOCATION: 2
    (D) OTHER INFORMATION: /note="X=Pen"

(xi) SEQUENCE DESCRIPTION: SEQ ID NO:18:

```
Gly  Xaa  Gly  Arg  Gly  Asp  Ser  Pro  Cys  Ala
 1                    5                        10
```

(2) INFORMATION FOR SEQ ID NO:19:

(i) SEQUENCE CHARACTERISTICS:
    (A) LENGTH: 10 amino acids
    (B) TYPE: amino acid
    (C) STRANDEDNESS: single
    (D) TOPOLOGY: circular (ix) FEATURE:
    (A) NAME/KEY: Modified-site
    (B) LOCATION: 1
    (D) OTHER INFORMATION: /note="X="R"or "L""

(ix) FEATURE:
    (A) NAME/KEY: Modified-site
    (B) LOCATION: 2
    (D) OTHER INFORMATION: /note="X=Pen"

(xi) SEQUENCE DESCRIPTION: SEQ ID NO:19:

```
Xaa  Xaa  Gly  Arg  Gly  Asp  Ser  Pro  Cys  Ala
 1                    5                        10
```

(2) INFORMATION FOR SEQ ID NO:20:

(i) SEQUENCE CHARACTERISTICS:
    (A) LENGTH: 11 amino acids
    (B) TYPE: amino acid
    (C) STRANDEDNESS: single
    (D) TOPOLOGY: circular (ix) FEATURE:
    (A) NAME/KEY: Modified-site
    (B) LOCATION: 1
    (D) OTHER INFORMATION: /note="X="R"or "L""

(ix) FEATURE:
    (A) NAME/KEY: Modified-site
    (B) LOCATION: 2
    (D) OTHER INFORMATION: /note="X=Pen"

(xi) SEQUENCE DESCRIPTION: SEQ ID NO:20:

```
Xaa  Xaa  Gly  His  Arg  Gly  Asp  Leu  Arg  Cys  Ala
 1                    5                             10
```

(2) INFORMATION FOR SEQ ID NO:21:

(i) SEQUENCE CHARACTERISTICS:
    (A) LENGTH: 11 amino acids
    (B) TYPE: amino acid
    (C) STRANDEDNESS: single
    (D) TOPOLOGY: circular (ix) FEATURE:
    (A) NAME/KEY: Modified-site
    (B) LOCATION: 2
    (D) OTHER INFORMATION: /note="X=organic mimic bridging
        structures"

(xi) SEQUENCE DESCRIPTION: SEQ ID NO:21:

```
                    Gly  Xaa  Gly  His  Arg  Gly  Asp  Leu  Arg  Cys  Ala
                    1                   5                        10
```

( 2 ) INFORMATION FOR SEQ ID NO:22:

( i ) SEQUENCE CHARACTERISTICS:
        ( A ) LENGTH: 11 amino acids
        ( B ) TYPE: amino acid
        ( C ) STRANDEDNESS: single
        ( D ) TOPOLOGY: circular ( i x ) FEATURE:
        ( A ) NAME/KEY: Modified-site
        ( B ) LOCATION: 2
        ( D ) OTHER INFORMATION: /note="X=(1-Pen)"

( x i ) SEQUENCE DESCRIPTION: SEQ ID NO:22:

```
                    Gly  Xaa  Gly  His  Arg  Gly  Asp  Leu  Arg  Cys  Ala
                    1                   5                        10
```

( 2 ) INFORMATION FOR SEQ ID NO:23:

( i ) SEQUENCE CHARACTERISTICS:
        ( A ) LENGTH: 6 amino acids
        ( B ) TYPE: amino acid
        ( C ) STRANDEDNESS: single
        ( D ) TOPOLOGY: circular ( x i ) SEQUENCE DESCRIPTION: SEQ ID NO:23:

```
                    Gly  Arg  Gly  Asp  Ser  Pro
                    1                   5
```

( 2 ) INFORMATION FOR SEQ ID NO:24:

( i ) SEQUENCE CHARACTERISTICS:
        ( A ) LENGTH: 10 amino acids
        ( B ) TYPE: amino acid
        ( C ) STRANDEDNESS: single
        ( D ) TOPOLOGY: circular ( i x ) FEATURE:
        ( A ) NAME/KEY: Modified-site
        ( B ) LOCATION: 2
        ( D ) OTHER INFORMATION: /note="X=Pen"

( x i ) SEQUENCE DESCRIPTION: SEQ ID NO:24:

```
                    Gly  Xaa  Gly  Arg  Gly  Asp  Thr  Pro  Cys  Ala
                    1                   5                        10
```

( 2 ) INFORMATION FOR SEQ ID NO:25:

( i ) SEQUENCE CHARACTERISTICS:
        ( A ) LENGTH: 10 amino acids
        ( B ) TYPE: amino acid
        ( C ) STRANDEDNESS: single
        ( D ) TOPOLOGY: circular ( i x ) FEATURE:
        ( A ) NAME/KEY: Modified-site
        ( B ) LOCATION: 2
        ( D ) OTHER INFORMATION: /note="X=Pen"

( x i ) SEQUENCE DESCRIPTION: SEQ ID NO:25:

```
                    Gly  Xaa  Gly  Arg  Gly  Asp  Leu  Pro  Cys  Ala
                    1                   5                        10
```

( 2 ) INFORMATION FOR SEQ ID NO:26:

( i ) SEQUENCE CHARACTERISTICS:
        ( A ) LENGTH: 10 amino acids ( B ) TYPE: amino acid
( C ) STRANDEDNESS: single
( D ) TOPOLOGY: circular ( i x ) FEATURE:
( A ) NAME/KEY: Modified-site
( B ) LOCATION: 2
( D ) OTHER INFORMATION: /note="X=Pen"

( x i ) SEQUENCE DESCRIPTION: SEQ ID NO:26:

```
Gly Xaa Gly Arg Gly Asp Phe Pro Cys Ala
1               5                   10
```

( 2 ) INFORMATION FOR SEQ ID NO:27:

( i ) SEQUENCE CHARACTERISTICS:
( A ) LENGTH: 10 amino acids
( B ) TYPE: amino acid
( C ) STRANDEDNESS: single
( D ) TOPOLOGY: circular ( i x ) FEATURE:
( A ) NAME/KEY: Modified-site
( B ) LOCATION: 2
( D ) OTHER INFORMATION: /note="X=Pen"

( x i ) SEQUENCE DESCRIPTION: SEQ ID NO:27:

```
Gly Xaa Gly Arg Gly Asp Trp Pro Cys Ala
1               5                   10
```

( 2 ) INFORMATION FOR SEQ ID NO:28:

( i ) SEQUENCE CHARACTERISTICS:
( A ) LENGTH: 10 amino acids
( B ) TYPE: amino acid
( C ) STRANDEDNESS: single
( D ) TOPOLOGY: circular ( i x ) FEATURE:
( A ) NAME/KEY: Modified-site
( B ) LOCATION: 2
( D ) OTHER INFORMATION: /note="X=Pen"

( x i ) SEQUENCE DESCRIPTION: SEQ ID NO:28:

```
Arg Xaa Gly Arg Gly Asp Trp Pro Cys Arg
1               5                   10
```

( 2 ) INFORMATION FOR SEQ ID NO:29:

( i ) SEQUENCE CHARACTERISTICS:
( A ) LENGTH: 11 amino acids
( B ) TYPE: amino acid
( C ) STRANDEDNESS: single
( D ) TOPOLOGY: circular ( i x ) FEATURE:
( A ) NAME/KEY: Modified-site
( B ) LOCATION: 2
( D ) OTHER INFORMATION: /note="X=Pen"

( x i ) SEQUENCE DESCRIPTION: SEQ ID NO:29:

```
Arg Xaa Gly His Arg Gly Asp Leu Arg Cys Arg
1               5                   10
```

( 2 ) INFORMATION FOR SEQ ID NO:30:

( i ) SEQUENCE CHARACTERISTICS:
( A ) LENGTH: 11 amino acids
( B ) TYPE: amino acid
( C ) STRANDEDNESS: single
( D ) TOPOLOGY: circular ( i x ) FEATURE:
    ( A ) NAME/KEY: Modified-site
    ( B ) LOCATION: 2
    ( D ) OTHER INFORMATION: /note="X=Pen"

( i x ) FEATURE:
    ( A ) NAME/KEY: Modified-site
    ( B ) LOCATION: 8
    ( D ) OTHER INFORMATION: /note="X=(1-napA)"

( x i ) SEQUENCE DESCRIPTION: SEQ ID NO:30:

Arg Xaa Gly His Arg Gly Asp Xaa Arg Cys Arg
1               5                   10

( 2 ) INFORMATION FOR SEQ ID NO:31:

( i ) SEQUENCE CHARACTERISTICS:
        ( A ) LENGTH: 11 amino acids
        ( B ) TYPE: amino acid
        ( C ) STRANDEDNESS: single
        ( D ) TOPOLOGY: circular ( i x ) FEATURE:
        ( A ) NAME/KEY: Modified-site
        ( B ) LOCATION: 2
        ( D ) OTHER INFORMATION: /note="X=(Pmc)"

( x i ) SEQUENCE DESCRIPTION: SEQ ID NO:31:

Gly Xaa Gly His Arg Gly Asp Leu Arg Cys Ala
1               5                   10

( 2 ) INFORMATION FOR SEQ ID NO:32:

( i ) SEQUENCE CHARACTERISTICS:
        ( A ) LENGTH: 10 amino acids
        ( B ) TYPE: amino acid
        ( C ) STRANDEDNESS: single
        ( D ) TOPOLOGY: circular ( i x ) FEATURE:
        ( A ) NAME/KEY: Modified-site
        ( B ) LOCATION: 1
        ( D ) OTHER INFORMATION: /note="X=(t-but-Pmp)"

( x i ) SEQUENCE DESCRIPTION: SEQ ID NO:32:

Xaa Gly His Arg Gly Asp Leu Arg Cys Ala
1               5                   10

( 2 ) INFORMATION FOR SEQ ID NO:33:

( i ) SEQUENCE CHARACTERISTICS:
        ( A ) LENGTH: 10 amino acids
        ( B ) TYPE: amino acid
        ( C ) STRANDEDNESS: single
        ( D ) TOPOLOGY: circular ( i x ) FEATURE:
        ( A ) NAME/KEY: Modified-site
        ( B ) LOCATION: 1
        ( D ) OTHER INFORMATION: /note="X=(t-but-Pmc)"

( i x ) FEATURE:
        ( A ) NAME/KEY: Modified-site
        ( B ) LOCATION: 9
        ( D ) OTHER INFORMATION: /note="X=Pen"

( x i ) SEQUENCE DESCRIPTION: SEQ ID NO:33:

Xaa Gly His Arg Gly Asp Leu Arg Xaa Ala
1               5                   10

( 2 ) INFORMATION FOR SEQ ID NO:34:

( i ) SEQUENCE CHARACTERISTICS:
  ( A ) LENGTH: 8 amino acids
  ( B ) TYPE: amino acid
  ( C ) STRANDEDNESS: single
  ( D ) TOPOLOGY: circular ( i x ) FEATURE:
  ( A ) NAME/KEY: Modified-site
  ( B ) LOCATION: 2
  ( D ) OTHER INFORMATION: /note="X=(Pmc)"

( i x ) FEATURE:
  ( A ) NAME/KEY: Modified-site
  ( B ) LOCATION: 6
  ( D ) OTHER INFORMATION: /note="X=(ChA)"

( x i ) SEQUENCE DESCRIPTION: SEQ ID NO:34:

Arg Xaa Arg Gly Asp Xaa Cys Arg
1               5

( 2 ) INFORMATION FOR SEQ ID NO:35:

( i ) SEQUENCE CHARACTERISTICS:
  ( A ) LENGTH: 10 amino acids
  ( B ) TYPE: amino acid
  ( C ) STRANDEDNESS: single
  ( D ) TOPOLOGY: circular ( i x ) FEATURE:
  ( A ) NAME/KEY: Modified-site
  ( B ) LOCATION: 2
  ( D ) OTHER INFORMATION: /note="X=(Pmc)"

( x i ) SEQUENCE DESCRIPTION: SEQ ID NO:35:

Arg Xaa Gly Arg Gly Asp Trp Pro Cys Arg
1               5                   10

( 2 ) INFORMATION FOR SEQ ID NO:36:

( i ) SEQUENCE CHARACTERISTICS:
  ( A ) LENGTH: 11 amino acids
  ( B ) TYPE: amino acid
  ( C ) STRANDEDNESS: single
  ( D ) TOPOLOGY: circular ( i x ) FEATURE:
  ( A ) NAME/KEY: Modified-site
  ( B ) LOCATION: 2
  ( D ) OTHER INFORMATION: /note="X=(Pmc)"

( i x ) FEATURE:
  ( A ) NAME/KEY: Modified-site
  ( B ) LOCATION: 8
  ( D ) OTHER INFORMATION: /note="X=(O-n-hexyl-Y)"

( x i ) SEQUENCE DESCRIPTION: SEQ ID NO:36:

Arg Xaa Gly His Arg Gly Asp Xaa Arg Cys Arg
1               5                       10

( 2 ) INFORMATION FOR SEQ ID NO:37:

( i ) SEQUENCE CHARACTERISTICS:
  ( A ) LENGTH: 11 amino acids
  ( B ) TYPE: amino acid
  ( C ) STRANDEDNESS: single
  ( D ) TOPOLOGY: circular ( i x ) FEATURE:
  ( A ) NAME/KEY: Modified-site
  ( B ) LOCATION: 2
  ( D ) OTHER INFORMATION: /note="X=(Pmc)"

( i x ) FEATURE:
  ( A ) NAME/KEY: Modified-site ( B ) LOCATION: 8
( D ) OTHER INFORMATION: /note="X=(3,5-diiodo-Y)"

( x i ) SEQUENCE DESCRIPTION: SEQ ID NO:37:

Arg Xaa Gly His Arg Gly Asp Xaa Arg Cys Arg
1               5                   10

( 2 ) INFORMATION FOR SEQ ID NO:38:

( i ) SEQUENCE CHARACTERISTICS:
( A ) LENGTH: 11 amino acids
( B ) TYPE: amino acid
( C ) STRANDEDNESS: single
( D ) TOPOLOGY: circular ( i x ) FEATURE:
( A ) NAME/KEY: Modified-site
( B ) LOCATION: 2
( D ) OTHER INFORMATION: /note="X=(Pmc)"

( i x ) FEATURE:
( A ) NAME/KEY: Modified-site
( B ) LOCATION: 8
( D ) OTHER INFORMATION: /note="X=(Hpa)"

( x i ) SEQUENCE DESCRIPTION: SEQ ID NO:38:

Arg Xaa Gly His Arg Gly Asp Xaa Arg Cys Arg
1               5                   10

( 2 ) INFORMATION FOR SEQ ID NO:39:

( i ) SEQUENCE CHARACTERISTICS:
( A ) LENGTH: 11 amino acids
( B ) TYPE: amino acid
( C ) STRANDEDNESS: single
( D ) TOPOLOGY: circular ( i x ) FEATURE:
( A ) NAME/KEY: Modified-site
( B ) LOCATION: 2
( D ) OTHER INFORMATION: /note="X=(Pmc)"

( i x ) FEATURE:
( A ) NAME/KEY: Modified-site
( B ) LOCATION: 8
( D ) OTHER INFORMATION: /note="X=(2-NapA)"

( x i ) SEQUENCE DESCRIPTION: SEQ ID NO:39:

Arg Xaa Gly His Arg Gly Asp Xaa Arg Cys Arg
1               5                   10

( 2 ) INFORMATION FOR SEQ ID NO:40:

( i ) SEQUENCE CHARACTERISTICS:
( A ) LENGTH: 11 amino acids
( B ) TYPE: amino acid
( C ) STRANDEDNESS: single
( D ) TOPOLOGY: circular ( i x ) FEATURE:
( A ) NAME/KEY: Modified-site
( B ) LOCATION: 2
( D ) OTHER INFORMATION: /note="X=(Pmc)"

( i x ) FEATURE:
( A ) NAME/KEY: Modified-site
( B ) LOCATION: 8
( D ) OTHER INFORMATION: /note="X=(O-n-butyl-Y)"

( x i ) SEQUENCE DESCRIPTION: SEQ ID NO:40:

Arg Xaa Gly His Arg Gly Asp Xaa Arg Cys Arg
1               5                   10

( 2 ) INFORMATION FOR SEQ ID NO:41:

( i ) SEQUENCE CHARACTERISTICS:
        ( A ) LENGTH: 11 amino acids
        ( B ) TYPE: amino acid
        ( C ) STRANDEDNESS: single
        ( D ) TOPOLOGY: circular ( i x ) FEATURE:
        ( A ) NAME/KEY: Modified-site
        ( B ) LOCATION: 2
        ( D ) OTHER INFORMATION: /note="X=(Pmc)"

( i x ) FEATURE:
        ( A ) NAME/KEY: Modified-site
        ( B ) LOCATION: 8
        ( D ) OTHER INFORMATION: /note="X=(p-nitro=F)"

( x i ) SEQUENCE DESCRIPTION: SEQ ID NO:41:

Arg Xaa Gly His Arg Gly Asp Xaa Arg Cys Arg
    1                 5                      10

( 2 ) INFORMATION FOR SEQ ID NO:42:

( i ) SEQUENCE CHARACTERISTICS:
        ( A ) LENGTH: 11 amino acids
        ( B ) TYPE: amino acid
        ( C ) STRANDEDNESS: single
        ( D ) TOPOLOGY: circular ( i x ) FEATURE:
        ( A ) NAME/KEY: Modified-site
        ( B ) LOCATION: 2
        ( D ) OTHER INFORMATION: /note="X=(Pmc)"

( x i ) SEQUENCE DESCRIPTION: SEQ ID NO:42:

Arg Xaa Gly His Arg Gly Asp Val Arg Cys Arg
    1                 5                      10

( 2 ) INFORMATION FOR SEQ ID NO:43:

( i ) SEQUENCE CHARACTERISTICS:
        ( A ) LENGTH: 11 amino acids
        ( B ) TYPE: amino acid
        ( C ) STRANDEDNESS: single
        ( D ) TOPOLOGY: circular ( i x ) FEATURE:
        ( A ) NAME/KEY: Modified-site
        ( B ) LOCATION: 2
        ( D ) OTHER INFORMATION: /note="X=(Pmc)"

( x i ) SEQUENCE DESCRIPTION: SEQ ID NO:43:

Arg Xaa Gly His Arg Gly Asp Phe Arg Cys Arg
    1                 5                      10

( 2 ) INFORMATION FOR SEQ ID NO:44:

( i ) SEQUENCE CHARACTERISTICS:
        ( A ) LENGTH: 11 amino acids
        ( B ) TYPE: amino acid
        ( C ) STRANDEDNESS: single
        ( D ) TOPOLOGY: circular ( i x ) FEATURE:
        ( A ) NAME/KEY: Modified-site
        ( B ) LOCATION: 2
        ( D ) OTHER INFORMATION: /note="X=(Pmc)"

( x i ) SEQUENCE DESCRIPTION: SEQ ID NO:44:

Arg Xaa Gly His Arg Gly Asp Tyr Arg Cys Arg
    1                 5                      10

( 2 ) INFORMATION FOR SEQ ID NO:45:

( i ) SEQUENCE CHARACTERISTICS:
        ( A ) LENGTH: 11 amino acids
        ( B ) TYPE: amino acid
        ( C ) STRANDEDNESS: single
        ( D ) TOPOLOGY: circular ( i x ) FEATURE:
        ( A ) NAME/KEY: Modified-site
        ( B ) LOCATION: 2
        ( D ) OTHER INFORMATION: /note="X=(Pmc)"

( i x ) FEATURE:
        ( A ) NAME/KEY: Modified-site
        ( B ) LOCATION: 8
        ( D ) OTHER INFORMATION: /note="X=(O-Me-Y)"

( x i ) SEQUENCE DESCRIPTION: SEQ ID NO:45:

```
Arg  Xaa  Arg  His  Arg  Gly  Asp  Xaa  Arg  Cys  Arg
 1                  5                        10
```

( 2 ) INFORMATION FOR SEQ ID NO:46:

( i ) SEQUENCE CHARACTERISTICS:
        ( A ) LENGTH: 11 amino acids
        ( B ) TYPE: amino acid
        ( C ) STRANDEDNESS: single
        ( D ) TOPOLOGY: circular ( i x ) FEATURE:
        ( A ) NAME/KEY: Modified-site
        ( B ) LOCATION: 2
        ( D ) OTHER INFORMATION: /note="X=(Pmc)"

( i x ) FEATURE:
        ( A ) NAME/KEY: Modified-site
        ( B ) LOCATION: 8
        ( D ) OTHER INFORMATION: /note="X=(Phg)"

( x i ) SEQUENCE DESCRIPTION: SEQ ID NO:46:

```
Arg  Xaa  Gly  His  Arg  Gly  Asp  Xaa  Arg  Cys  Arg
 1                  5                        10
```

( 2 ) INFORMATION FOR SEQ ID NO:47:

( i ) SEQUENCE CHARACTERISTICS:
        ( A ) LENGTH: 11 amino acids
        ( B ) TYPE: amino acid
        ( C ) STRANDEDNESS: single
        ( D ) TOPOLOGY: circular ( i x ) FEATURE:
        ( A ) NAME/KEY: Modified-site
        ( B ) LOCATION: 2
        ( D ) OTHER INFORMATION: /note="X=(Pmc)"

( i x ) FEATURE:
        ( A ) NAME/KEY: Modified-site
        ( B ) LOCATION: 8
        ( D ) OTHER INFORMATION: /note="X=(O-Me-Y)"

( x i ) SEQUENCE DESCRIPTION: SEQ ID NO:47:

```
Phe  Xaa  Gly  His  Arg  Gly  Asp  Xaa  Arg  Cys  Arg
 1                  5                        10
```

( 2 ) INFORMATION FOR SEQ ID NO:48:

( i ) SEQUENCE CHARACTERISTICS:
        ( A ) LENGTH: 11 amino acids
        ( B ) TYPE: amino acid
        ( C ) STRANDEDNESS: single (D) TOPOLOGY: circular (ix) FEATURE:
    (A) NAME/KEY: Modified-site
    (B) LOCATION: 2
    (D) OTHER INFORMATION: /note="X=(dPen)"

(ix) FEATURE:
    (A) NAME/KEY: Modified-site
    (B) LOCATION: 8
    (D) OTHER INFORMATION: /note="X=(p-iodo-F)"

(xi) SEQUENCE DESCRIPTION: SEQ ID NO:48:

```
Arg Xaa Gly His Arg Gly Asp Xaa Arg Cys Arg
 1               5                   10
```

(2) INFORMATION FOR SEQ ID NO:49:

(i) SEQUENCE CHARACTERISTICS:
        (A) LENGTH: 11 amino acids
        (B) TYPE: amino acid
        (C) STRANDEDNESS: single
        (D) TOPOLOGY: circular (ix) FEATURE:
    (A) NAME/KEY: Modified-site
    (B) LOCATION: 2
    (D) OTHER INFORMATION: /note="X=(Pmc)"

(ix) FEATURE:
    (A) NAME/KEY: Modified-site
    (B) LOCATION: 8
    (D) OTHER INFORMATION: /note="X=(O-Me-Y)"

(xi) SEQUENCE DESCRIPTION: SEQ ID NO:49:

```
Lys Xaa Gly His Arg Gly Asp Xaa Arg Cys Lys
 1               5                   10
```

(2) INFORMATION FOR SEQ ID NO:50:

(i) SEQUENCE CHARACTERISTICS:
        (A) LENGTH: 11 amino acids
        (B) TYPE: amino acid
        (C) STRANDEDNESS: single
        (D) TOPOLOGY: circular (ix) FEATURE:
    (A) NAME/KEY: Modified-site
    (B) LOCATION: 2
    (D) OTHER INFORMATION: /note="X=(Pmc)"

(ix) FEATURE:
    (A) NAME/KEY: Modified-site
    (B) LOCATION: 8
    (D) OTHER INFORMATION: /note="X=(O-Me-Y)"

(xi) SEQUENCE DESCRIPTION: SEQ ID NO:50:

```
Arg Xaa Gly His Arg Gly Asp Xaa Arg Cys Arg
 1               5                   10
```

(2) INFORMATION FOR SEQ ID NO:51:

(i) SEQUENCE CHARACTERISTICS:
        (A) LENGTH: 11 amino acids
        (B) TYPE: amino acid
        (C) STRANDEDNESS: single
        (D) TOPOLOGY: circular (ix) FEATURE:
    (A) NAME/KEY: Modified-site
    (B) LOCATION: 2
    (D) OTHER INFORMATION: /note="X=(Pmc)"

(ix) FEATURE:

(A) NAME/KEY: Modified-site
                (B) LOCATION: 8
                (D) OTHER INFORMATION: /note="X=(O-Me-Y)"

(xi) SEQUENCE DESCRIPTION: SEQ ID NO:51:

His Xaa Gly His Arg Gly Asp Xaa Arg Cys Arg
    1               5                   10

(2) INFORMATION FOR SEQ ID NO:52:

(i) SEQUENCE CHARACTERISTICS:
                (A) LENGTH: 11 amino acids
                (B) TYPE: amino acid
                (C) STRANDEDNESS: single
                (D) TOPOLOGY: circular (ix) FEATURE:
                (A) NAME/KEY: Modified-site
                (B) LOCATION: 2
                (D) OTHER INFORMATION: /note="X=(Pmc)"

(ix) FEATURE:
                (A) NAME/KEY: Modified-site
                (B) LOCATION: 8
                (D) OTHER INFORMATION: /note="X=(p-amino-F)"

(xi) SEQUENCE DESCRIPTION: SEQ ID NO:52:

Arg Xaa Gly His Arg Gly Asp Xaa Arg Cys Arg
    1               5                   10

(2) INFORMATION FOR SEQ ID NO:53:

(i) SEQUENCE CHARACTERISTICS:
                (A) LENGTH: 11 amino acids
                (B) TYPE: amino acid
                (C) STRANDEDNESS: single
                (D) TOPOLOGY: circular (ix) FEATURE:
                (A) NAME/KEY: Modified-site
                (B) LOCATION: 2
                (D) OTHER INFORMATION: /note="X=(Pmc)"

(ix) FEATURE:
                (A) NAME/KEY: Modified-site
                (B) LOCATION: 8
                (D) OTHER INFORMATION: /note="X=(O-Me-Y)"

(xi) SEQUENCE DESCRIPTION: SEQ ID NO:53:

Arg Xaa Asn His Arg Gly Asp Xaa Arg Cys Arg
    1               5                   10

(2) INFORMATION FOR SEQ ID NO:54:

(i) SEQUENCE CHARACTERISTICS:
                (A) LENGTH: 11 amino acids
                (B) TYPE: amino acid
                (C) STRANDEDNESS: single
                (D) TOPOLOGY: circular (ix) FEATURE:
                (A) NAME/KEY: Modified-site
                (B) LOCATION: 2
                (D) OTHER INFORMATION: /note="X=(Pmc)"

(ix) FEATURE:
                (A) NAME/KEY: Modified-site
                (B) LOCATION: 8
                (D) OTHER INFORMATION: /note="X=(O-Me-Y)"

(xi) SEQUENCE DESCRIPTION: SEQ ID NO:54:

Gly Xaa Gly His Arg Gly Asp Xaa Arg Cys Arg
    1               5                   10

( 2 ) INFORMATION FOR SEQ ID NO:55:

( i ) SEQUENCE CHARACTERISTICS:
        ( A ) LENGTH: 11 amino acids
        ( B ) TYPE: amino acid
        ( C ) STRANDEDNESS: single
        ( D ) TOPOLOGY: circular ( i x ) FEATURE:
        ( A ) NAME/KEY: Modified-site
        ( B ) LOCATION: 2
        ( D ) OTHER INFORMATION: /note="X=(Pmc)"

( i x ) FEATURE:
        ( A ) NAME/KEY: Modified-site
        ( B ) LOCATION: 8
        ( D ) OTHER INFORMATION: /note="X=(O-Me-Y)"

( x i ) SEQUENCE DESCRIPTION: SEQ ID NO:55:

```
Arg  Xaa  Gly  His  Arg  Gly  Asp  Xaa  Lys  Cys  Arg
1                  5                        10
```

( 2 ) INFORMATION FOR SEQ ID NO:56:

( i ) SEQUENCE CHARACTERISTICS:
        ( A ) LENGTH: 11 amino acids
        ( B ) TYPE: amino acid
        ( C ) STRANDEDNESS: single
        ( D ) TOPOLOGY: circular ( i x ) FEATURE:
        ( A ) NAME/KEY: Modified-site
        ( B ) LOCATION: 2
        ( D ) OTHER INFORMATION: /note="X=Pen"

( x i ) SEQUENCE DESCRIPTION: SEQ ID NO:56:

```
Gly  Xaa  Ile  Ala  Arg  Gly  Asp  Trp  Asn  Cys  Ala
1                  5                        10
```

( 2 ) INFORMATION FOR SEQ ID NO:57:

( i ) SEQUENCE CHARACTERISTICS:
        ( A ) LENGTH: 11 amino acids
        ( B ) TYPE: amino acid
        ( C ) STRANDEDNESS: single
        ( D ) TOPOLOGY: circular ( i x ) FEATURE:
        ( A ) NAME/KEY: Modified-site
        ( B ) LOCATION: 2
        ( D ) OTHER INFORMATION: /note="X=(Pmc)"

( i x ) FEATURE:
        ( A ) NAME/KEY: Modified-site
        ( B ) LOCATION: 8
        ( D ) OTHER INFORMATION: /note="X=(O-Me-Y)"

( x i ) SEQUENCE DESCRIPTION: SEQ ID NO:57:

```
Thr  Xaa  Gly  His  Arg  Gly  Asp  Xaa  Arg  Cys  Arg
1                  5                        10
```

( 2 ) INFORMATION FOR SEQ ID NO:58:

( i ) SEQUENCE CHARACTERISTICS:
        ( A ) LENGTH: 11 amino acids
        ( B ) TYPE: amino acid
        ( C ) STRANDEDNESS: single
        ( D ) TOPOLOGY: circular ( i x ) FEATURE:
        ( A ) NAME/KEY: Modified-site
        ( B ) LOCATION: 2

( D ) OTHER INFORMATION: /note="X=(Pmc)"

( i x ) FEATURE:
( A ) NAME/KEY: Modified-site
( B ) LOCATION: 8
( D ) OTHER INFORMATION: /note="X=(p-nitro-F)"

( x i ) SEQUENCE DESCRIPTION: SEQ ID NO:58:

Arg Xaa Gly His Arg Gly Asp Xaa Lys Cys Arg
1               5                   10

( 2 ) INFORMATION FOR SEQ ID NO:59:

( i ) SEQUENCE CHARACTERISTICS:
( A ) LENGTH: 11 amino acids
( B ) TYPE: amino acid
( C ) STRANDEDNESS: single
( D ) TOPOLOGY: circular ( i x ) FEATURE:
( A ) NAME/KEY: Modified-site
( B ) LOCATION: 2
( D ) OTHER INFORMATION: /note="X=(Pmc)"

( i x ) FEATURE:
( A ) NAME/KEY: Modified-site
( B ) LOCATION: 8
( D ) OTHER INFORMATION: /note="X=(p-iodo-F)"

( x i ) SEQUENCE DESCRIPTION: SEQ ID NO:59:

Arg Xaa Gly His Arg Gly Asp Xaa Lys Cys Arg
1               5                   10

( 2 ) INFORMATION FOR SEQ ID NO:60:

( i ) SEQUENCE CHARACTERISTICS:
( A ) LENGTH: 11 amino acids
( B ) TYPE: amino acid
( C ) STRANDEDNESS: single
( D ) TOPOLOGY: circular ( i x ) FEATURE:
( A ) NAME/KEY: Region
( B ) LOCATION: 1
( D ) OTHER INFORMATION: /note="X=Ac-"

( i x ) FEATURE:
( A ) NAME/KEY: Modified-site
( B ) LOCATION: 2
( D ) OTHER INFORMATION: /note="X=(Pmc)"

( i x ) FEATURE:
( A ) NAME/KEY: Modified-site
( B ) LOCATION: 8
( D ) OTHER INFORMATION: /note="X=(O-Me-Y)"

( i x ) FEATURE:
( A ) NAME/KEY: Region
( B ) LOCATION: 11
( D ) OTHER INFORMATION: /note="X=-N(H)2"

( x i ) SEQUENCE DESCRIPTION: SEQ ID NO:60:

Xaa Xaa Gly His Arg Gly Asp Xaa Arg Cys Xaa
1               5                   10

( 2 ) INFORMATION FOR SEQ ID NO:61:

( i ) SEQUENCE CHARACTERISTICS:
( A ) LENGTH: 11 amino acids
( B ) TYPE: amino acid
( C ) STRANDEDNESS: single
( D ) TOPOLOGY: circular ( i x ) FEATURE:

(A) NAME/KEY: Modified-site
                (B) LOCATION: 2
                (D) OTHER INFORMATION: /note="X=(Pmc)"

(ix) FEATURE:
                (A) NAME/KEY: Modified-site
                (B) LOCATION: 8
                (D) OTHER INFORMATION: /note="X=(O-Me-Y)"

(xi) SEQUENCE DESCRIPTION: SEQ ID NO:61:

Asp  Xaa  Gly  His  Arg  Gly  Asp  Xaa  Arg  Cys  Arg
    1                   5                        10

(2) INFORMATION FOR SEQ ID NO:62:

(i) SEQUENCE CHARACTERISTICS:
                (A) LENGTH: 11 amino acids
                (B) TYPE: amino acid
                (C) STRANDEDNESS: single
                (D) TOPOLOGY: circular (ix) FEATURE:
                (A) NAME/KEY: Region
                (B) LOCATION: 1
                (D) OTHER INFORMATION: /note="X=Ac-"

(ix) FEATURE:
                (A) NAME/KEY: Modified-site
                (B) LOCATION: 8
                (D) OTHER INFORMATION: /note="X=(O-Me-Y)"

(ix) FEATURE:
                (A) NAME/KEY: Region
                (B) LOCATION: 11
                (D) OTHER INFORMATION: /note="X=-N(H)2"

(xi) SEQUENCE DESCRIPTION: SEQ ID NO:62:

Xaa  Cys  Ile  Pro  Arg  Gly  Asp  Xaa  Arg  Cys  Xaa
    1                   5                        10

(2) INFORMATION FOR SEQ ID NO:63:

(i) SEQUENCE CHARACTERISTICS:
                (A) LENGTH: 11 amino acids
                (B) TYPE: amino acid
                (C) STRANDEDNESS: single
                (D) TOPOLOGY: circular (ix) FEATURE:
                (A) NAME/KEY: Region
                (B) LOCATION: 1
                (D) OTHER INFORMATION: /note="X=Ac-"

(ix) FEATURE:
                (A) NAME/KEY: Modified-site
                (B) LOCATION: 2
                (D) OTHER INFORMATION: /note="X=(dPen)"

(ix) FEATURE:
                (A) NAME/KEY: Modified-site
                (B) LOCATION: 8
                (D) OTHER INFORMATION: /note="X=(O-Me-Y)"

(ix) FEATURE:
                (A) NAME/KEY: Region
                (B) LOCATION: 11
                (D) OTHER INFORMATION: /note="X=-N(H)2"

(xi) SEQUENCE DESCRIPTION: SEQ ID NO:63:

Xaa  Xaa  Ile  Pro  Arg  Gly  Asp  Xaa  Arg  Cys  Xaa
    1                   5                        10

(2) INFORMATION FOR SEQ ID NO:64:

(i) SEQUENCE CHARACTERISTICS:
(A) LENGTH: 11 amino acids
(B) TYPE: amino acid
(C) STRANDEDNESS: single
(D) TOPOLOGY: circular (ix) FEATURE:
(A) NAME/KEY: Region
(B) LOCATION: 1
(D) OTHER INFORMATION: /note="X=Ac-"

(ix) FEATURE:
(A) NAME/KEY: Modified-site
(B) LOCATION: 2
(D) OTHER INFORMATION: /note="X=(dPen)"

(ix) FEATURE:
(A) NAME/KEY: Modified-site
(B) LOCATION: 8
(D) OTHER INFORMATION: /note="X=(O-Me-Y)"

(ix) FEATURE:
(A) NAME/KEY: Region
(B) LOCATION: 11
(D) OTHER INFORMATION: /note="X=-N(H)2"

(xi) SEQUENCE DESCRIPTION: SEQ ID NO:64:

Xaa Xaa Asn Pro Arg Gly Asp Xaa Arg Cys Xaa
1               5                   10

(2) INFORMATION FOR SEQ ID NO:65:

(i) SEQUENCE CHARACTERISTICS:
(A) LENGTH: 11 amino acids
(B) TYPE: amino acid
(C) STRANDEDNESS: single
(D) TOPOLOGY: circular (ix) FEATURE:
(A) NAME/KEY: Modified-site
(B) LOCATION: 2
(D) OTHER INFORMATION: /note="X=(dPen)"

(ix) FEATURE:
(A) NAME/KEY: Modified-site
(B) LOCATION: 8
(D) OTHER INFORMATION: /note="X=(O-Me-Y)"

(xi) SEQUENCE DESCRIPTION: SEQ ID NO:65:

Arg Xaa Asn Pro Arg Gly Asp Xaa Arg Cys Arg
1               5                   10

(2) INFORMATION FOR SEQ ID NO:66:

(i) SEQUENCE CHARACTERISTICS:
(A) LENGTH: 8 amino acids
(B) TYPE: amino acid
(C) STRANDEDNESS: single
(D) TOPOLOGY: circular (xi) SEQUENCE DESCRIPTION: SEQ ID NO:66:

Gly Arg Gly Asp Ser Pro Asp Gly
1               5

(2) INFORMATION FOR SEQ ID NO:67:

(i) SEQUENCE CHARACTERISTICS:
(A) LENGTH: 8 amino acids
(B) TYPE: amino acid
(C) STRANDEDNESS: single
(D) TOPOLOGY: circular (xi) SEQUENCE DESCRIPTION: SEQ ID NO:67:

```
       Phe  Arg  Gly  Asp  Ser  Pro  Asp  Gly
       1                  5
```

(2) INFORMATION FOR SEQ ID NO:68:

(i) SEQUENCE CHARACTERISTICS:
    (A) LENGTH: 8 amino acids
    (B) TYPE: amino acid
    (C) STRANDEDNESS: single
    (D) TOPOLOGY: circular (x i) SEQUENCE DESCRIPTION: SEQ ID NO:68:

```
       Tyr  Arg  Gly  Asp  Ser  Pro  Asp  Gly
       1                  5
```

(2) INFORMATION FOR SEQ ID NO:69:

(i) SEQUENCE CHARACTERISTICS:
    (A) LENGTH: 8 amino acids
    (B) TYPE: amino acid
    (C) STRANDEDNESS: single
    (D) TOPOLOGY: circular (x i) SEQUENCE DESCRIPTION: SEQ ID NO:69:

```
       Leu  Arg  Gly  Asp  Ser  Pro  Asp  Gly
       1                  5
```

(2) INFORMATION FOR SEQ ID NO:70:

(i) SEQUENCE CHARACTERISTICS:
    (A) LENGTH: 9 amino acids
    (B) TYPE: amino acid
    (C) STRANDEDNESS: single
    (D) TOPOLOGY: circular (x i) SEQUENCE DESCRIPTION: SEQ ID NO:70:

```
       Asp  Ser  Arg  Gly  Asp  Ser  Pro  Asp  Gly
       1                  5
```

(2) INFORMATION FOR SEQ ID NO:71:

(i) SEQUENCE CHARACTERISTICS:
    (A) LENGTH: 8 amino acids
    (B) TYPE: amino acid
    (C) STRANDEDNESS: single
    (D) TOPOLOGY: circular (x i) SEQUENCE DESCRIPTION: SEQ ID NO:71:

```
       Val  Arg  Gly  Asp  Ser  Pro  Asp  Gly
       1                  5
```

(2) INFORMATION FOR SEQ ID NO:72:

(i) SEQUENCE CHARACTERISTICS:
    (A) LENGTH: 10 amino acids
    (B) TYPE: amino acid
    (C) STRANDEDNESS: single
    (D) TOPOLOGY: circular (i x) FEATURE:
    (A) NAME/KEY: Modified-site
    (B) LOCATION: 2
    (D) OTHER INFORMATION: /note="X=Pen"

(x i) SEQUENCE DESCRIPTION: SEQ ID NO:72:

```
       Gly  Xaa  Gly  Arg  Gly  Asp  Arg  Pro  Cys  Ala
       1                  5                       10
```

(2) INFORMATION FOR SEQ ID NO:73:

(i) SEQUENCE CHARACTERISTICS:
  (A) LENGTH: 10 amino acids
  (B) TYPE: amino acid
  (C) STRANDEDNESS: single
  (D) TOPOLOGY: circular (ix) FEATURE:
  (A) NAME/KEY: Modified-site
  (B) LOCATION: 2
  (D) OTHER INFORMATION: /note="X=Pen"

(xi) SEQUENCE DESCRIPTION: SEQ ID NO:73:

Gly Xaa Leu Arg Gly Asp Thr Pro Cys Ala
1               5                   10

(2) INFORMATION FOR SEQ ID NO:74:

(i) SEQUENCE CHARACTERISTICS:
    (A) LENGTH: 10 amino acids
    (B) TYPE: amino acid
    (C) STRANDEDNESS: single
    (D) TOPOLOGY: circular (ix) FEATURE:
    (A) NAME/KEY: Modified-site
    (B) LOCATION: 2
    (D) OTHER INFORMATION: /note="X=Pen"

(xi) SEQUENCE DESCRIPTION: SEQ ID NO:74:

Gly Xaa Val Arg Gly Asp Ser Pro Cys Ala
1               5                   10

(2) INFORMATION FOR SEQ ID NO:75:

(i) SEQUENCE CHARACTERISTICS:
    (A) LENGTH: 10 amino acids
    (B) TYPE: amino acid
    (C) STRANDEDNESS: single
    (D) TOPOLOGY: circular (ix) FEATURE:
    (A) NAME/KEY: Modified-site
    (B) LOCATION: 2
    (D) OTHER INFORMATION: /note="X=Pen"

(xi) SEQUENCE DESCRIPTION: SEQ ID NO:75:

Gly Xaa Tyr Arg Gly Asp Ser Pro Cys Ala
1               5                   10

(2) INFORMATION FOR SEQ ID NO:76:

(i) SEQUENCE CHARACTERISTICS:
    (A) LENGTH: 10 amino acids
    (B) TYPE: amino acid
    (C) STRANDEDNESS: single
    (D) TOPOLOGY: circular (ix) FEATURE:
    (A) NAME/KEY: Modified-site
    (B) LOCATION: 2
    (D) OTHER INFORMATION: /note="X=Pen"

(xi) SEQUENCE DESCRIPTION: SEQ ID NO:76:

Gly Xaa Leu Arg Gly Asp Ser Pro Cys Ala
1               5                   10

(2) INFORMATION FOR SEQ ID NO:77:

(i) SEQUENCE CHARACTERISTICS:
    (A) LENGTH: 10 amino acids
    (B) TYPE: amino acid (C) STRANDEDNESS: single
(D) TOPOLOGY: circular (ix) FEATURE:
(A) NAME/KEY: Modified-site
(B) LOCATION: 2
(D) OTHER INFORMATION: /note="X=Pen"

(xi) SEQUENCE DESCRIPTION: SEQ ID NO:77:

```
Gly Xaa Leu Arg Gly Asp Ser Arg Cys Ala
1               5                   10
```

(2) INFORMATION FOR SEQ ID NO:78:

(i) SEQUENCE CHARACTERISTICS:
(A) LENGTH: 10 amino acids
(B) TYPE: amino acid
(C) STRANDEDNESS: single
(D) TOPOLOGY: circular (ix) FEATURE:
(A) NAME/KEY: Modified-site
(B) LOCATION: 2
(D) OTHER INFORMATION: /note="X=Pen"

(xi) SEQUENCE DESCRIPTION: SEQ ID NO:78:

```
Gly Xaa Gly Arg Gly Asp Ser Phe Cys Ala
1               5                   10
```

(2) INFORMATION FOR SEQ ID NO:79:

(i) SEQUENCE CHARACTERISTICS:
(A) LENGTH: 10 amino acids
(B) TYPE: amino acid
(C) STRANDEDNESS: single
(D) TOPOLOGY: circular (ix) FEATURE:
(A) NAME/KEY: Modified-site
(B) LOCATION: 2
(D) OTHER INFORMATION: /note="X=Pen"

(xi) SEQUENCE DESCRIPTION: SEQ ID NO:79:

```
Gly Xaa Phe Arg Gly Asp Ser Phe Cys Ala
1               5                   10
```

(2) INFORMATION FOR SEQ ID NO:80:

(i) SEQUENCE CHARACTERISTICS:
(A) LENGTH: 10 amino acids
(B) TYPE: amino acid
(C) STRANDEDNESS: single
(D) TOPOLOGY: circular (ix) FEATURE:
(A) NAME/KEY: Modified-site
(B) LOCATION: 2
(D) OTHER INFORMATION: /note="X=Pen"

(xi) SEQUENCE DESCRIPTION: SEQ ID NO:80:

```
Gly Xaa Gly Arg Gly Asp Thr Pro Cys Arg
1               5                   10
```

(2) INFORMATION FOR SEQ ID NO:81:

(i) SEQUENCE CHARACTERISTICS:
(A) LENGTH: 10 amino acids
(B) TYPE: amino acid
(C) STRANDEDNESS: single
(D) TOPOLOGY: circular (ix) FEATURE:

(A) NAME/KEY: Modified-site
(B) LOCATION: 2
(D) OTHER INFORMATION: /note="X=Pen"

(xi) SEQUENCE DESCRIPTION: SEQ ID NO:81:

Arg Xaa Gly Arg Gly Asp Thr Pro Cys Ala
1               5                   10

(2) INFORMATION FOR SEQ ID NO:82:

(i) SEQUENCE CHARACTERISTICS:
(A) LENGTH: 10 amino acids
(B) TYPE: amino acid
(C) STRANDEDNESS: single
(D) TOPOLOGY: circular (ix) FEATURE:
(A) NAME/KEY: Modified-site
(B) LOCATION: 2
(D) OTHER INFORMATION: /note="X=Pen"

(xi) SEQUENCE DESCRIPTION: SEQ ID NO:82:

Lys Xaa Gly Arg Gly Asp Thr Pro Cys Ala
1               5                   10

(2) INFORMATION FOR SEQ ID NO:83:

(i) SEQUENCE CHARACTERISTICS:
(A) LENGTH: 10 amino acids
(B) TYPE: amino acid
(C) STRANDEDNESS: single
(D) TOPOLOGY: circular (ix) FEATURE:
(A) NAME/KEY: Modified-site
(B) LOCATION: 2
(D) OTHER INFORMATION: /note="X=Pen"

(xi) SEQUENCE DESCRIPTION: SEQ ID NO:83:

Arg Xaa Gly Arg Gly Asp Thr Pro Cys Arg
1               5                   10

(2) INFORMATION FOR SEQ ID NO:84:

(i) SEQUENCE CHARACTERISTICS:
(A) LENGTH: 10 amino acids
(B) TYPE: amino acid
(C) STRANDEDNESS: single
(D) TOPOLOGY: circular (ix) FEATURE:
(A) NAME/KEY: Modified-site
(B) LOCATION: 2
(D) OTHER INFORMATION: /note="X=Pen"

(xi) SEQUENCE DESCRIPTION: SEQ ID NO:84:

Arg Xaa Gly Arg Gly Asp Thr Pro Cys Lys
1               5                   10

(2) INFORMATION FOR SEQ ID NO:85:

(i) SEQUENCE CHARACTERISTICS:
(A) LENGTH: 10 amino acids
(B) TYPE: amino acid
(C) STRANDEDNESS: single
(D) TOPOLOGY: circular (ix) FEATURE:
(A) NAME/KEY: Modified-site
(B) LOCATION: 2
(D) OTHER INFORMATION: /note="X=Pen"

( x i ) SEQUENCE DESCRIPTION: SEQ ID NO:85:

Arg Xaa Gly Arg Gly Asp Ser Arg Cys Ala
1               5                       10

( 2 ) INFORMATION FOR SEQ ID NO:86:

( i ) SEQUENCE CHARACTERISTICS:
        ( A ) LENGTH: 10 amino acids
        ( B ) TYPE: amino acid
        ( C ) STRANDEDNESS: single
        ( D ) TOPOLOGY: circular ( i x ) FEATURE:
        ( A ) NAME/KEY: Modified-site
        ( B ) LOCATION: 2
        ( D ) OTHER INFORMATION: /note="X=Pen"

( x i ) SEQUENCE DESCRIPTION: SEQ ID NO:86:

Arg Xaa Gly Arg Gly Asp Leu Arg Cys Ala
1               5                       10

( 2 ) INFORMATION FOR SEQ ID NO:87:

( i ) SEQUENCE CHARACTERISTICS:
        ( A ) LENGTH: 11 amino acids
        ( B ) TYPE: amino acid
        ( C ) STRANDEDNESS: single
        ( D ) TOPOLOGY: circular ( i x ) FEATURE:
        ( A ) NAME/KEY: Modified-site
        ( B ) LOCATION: 2
        ( D ) OTHER INFORMATION: /note="X=Pen"

( x i ) SEQUENCE DESCRIPTION: SEQ ID NO:87:

Gly Xaa Gly His Arg Gly Asp Thr Arg Cys Ala
1               5                       10

( 2 ) INFORMATION FOR SEQ ID NO:88:

( i ) SEQUENCE CHARACTERISTICS:
        ( A ) LENGTH: 10 amino acids
        ( B ) TYPE: amino acid
        ( C ) STRANDEDNESS: single
        ( D ) TOPOLOGY: circular ( i x ) FEATURE:
        ( A ) NAME/KEY: Modified-site
        ( B ) LOCATION: 1
        ( D ) OTHER INFORMATION: /note="X=R(2)"

( i x ) FEATURE:
        ( A ) NAME/KEY: Modified-site
        ( B ) LOCATION: 2
        ( D ) OTHER INFORMATION: /note="X=Pen"

( x i ) SEQUENCE DESCRIPTION: SEQ ID NO:88:

Xaa Xaa Gly Arg Gly Asp Thr Pro Cys Ala
1               5                       10

( 2 ) INFORMATION FOR SEQ ID NO:89:

( i ) SEQUENCE CHARACTERISTICS:
        ( A ) LENGTH: 11 amino acids
        ( B ) TYPE: amino acid
        ( C ) STRANDEDNESS: single
        ( D ) TOPOLOGY: circular ( i x ) FEATURE:
        ( A ) NAME/KEY: Modified-site
        ( B ) LOCATION: 2
        ( D ) OTHER INFORMATION: /note="X=Pen"

( x i ) SEQUENCE DESCRIPTION: SEQ ID NO:89:

Arg Xaa Gly His Arg Gly Asp Thr Arg Cys Arg
1               5                   10

( 2 ) INFORMATION FOR SEQ ID NO:90:

( i ) SEQUENCE CHARACTERISTICS:
        ( A ) LENGTH: 11 amino acids
        ( B ) TYPE: amino acid
        ( C ) STRANDEDNESS: single
        ( D ) TOPOLOGY: circular ( i x ) FEATURE:
        ( A ) NAME/KEY: Modified-site
        ( B ) LOCATION: 2
        ( D ) OTHER INFORMATION: /note="X=Pen"

( x i ) SEQUENCE DESCRIPTION: SEQ ID NO:90:

Leu Xaa Gly His Arg Gly Asp Leu Arg Cys Ala
1               5                   10

( 2 ) INFORMATION FOR SEQ ID NO:91:

( i ) SEQUENCE CHARACTERISTICS:
        ( A ) LENGTH: 9 amino acids
        ( B ) TYPE: amino acid
        ( C ) STRANDEDNESS: single
        ( D ) TOPOLOGY: circular ( i x ) FEATURE:
        ( A ) NAME/KEY: Modified-site
        ( B ) LOCATION: 1
        ( D ) OTHER INFORMATION: /note="X=Pmp"

( x i ) SEQUENCE DESCRIPTION: SEQ ID NO:91:

Xaa Gly Arg Gly Asp Ser Pro Cys Ala
1               5

( 2 ) INFORMATION FOR SEQ ID NO:92:

( i ) SEQUENCE CHARACTERISTICS:
        ( A ) LENGTH: 9 amino acids
        ( B ) TYPE: amino acid
        ( C ) STRANDEDNESS: single
        ( D ) TOPOLOGY: circular ( i x ) FEATURE:
        ( A ) NAME/KEY: Modified-site
        ( B ) LOCATION: 1
        ( D ) OTHER INFORMATION: /note="X=Pmp"

( x i ) SEQUENCE DESCRIPTION: SEQ ID NO:92:

Xaa Gly Arg Gly Asp Thr Pro Cys Ala
1               5

( 2 ) INFORMATION FOR SEQ ID NO:93:

( i ) SEQUENCE CHARACTERISTICS:
        ( A ) LENGTH: 10 amino acids
        ( B ) TYPE: amino acid
        ( C ) STRANDEDNESS: single
        ( D ) TOPOLOGY: circular ( i x ) FEATURE:
        ( A ) NAME/KEY: Modified-site
        ( B ) LOCATION: 1
        ( D ) OTHER INFORMATION: /note="X=Pmp"

( i x ) FEATURE:
        ( A ) NAME/KEY: Modified-site
        ( B ) LOCATION: 9

(D) OTHER INFORMATION: /note="X=Pen"

(xi) SEQUENCE DESCRIPTION: SEQ ID NO:93:

Xaa Gly His Arg Gly Asp Leu Arg Xaa Ala
1               5                   10

(2) INFORMATION FOR SEQ ID NO:94:

(i) SEQUENCE CHARACTERISTICS:
    (A) LENGTH: 10 amino acids
    (B) TYPE: amino acid
    (C) STRANDEDNESS: single
    (D) TOPOLOGY: circular (ix) FEATURE:
    (A) NAME/KEY: Modified-site
    (B) LOCATION: 1
    (D) OTHER INFORMATION: /note="X=(t-butyl-Pmc)"

(xi) SEQUENCE DESCRIPTION: SEQ ID NO:94:

Xaa Gly His Arg Gly Asp Leu Arg Cys Ala
1               5                   10

(2) INFORMATION FOR SEQ ID NO:95:

(i) SEQUENCE CHARACTERISTICS:
    (A) LENGTH: 10 amino acids
    (B) TYPE: amino acid
    (C) STRANDEDNESS: single
    (D) TOPOLOGY: circular (ix) FEATURE:
    (A) NAME/KEY: Modified-site
    (B) LOCATION: 2
    (D) OTHER INFORMATION: /note="X=(Pmc)"

(xi) SEQUENCE DESCRIPTION: SEQ ID NO:95:

Arg Xaa Gly Arg Gly Asp Thr Pro Cys Ala
1               5                   10

(2) INFORMATION FOR SEQ ID NO:96:

(i) SEQUENCE CHARACTERISTICS:
    (A) LENGTH: 11 amino acids
    (B) TYPE: amino acid
    (C) STRANDEDNESS: single
    (D) TOPOLOGY: circular (xi) SEQUENCE DESCRIPTION: SEQ ID NO:96:

Gly His Arg Gly Asp Leu Arg Asp Ala Ser Gly
1               5                   10

(2) INFORMATION FOR SEQ ID NO:97:

(i) SEQUENCE CHARACTERISTICS:
    (A) LENGTH: 11 amino acids
    (B) TYPE: amino acid
    (C) STRANDEDNESS: single
    (D) TOPOLOGY: circular (xi) SEQUENCE DESCRIPTION: SEQ ID NO:97:

Arg Lys Gly His Arg Gly Asp Leu Arg Asp Arg
1               5                   10

(2) INFORMATION FOR SEQ ID NO:98:

(i) SEQUENCE CHARACTERISTICS:
    (A) LENGTH: 14 amino acids
    (B) TYPE: amino acid
    (C) STRANDEDNESS: single (D) TOPOLOGY: circular (ix) FEATURE:
    (A) NAME/KEY: Modified-site
    (B) LOCATION: 2
    (D) OTHER INFORMATION: /note="X=(orn)"

(xi) SEQUENCE DESCRIPTION: SEQ ID NO:98:

```
Arg Xaa Gly His Arg Gly Asp Leu Arg Asp Arg Ala Ser Gly
 1           5                  10
```

(2) INFORMATION FOR SEQ ID NO:99:

(i) SEQUENCE CHARACTERISTICS:
        (A) LENGTH: 11 amino acids
        (B) TYPE: amino acid
        (C) STRANDEDNESS: single
        (D) TOPOLOGY: circular (ix) FEATURE:
    (A) NAME/KEY: Modified-site
    (B) LOCATION: 2
    (D) OTHER INFORMATION: /note="X=(orn)"

(xi) SEQUENCE DESCRIPTION: SEQ ID NO:99:

```
Arg Xaa Gly His Arg Gly Asp Leu Arg Asp Arg
 1           5                  10
```

(2) INFORMATION FOR SEQ ID NO:100:

(i) SEQUENCE CHARACTERISTICS:
        (A) LENGTH: 11 amino acids
        (B) TYPE: amino acid
        (C) STRANDEDNESS: single
        (D) TOPOLOGY: circular (ix) FEATURE:
    (A) NAME/KEY: Modified-site
    (B) LOCATION: 2
    (D) OTHER INFORMATION: /note="X=(orn)"

(xi) SEQUENCE DESCRIPTION: SEQ ID NO:100:

```
Arg Xaa Gly His Arg Gly Asp Leu Arg Glu Arg
 1           5                  10
```

(2) INFORMATION FOR SEQ ID NO:101:

(i) SEQUENCE CHARACTERISTICS:
        (A) LENGTH: 8 amino acids
        (B) TYPE: amino acid
        (C) STRANDEDNESS: single
        (D) TOPOLOGY: circular (ix) FEATURE:
    (A) NAME/KEY: Modified-site
    (B) LOCATION: 8
    (D) OTHER INFORMATION: /note="X=PasA-N(H)2"

(xi) SEQUENCE DESCRIPTION: SEQ ID NO:101:

```
Gly His Arg Gly Asp Leu Arg Xaa
 1           5
```

(2) INFORMATION FOR SEQ ID NO:102:

(i) SEQUENCE CHARACTERISTICS:
        (A) LENGTH: 4 amino acids
        (B) TYPE: amino acid
        (C) STRANDEDNESS: single
        (D) TOPOLOGY: circular (ix) FEATURE:
    (A) NAME/KEY: Modified-site (B) LOCATION: 1
(D) OTHER INFORMATION: /note="X=R(9)"

(x i) SEQUENCE DESCRIPTION: SEQ ID NO:102:

Xaa Gly Asp Ser
1

(2) INFORMATION FOR SEQ ID NO:103:

(i) SEQUENCE CHARACTERISTICS:
(A) LENGTH: 11 amino acids
(B) TYPE: amino acid
(C) STRANDEDNESS: single
(D) TOPOLOGY: circular (i x) FEATURE:
(A) NAME/KEY: Region
(B) LOCATION: 1
(D) OTHER INFORMATION: /note="X=Ac-"

(i x) FEATURE:
(A) NAME/KEY: Modified-site
(B) LOCATION: 8
(D) OTHER INFORMATION: /note="X=(O-Me-Y)"

(i x) FEATURE:
(A) NAME/KEY: Region
(B) LOCATION: 11
(D) OTHER INFORMATION: /note="X=-N(H)2"

(x i) SEQUENCE DESCRIPTION: SEQ ID NO:103:

Xaa Cys Asn Pro Arg Gly Asp Xaa Glu Cys Xaa
1               5                   10

(2) INFORMATION FOR SEQ ID NO:104:

(i) SEQUENCE CHARACTERISTICS:
(A) LENGTH: 11 amino acids
(B) TYPE: amino acid
(C) STRANDEDNESS: single
(D) TOPOLOGY: circular (i x) FEATURE:
(A) NAME/KEY: Region
(B) LOCATION: 1
(D) OTHER INFORMATION: /note="X=Ac-"

(i x) FEATURE:
(A) NAME/KEY: Modified-site
(B) LOCATION: 8
(D) OTHER INFORMATION: /note="X=(O-Me-Y)"

(i x) FEATURE:
(A) NAME/KEY: Region
(B) LOCATION: 11
(D) OTHER INFORMATION: /note="X=-N(H)2"

(x i) SEQUENCE DESCRIPTION: SEQ ID NO:104:

Xaa Cys Asn Pro Arg Gly Asp Xaa Ala Cys Xaa
1               5                   10

(2) INFORMATION FOR SEQ ID NO:105:

(i) SEQUENCE CHARACTERISTICS:
(A) LENGTH: 10 amino acids
(B) TYPE: amino acid
(C) STRANDEDNESS: single
(D) TOPOLOGY: circular (i x) FEATURE:
(A) NAME/KEY: Region
(B) LOCATION: 1
(D) OTHER INFORMATION: /note="X=Ac-"

( i x ) FEATURE:
  ( A ) NAME/KEY: Modified-site
  ( B ) LOCATION: 8
  ( D ) OTHER INFORMATION: /note="X=(O-Me-Y)"

( i x ) FEATURE:
  ( A ) NAME/KEY: Modified-site
  ( B ) LOCATION: 9
  ( D ) OTHER INFORMATION: /note="X=(dR)"

( i x ) FEATURE:
  ( A ) NAME/KEY: Region
  ( B ) LOCATION: 10
  ( D ) OTHER INFORMATION: /note="X=C-N(H)2"

( x i ) SEQUENCE DESCRIPTION: SEQ ID NO:105:

Xaa Cys Asn Pro Arg Gly Asp Xaa Xaa Xaa
1       5         10

( 2 ) INFORMATION FOR SEQ ID NO:106:

( i ) SEQUENCE CHARACTERISTICS:
  ( A ) LENGTH: 10 amino acids
  ( B ) TYPE: amino acid
  ( C ) STRANDEDNESS: single
  ( D ) TOPOLOGY: circular ( i x ) FEATURE:
  ( A ) NAME/KEY: Region
  ( B ) LOCATION: 1
  ( D ) OTHER INFORMATION: /note="X=Ac-"

( i x ) FEATURE:
  ( A ) NAME/KEY: Modified-site
  ( B ) LOCATION: 8
  ( D ) OTHER INFORMATION: /note="X=(O-Me-Y)"

( i x ) FEATURE:
  ( A ) NAME/KEY: Modified-site
  ( B ) LOCATION: 9
  ( D ) OTHER INFORMATION: /note="X=OC"

( i x ) FEATURE:
  ( A ) NAME/KEY: Region
  ( B ) LOCATION: 10
  ( D ) OTHER INFORMATION: /note="X=N(H)2"

( x i ) SEQUENCE DESCRIPTION: SEQ ID NO:106:

Xaa Cys Asn Pro Arg Gly Asp Xaa Xaa Xaa
1       5         10

( 2 ) INFORMATION FOR SEQ ID NO:107:

( i ) SEQUENCE CHARACTERISTICS:
  ( A ) LENGTH: 11 amino acids
  ( B ) TYPE: amino acid
  ( C ) STRANDEDNESS: single
  ( D ) TOPOLOGY: circular ( i x ) FEATURE:
  ( A ) NAME/KEY: Region
  ( B ) LOCATION: 1
  ( D ) OTHER INFORMATION: /note="X=Ac-"

( i x ) FEATURE:
  ( A ) NAME/KEY: Modified-site
  ( B ) LOCATION: 8
  ( D ) OTHER INFORMATION: /note="X=(O-Me-Y)"

( i x ) FEATURE:
  ( A ) NAME/KEY: Region
  ( B ) LOCATION: 11
  ( D ) OTHER INFORMATION: /note="X=-N(H)2"

( x i ) SEQUENCE DESCRIPTION: SEQ ID NO:107:

Xaa Cys Asn Pro Arg Gly Asp Xaa Lys Cys Xaa
1               5                   10

( 2 ) INFORMATION FOR SEQ ID NO:108:

( i ) SEQUENCE CHARACTERISTICS:
       ( A ) LENGTH: 10 amino acids
       ( B ) TYPE: amino acid
       ( C ) STRANDEDNESS: single
       ( D ) TOPOLOGY: circular ( i x ) FEATURE:
       ( A ) NAME/KEY: Region
       ( B ) LOCATION: 1
       ( D ) OTHER INFORMATION: /note="X=Ac-"

( i x ) FEATURE:
       ( A ) NAME/KEY: Modified-site
       ( B ) LOCATION: 8
       ( D ) OTHER INFORMATION: /note="X=(O-Me-Y)"

( i x ) FEATURE:
       ( A ) NAME/KEY: Modified-site
       ( B ) LOCATION: 9
       ( D ) OTHER INFORMATION: /note="X=(Cit)C"

( i x ) FEATURE:
       ( A ) NAME/KEY: Region
       ( B ) LOCATION: 10
       ( D ) OTHER INFORMATION: /note="X=-N(H)2"

( x i ) SEQUENCE DESCRIPTION: SEQ ID NO:108:

Xaa Cys Asn Pro Arg Gly Asp Xaa Xaa Xaa
1               5                   10

( 2 ) INFORMATION FOR SEQ ID NO:109:

( i ) SEQUENCE CHARACTERISTICS:
       ( A ) LENGTH: 10 amino acids
       ( B ) TYPE: amino acid
       ( C ) STRANDEDNESS: single
       ( D ) TOPOLOGY: circular ( i x ) FEATURE:
       ( A ) NAME/KEY: Region
       ( B ) LOCATION: 1
       ( D ) OTHER INFORMATION: /note="X=Ac-"

( i x ) FEATURE:
       ( A ) NAME/KEY: Modified-site
       ( B ) LOCATION: 8
       ( D ) OTHER INFORMATION: /note="X=(O-Me-Y)"

( i x ) FEATURE:
       ( A ) NAME/KEY: Modified-site
       ( B ) LOCATION: 9
       ( D ) OTHER INFORMATION: /note="X=(Nle)C"

( i x ) FEATURE:
       ( A ) NAME/KEY: Region
       ( B ) LOCATION: 10
       ( D ) OTHER INFORMATION: /note="X=-N(H)2"

( x i ) SEQUENCE DESCRIPTION: SEQ ID NO:109:

Xaa Cys Asn Pro Arg Gly Asp Xaa Xaa Xaa
1               5                   10

( 2 ) INFORMATION FOR SEQ ID NO:110:

( i ) SEQUENCE CHARACTERISTICS:
       ( A ) LENGTH: 11 amino acids
       ( B ) TYPE: amino acid
       ( C ) STRANDEDNESS: single
       ( D ) TOPOLOGY: circular ( i x ) FEATURE:
    ( A ) NAME/KEY: Modified-site
    ( B ) LOCATION: 2
    ( D ) OTHER INFORMATION: /note="X=Pen"

( x i ) SEQUENCE DESCRIPTION: SEQ ID NO:110:

Gly Xaa Arg Ala Arg Gly Asp Asn Pro Cys Ala
1               5                   10

( 2 ) INFORMATION FOR SEQ ID NO:111:

( i ) SEQUENCE CHARACTERISTICS:
        ( A ) LENGTH: 11 amino acids
        ( B ) TYPE: amino acid
        ( C ) STRANDEDNESS: single
        ( D ) TOPOLOGY: circular ( i x ) FEATURE:
        ( A ) NAME/KEY: Modified-site
        ( B ) LOCATION: 2
        ( D ) OTHER INFORMATION: /note="X=(Pmc)"

( i x ) FEATURE:
        ( A ) NAME/KEY: Modified-site
        ( B ) LOCATION: 8
        ( D ) OTHER INFORMATION: /note="X=(p-I-F)"

( x i ) SEQUENCE DESCRIPTION: SEQ ID NO:111:

Arg Xaa Gly His Arg Gly Asp Xaa Arg Cys Arg
1               5                   10

( 2 ) INFORMATION FOR SEQ ID NO:112:

( i ) SEQUENCE CHARACTERISTICS:
        ( A ) LENGTH: 11 amino acids
        ( B ) TYPE: amino acid
        ( C ) STRANDEDNESS: single
        ( D ) TOPOLOGY: circular ( i x ) FEATURE:
        ( A ) NAME/KEY: Modified-site
        ( B ) LOCATION: 2
        ( D ) OTHER INFORMATION: /note="X=(Pmc)"

( i x ) FEATURE:
        ( A ) NAME/KEY: Modified-site
        ( B ) LOCATION: 8
        ( D ) OTHER INFORMATION: /note="X=(P-N(O)2-F)"

( x i ) SEQUENCE DESCRIPTION: SEQ ID NO:112:

Arg Xaa Gly His Arg Gly Asp Xaa Arg Cys Arg
1               5                   10

( 2 ) INFORMATION FOR SEQ ID NO:113:

( i ) SEQUENCE CHARACTERISTICS:
        ( A ) LENGTH: 11 amino acids
        ( B ) TYPE: amino acid
        ( C ) STRANDEDNESS: single
        ( D ) TOPOLOGY: circular ( i x ) FEATURE:
        ( A ) NAME/KEY: Region
        ( B ) LOCATION: 1
        ( D ) OTHER INFORMATION: /note="X=Ac-"

( i x ) FEATURE:
        ( A ) NAME/KEY: Modified-site
        ( B ) LOCATION: 8
        ( D ) OTHER INFORMATION: /note="X=(O-Me-Y)"

( i x ) FEATURE:
        ( A ) NAME/KEY: Region
        ( B ) LOCATION: 11

5,612,311

89

-continued ( D ) OTHER INFORMATION: /note="X=-N(H)2"

( x i ) SEQUENCE DESCRIPTION: SEQ ID NO:113:

Xaa  Cys  Ile  Pro  Arg  Gly  Asp  Xaa  Arg  Cys  Xaa
        1                  5                        10

( 2 ) INFORMATION FOR SEQ ID NO:114:

( i ) SEQUENCE CHARACTERISTICS:
                ( A ) LENGTH: 11 amino acids
                ( B ) TYPE: amino acid
                ( C ) STRANDEDNESS: single
                ( D ) TOPOLOGY: circular ( i x ) FEATURE:
                ( A ) NAME/KEY: Region
                ( B ) LOCATION: 1
                ( D ) OTHER INFORMATION: /note="X=Ac-"

( i x ) FEATURE:
                ( A ) NAME/KEY: Modified-site
                ( B ) LOCATION: 2
                ( D ) OTHER INFORMATION: /note="X=(dPen)"

( i x ) FEATURE:
                ( A ) NAME/KEY: Modified-site
                ( B ) LOCATION: 8
                ( D ) OTHER INFORMATION: /note="X=(O-Me-Y)"

( i x ) FEATURE:
                ( A ) NAME/KEY: Region
                ( B ) LOCATION: 11
                ( D ) OTHER INFORMATION: /note="X=-N(H)2"

( x i ) SEQUENCE DESCRIPTION: SEQ ID NO:114:

Xaa  Xaa  Asn  Pro  Arg  Gly  Asp  Xaa  Arg  Cys  Xaa
        1                  5                        10

( 2 ) INFORMATION FOR SEQ ID NO:115:

( i ) SEQUENCE CHARACTERISTICS:
                ( A ) LENGTH: 11 amino acids
                ( B ) TYPE: amino acid
                ( C ) STRANDEDNESS: single
                ( D ) TOPOLOGY: circular ( i x ) FEATURE:
                ( A ) NAME/KEY: Region
                ( B ) LOCATION: 1
                ( D ) OTHER INFORMATION: /note="X=Ac-"

( i x ) FEATURE:
                ( A ) NAME/KEY: Modified-site
                ( B ) LOCATION: 8
                ( D ) OTHER INFORMATION: /note="X=(O-Me-Y)"

( i x ) FEATURE:
                ( A ) NAME/KEY: Region
                ( B ) LOCATION: 11
                ( D ) OTHER INFORMATION: /note="X=-N(H)2"

( x i ) SEQUENCE DESCRIPTION: SEQ ID NO:115:

Xaa  Cys  Ser  Pro  Arg  Gly  Asp  Xaa  Arg  Cys  Xaa
        1                  5                        10

( 2 ) INFORMATION FOR SEQ ID NO:116:

( i ) SEQUENCE CHARACTERISTICS:
                ( A ) LENGTH: 11 amino acids
                ( B ) TYPE: amino acid
                ( C ) STRANDEDNESS: single
                ( D ) TOPOLOGY: circular ( i x ) FEATURE:

(A) NAME/KEY: Region
(B) LOCATION: 1
(D) OTHER INFORMATION: /note="X=Ac-"

( i x ) FEATURE:
(A) NAME/KEY: Modified-site
(B) LOCATION: 8
(D) OTHER INFORMATION: /note="X=(O-Me-Y)"

( i x ) FEATURE:
(A) NAME/KEY: Region
(B) LOCATION: 11
(D) OTHER INFORMATION: /note="X=-N(H)2"

( x i ) SEQUENCE DESCRIPTION: SEQ ID NO:116:

```
Xaa Cys Ala Pro Arg Gly Asp Xaa Arg Cys Xaa
 1               5                   10
```

( 2 ) INFORMATION FOR SEQ ID NO:117:

( i ) SEQUENCE CHARACTERISTICS:
(A) LENGTH: 11 amino acids
(B) TYPE: amino acid
(C) STRANDEDNESS: single
(D) TOPOLOGY: circular ( i x ) FEATURE:
(A) NAME/KEY: Region
(B) LOCATION: 1
(D) OTHER INFORMATION: /note="X=Ac-"

( i x ) FEATURE:
(A) NAME/KEY: Modified-site
(B) LOCATION: 8
(D) OTHER INFORMATION: /note="X=(O-Me-Y)"

( i x ) FEATURE:
(A) NAME/KEY: Region
(B) LOCATION: 11
(D) OTHER INFORMATION: /note="X=-N(H)2"

( x i ) SEQUENCE DESCRIPTION: SEQ ID NO:117:

```
Xaa Cys Leu Pro Arg Gly Asp Xaa Arg Cys Xaa
 1               5                   10
```

( 2 ) INFORMATION FOR SEQ ID NO:118:

( i ) SEQUENCE CHARACTERISTICS:
(A) LENGTH: 11 amino acids
(B) TYPE: amino acid
(C) STRANDEDNESS: single
(D) TOPOLOGY: circular ( i x ) FEATURE:
(A) NAME/KEY: Region
(B) LOCATION: 1
(D) OTHER INFORMATION: /note="X=Ac-"

( i x ) FEATURE:
(A) NAME/KEY: Modified-site
(B) LOCATION: 8
(D) OTHER INFORMATION: /note="X=(O-Me-Y)"

( i x ) FEATURE:
(A) NAME/KEY: Region
(B) LOCATION: 11
(D) OTHER INFORMATION: /note="X=-N(H)2"

( x i ) SEQUENCE DESCRIPTION: SEQ ID NO:118:

```
Xaa Cys Asp Pro Arg Gly Asp Xaa Arg Cys Xaa
 1               5                   10
```

( 2 ) INFORMATION FOR SEQ ID NO:119:

```
    ( i ) SEQUENCE CHARACTERISTICS:
            ( A ) LENGTH: 11 amino acids
            ( B ) TYPE: amino acid
            ( C ) STRANDEDNESS: single
            ( D ) TOPOLOGY: circular ( i x ) FEATURE:
            ( A ) NAME/KEY: Region
            ( B ) LOCATION: 1
            ( D ) OTHER INFORMATION: /note="X=Ac-"

( i x ) FEATURE:
            ( A ) NAME/KEY: Modified-site
            ( B ) LOCATION: 8
            ( D ) OTHER INFORMATION: /note="X=(O-Me-Y)"

( i x ) FEATURE:
            ( A ) NAME/KEY: Region
            ( B ) LOCATION: 11
            ( D ) OTHER INFORMATION: /note="X=-N(H)2"

( x i ) SEQUENCE DESCRIPTION: SEQ ID NO:119:

Xaa  Cys  Tyr  Pro  Arg  Gly  Asp  Xaa  Arg  Cys  Xaa
    1                   5                        10

( 2 ) INFORMATION FOR SEQ ID NO:120:

( i ) SEQUENCE CHARACTERISTICS:
            ( A ) LENGTH: 11 amino acids
            ( B ) TYPE: amino acid
            ( C ) STRANDEDNESS: single
            ( D ) TOPOLOGY: circular ( i x ) FEATURE:
            ( A ) NAME/KEY: Region
            ( B ) LOCATION: 1
            ( D ) OTHER INFORMATION: /note="X=Ac-"

( i x ) FEATURE:
            ( A ) NAME/KEY: Modified-site
            ( B ) LOCATION: 8
            ( D ) OTHER INFORMATION: /note="X=(O-Me-Y)"

( i x ) FEATURE:
            ( A ) NAME/KEY: Region
            ( B ) LOCATION: 11
            ( D ) OTHER INFORMATION: /note="X=-N(H)2"

( x i ) SEQUENCE DESCRIPTION: SEQ ID NO:120:

Xaa  Cys  Arg  Pro  Arg  Gly  Asp  Xaa  Arg  Cys  Xaa
    1                   5                        10
```